(12) United States Patent
Lukyanov et al.

(10) Patent No.: US 7,338,784 B2
(45) Date of Patent: Mar. 4, 2008

(54) NUCLEIC ACIDS ENCODING CHROMOPHORES/FLUOROPHORES AND METHODS FOR USING THE SAME

(75) Inventors: Sergey A. Lukyanov, Moscow (RU); Arcady F. Fradkov, Moscow (RU); Yulii A. Labas, Moscow (RU); Mikhail V. Matz, St. Augustine, FL (US); Alexey Terskikh, Palo Alto, CA (US)

(73) Assignee: Clontech Laboratories, Inc, Mountain View, CA (US)

( * ) Notice: Subject to any disclaimer, the term of this patent is extended or adjusted under 35 U.S.C. 154(b) by 0 days.

(21) Appl. No.: 11/607,706

(22) Filed: Nov. 30, 2006

(65) Prior Publication Data

US 2007/0141608 A1    Jun. 21, 2007

Related U.S. Application Data

(60) Division of application No. 10/006,922, filed on Dec. 4, 2001, now Pat. No. 7,166,444, which is a continuation-in-part of application No. PCT/US00/28477, filed on Oct. 13, 2000, and a continuation-in-part of application No. 09/457,898, filed on Dec. 9, 1999, now abandoned, and a continuation-in-part of application No. 09/458,144, filed on Dec. 9, 1999, now abandoned, and a continuation-in-part of application No. 09/458,477, filed on Dec. 9, 1999, now abandoned, and a continuation-in-part of application No. 09/457,556, filed on Dec. 9, 1999, now abandoned, and a continuation-in-part of application No. 09/444,341, filed on Nov. 19, 1999, now abandoned, and a continuation-in-part of application No. 09/444,338, filed on Nov. 19, 1999, now abandoned, and a continuation-in-part of application No. 09/418,922, filed on Oct. 15, 1999, now abandoned, and a continuation-in-part of application No. 09/418,917, filed on Oct. 15, 1999, now abandoned, which is a continuation-in-part of application No. 09/418,529, filed on Oct. 14, 1999, now abandoned.

(60) Provisional application No. 60/211,627, filed on Jun. 14, 2000, provisional application No. 60/211,687, filed on Jun. 14, 2000, provisional application No. 60/211,609, filed on Jun. 14, 2000, provisional application No. 60/211,626, filed on Jun. 14, 2000, provisional application No. 60/211,880, filed on Jun. 14, 2000, provisional application No. 60/211,607, filed on Jun. 14, 2000, provisional application No. 60/211,766, filed on Jun. 14, 2000, provisional application No. 60/211,888, filed on Jun. 14, 2000, provisional application No. 60/212,070, filed on Jun. 14, 2000.

(51) Int. Cl.
*C12P 21/06*    (2006.01)

(52) U.S. Cl. .................... 435/69.1; 435/6; 435/320.1; 435/252; 435/325; 435/7.1; 530/350

(58) Field of Classification Search ...................... None
See application file for complete search history.

(56) References Cited

U.S. PATENT DOCUMENTS

| | | | |
|---|---|---|---|
| 5,491,084 A | 2/1996 | Chalfie et al. |
| 5,874,304 A | 2/1999 | Zolotukhin et al. |
| 5,919,445 A | 7/1999 | Chao |
| 5,958,713 A | 9/1999 | Thastrup et al. |
| 5,968,738 A | 10/1999 | Anderson et al. |
| 5,968,750 A | 10/1999 | Zolotukhin et al. |

(Continued)

FOREIGN PATENT DOCUMENTS

DE        197 18        5/1997

(Continued)

OTHER PUBLICATIONS

Anderluh et al., Biochemical and Biophysical Research Communications (1996) 220:437-442.

(Continued)

*Primary Examiner*—Hope Robinson
(74) *Attorney, Agent, or Firm*—Bret E. Field; Bozocevic, Field & Francis LLP

(57) ABSTRACT

Nucleic acid compositions encoding novel chromo/fluoroproteins and mutants thereof, are provided. The subject proteins of interest are proteins that are colored and/or fluorescent, where this feature arises from the interaction of two or more residues of the protein. The subject proteins are further characterized in that they are either obtained from non-bioluminescent Cnidarian, e.g., Anthozoan, species or are obtained from non-Pennatulacean (sea pen) species. Specific proteins of interest include proteins obtained from the following specific Anthozoan species: *Anemonia majano* (NFP-1), *Clavularia* sp. (NFP-2), *Zoanthus* sp. (NFP-3 & NFP-4), *Discosoma striata* (NFP-5), *Discosoma* sp. "red" (NFP-6), *Anemonia sulcata* (NFP-7), *Discosoma* sp. "green" (NFP-8), and *Discosoma* sp. "magenta" (NFP-9). Also of interest are proteins that are substantially similar to, or mutants of, the above specific proteins. Also provided are fragments of the nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

20 Claims, 19 Drawing Sheets

U.S. PATENT DOCUMENTS

| | | | |
|---|---|---|---|
| 5,976,796 | A | 11/1999 | Szalay et al. |
| 5,985,577 | A | 11/1999 | Bulinski |
| 6,020,192 | A | 2/2000 | Muzyczka et al. |
| 6,066,476 | A | 5/2000 | Tsien et al. |
| 6,342,379 | B1 | 1/2002 | Tsien et al. |

FOREIGN PATENT DOCUMENTS

| | | |
|---|---|---|
| WO | WO 99/49019 | 9/1999 |
| WO | WO 00/34318 | 12/1999 |
| WO | WO 00/34319 | 12/1999 |
| WO | WO 00/34320 | 12/1999 |
| WO | WO 00/34321 | 12/1999 |
| WO | WO 00/34322 | 12/1999 |
| WO | WO 00/34323 | 12/1999 |
| WO | WO 00/34324 | 12/1999 |
| WO | WO 00/34325 | 12/1999 |
| WO | WO 00/34326 | 12/1999 |
| WO | WO 00/34526 | 12/1999 |
| WO | WO 00/46233 | 8/2000 |
| WO | WO 01/27150 | 10/2000 |
| WO | WO 01/32688 | 5/2001 |
| WO | WO 01/34824 | 5/2001 |

OTHER PUBLICATIONS

Baird et al. "Biochemistry, Mutagenesis and Oligomerization of DsRed, a Red Fluorescent Protein from Coral," PNAS (2000) 97(22):11984-11989.
Dove et al., Biological Bulletin (1995) 189:288-297.
Fradkov et al., FEBS Lett. (2000) 479(3):127-30.
Gurskaya et al., FEBS Lett., (2001) 507(1):16-20.
Gurskaya et al., BMC Biochem. (2001) 2:6.
Haas et al. "Codon Usage Limitation in the Expression of HIV-1 Envelope Glycoprotein," Current Biology (1996) 6(3):315-324.
Heim et al. PNAS (1994) 91:12501-04.
Lukyanov, K., et al (2000) J Biol Chemistry 275(34):25879-25882.
Macek et al., Eur. J. Biochem. (1995) 234:329-335.
Martynov et al., J Biol Chem. (2001) 276:21012-6.
Matz, M.V., et al. (1999) *Nature Biotechnol.* 17:969-973.
Terskikh et al., Science (2000) 290:1585-8.
Tsien, Annual Rev. of Biochemistry (1998) 67:509-544.
Tsien, Nat. Biotech. (1999) 17:956-957.
Wall et al. "The Structural Basis for Red Fluorescence in the Tetrameric GFP Homolog DsRed," Nature Structural Biology (2000) 7(12):1133-1138.
Ward et al., J. Biol. Chem. (1979) 254:781-788.
Wells, Biochemistry (1990) 29:8509-8517.
Wiedenmann et al. "Cracks in the β-Can: Fluorescent Proteins from Anemonia Sulcata (Anthozoa, Actinaria)" PNAS (2000) 97(26):14091-14096.
Wiedermann et al., Jahrestagung der Deutschen Gesellschact furTropenokologie-gto. Ulm. Feb. 17-19, 1999. Poster P-4.20.
Wiehler et al. "Mutants of Discosoma Red Fluorescent Protein with a GFP-Like Chromophore," FEBS Letter (2001) 487:384-389.
Wetzel "Mutations and Off-Pathway Aggregation of Proteins," Tibtech (1994) 12:193-198.
Yang et al. "Optimized Codon Usage and Chromophore Mutations Provide Enhanced Sensitivity with the Green Fluorescent Protein," 24(22):4592-4593.
Yarbrough et al., Proc Natl Acad Sci U S A (2001) 98:462-7.

FIGURE 1 cDNA sequence of wild type amFP486
ATGGCTCTTTCAAACAAGTTTATCGGAGATGACATGAAAATGACCTACCATATGGATG
GCTGTGTCAATGGGCATTACTTTACCGTCAAAGGTGAAGGCAACGGGAAGCCATACGA
AGGGACGCAGACCTCGACTTTTAAAGTCACCATGGCCAACGGTGGGCCCCTTGCATTC
TCCTTTGACATACTATCTACAGTGTTCAAGTATGGAAATCGATGCTTTACTGCGTATC
CTACCAGTATGCCCGACTATTTCAAACAAGCATTTCCTGACGGAATGTCATATGAAAG
GACTTTTACCTATGAAGATGGAGGAGTTGCTACAGCCAGTTGGGAAATAAGCCTTAAA
GGCAACTGCTTTGAGCACAAATCCACGTTTCATGGAGTGAACTTTCCTGCTGATGGAC
CTGTGATGGCGAAGATGACAACTGGTTGGGACCCATCTTTTGAGAAAATGACTGTCTG
CGATGGAATATTGAAGGGTGATGTCACCGCGTTCCTCATGCTGCAAGGAGGTGGCAAT
TACAGATGCCAATTCCACACTTCTTACAAGACAAAAAAACCGGTGACGATGCCACCAA
ACCATGCGGTGGAACATCGCATTGCGAGGACCGACCTTGACAAAGGTGGCAACAGTGT
TCAGCTGACGGAGCACGCTGTTGCACATATAACCTCTGTTGTCCCTTTC (SEQ ID
NO:01)

amino acid sequence of wild type amFP486

MALSNKFIGD DMKMTYHMDG CVNGHYFTVK GEGNGKPYEG TQTSTFKVTM ANGGPLAFSF
DILSTVFKYG NRCFTAYPTS MPDYFKQAFP DGMSYERTFT YEDGGVATAS WEISLKGNCF
EHKSTFHGVN FPADGPVMAK MTTGWDPSFE KMTVCDGILK GDVTAFLMLQ GGGNYRCQFH
TSYKTKKPVT MPPNHAVEHR IARTDLDKGG NSVQLTEHAV AHITSVVPF
    (SEQ ID NO:02)

Figure 2 cDNA sequence of wild type cFP484

```
TATAGGANCATNNGGGNGATTGGGGTCCAAAGCATTGTAACCAACGCAGATAACCCCCAG
TGGTNTCAAACGCAGANAACGCGGGAACATTGGAAAATTGANTNTTAAGGAGGCAAGGAA
TCGGGAGTAAAGTTGCGAGAAACTGAAAAAATGAAGTGTAAATTTGTGTTCTGCCTGTCC
TTCTTGGTCCTCGCCATCACAAACGCGAACATTTTTTGAGAAACGAGGCTGACTTAGAA
GAGAAGACATTGAGAATACCAAAAGCTCTAACCACCATGGGTGTGATTAAACCAGACATG
AAGATTAAGCTGAAGATGGAAGGAAATGTAAACGGGCATGCTTTTGTGATCGAAGGAGAA
GGAGAAGGAAAGCCTTACGATGGGACACACACTTTAAACCTGGAAGTGAAGGAAGGTGCG
CCTCTGCCTTTTTCTTACGATATCTTGTCAAACGCGTTCCAGTACGGAAACAGAGCATTG
ACAAAATACCCAGACGATATAGCAGACTATTTCAAGCAGTCGTTTCCCGAGGGATATTCC
TGGGAAAGAACCATGACTTTTGAAGACAAAGGCATTGTCAAAGTGAAAAGTGACATAAGC
ATGGAGGAAGACTCCTTTATCTATGAAATTCGTTTGATGGGATGAACTTTCCTCCCAAT
GGTCCGGTTATGCAGAAAAAAACTTTGAAGTGGGAACCATCCACTGAGATTATGTACGTG
CGTGATGGAGTGCTGGTCGGAGATATTAGCCATTCTCTGTTGCTGGAGGGAGGTGGCCAT
TACCGATGTGACTTCAAAAGTATTTACAAAGCAAAAAAAGTTGTCAAATTGCCAGACTAT
CACTTTGTGGACCATCGCATTGAGATCTTGAACCATGACAAGGATTACAACAAAGTAACG
CTGTATGAGAATGCAGTTGCTCGCTATTCTTTGCTGCCAAGTCAGGCCTAGACAACAAGG
ATACTGAAAACATATTTGTCTGAGGGTTTGTGTTGTTTTTAAAAGACATCAGCTCAGCA
TTCGTTAGTTGTAACAAAAAATAGCTTTAATTTTTGGTGGGATTAAATCATAGGGATTTG
TTTTAGTAATCATTTTGCTTAATAAAAAGTGCCTTG  (SEQ ID NO:03)
``` amino acid sequence of wild type cFP484

```
M  K  C  K  F  V  F  C  L  S
F  L  V  L  A  I  T  N  A  N  I  F  L  R  N  E  A  D  L  E
E  K  T  L  R  I  P  K  A  L  T  T  M  G  V  I  K  P  D  M
K  I  K  L  K  M  E  G  N  V  N  G  H  A  F  V  I  E  G  E
G  E  G  K  P  Y  D  G  T  H  T  L  N  L  E  V  K  E  G  A
P  L  P  F  S  Y  D  I  L  S  N  A  F  Q  Y  G  N  R  A  L
T  K  Y  P  D  D  I  A  D  Y  F  K  Q  S  F  P  E  G  Y  S
W  E  R  T  M  T  F  E  D  K  G  I  V  K  V  K  S  D  I  S
M  E  E  D  S  F  I  Y  E  I  R  F  D  G  M  N  F  P  P  N
G  P  V  M  Q  K  K  T  L  K  W  E  P  S  T  E  I  M  Y  V
R  D  G  V  L  V  G  D  I  S  H  S  L  L  E  G  G  G  H
Y  R  C  D  F  K  S  I  Y  K  A  K  K  V  V  K  L  P  D  Y
H  F  V  D  H  R  I  E  I  L  N  H  D  K  D  Y  N  K  V  T
L  Y  E  N  A  V  A  R  Y  S  L  L  P  S  Q  A    (SEQ ID NO:04)
```

Figure 3 cDNA sequence of zFP506
ATGGCTCAGTCAAAGCACGGTCTAACAAAAGAAATGACAATGAAATACCGTATGGAAGGGTGC
GTCGATGGACATAAATTTGTGATCACGGGAGAGGGCATTGGATATCCGTTCAAAGGGAAACAG
GCTATTAATCTGTGTGTGGTCGAAGGTGGACCATTGCCATTTGCCGAAGACATATTGTCAGCT
GCCTTTATGTACGGAAACAGGGTTTTCACTGAATATCCTCAAGACATAGCTGACTATTTCAAG
AACTCGTGTCCTGCTGGTTATACATGGGACAGGTCTTTTCTCTTTGAGGATGGAGCAGTTTGC
ATATGTAATGCAGATATAACAGTGAGTGTTGAAGAAAACTGCATGTATCATGAGTCCAAATTT
TATGGAGTGAATTTTCCTGCTGATGGACCTGTGATGAAAAAGATGACAGATAACTGGGAGCCA
TCCTGCGAGAAGATCATACCAGTACCTAAGCAGGGGATATTGAAGGGGATGTCTCCATGTAC
CTCCTTCTGAAGGATGGTGGGCGTTTACGGTGCCAATTCGACACAGTTTACAAAGCAAAGTCT
GTGCCAAGAAAGATGCCGGACTGGCACTTCATCCAGCATAAGCTCACCCGTGAAGACCGCAGC
GATGCTAAGAATCAGAAATGGCATCTGACAGAACATGCTATTGCATCCGGATCTGCATTGCCC
(SEQ ID NO:05)

amino acid sequence of zFP506
MAQSKHGLTK EMTMKYRMEG CVDGHKFVIT GEGIGYPFKG KQAINLCVVE GGPLPFAEDI LSAAFNYGNR VFTEYPQDIA
DYFKNSCPAG YTWDRSFLFE DGAVCICNAD ITVSVEENCM YHESKFYGVN FPADGPVMKK MTDNWEPSCE KIIPVPKQGI
LKGDVSMYLL LKDGGRLRCQ FDTVYKAKSV PRKMPDWHFI QHKLTREDRS DAKNQKWHLT EHAIASGSAL P
(SEQ ID NO:06)

Figure 4 cDNA sequence of zFP538
```
gagttgagtt tctcgacttc agttgtatca attttggggc atcaagcgat ctattttcaa
catggctcat tcaaagtacg gtctaaaaga agaaatgaca atgaaatacc acatggaagg
gtgcgtcaac ggacataaat ttgtgatcac gggcgaaggc attggatatc cgttcaaagg
gaaacagact attaatctgt gtgtgatcga agggggacca ttgccatttt ccgaagacat
attgtcagct ggctttaagt acggagacag gattttcact gaatatcctc aagacatagt
agactatttc aagaactcgt gtcctgctgg atatacatgg ggcaggtctt ttctctttga
ggatggagca gtctgcatat gcaatgtaga tataacagtg agtgtcaaag aaaactgcat
ttatcataag agcatattta atggaatgaa ttttcctgct gatggacctg tgatgaaaaa
gatgacaact aactgggaag catcctgcga gaagatcatg ccagtaccta agcagggat
actgaaaggg gatgtctcca tgtacctcct tctgaaggat ggtgggcgtt accggtgcca
gttcgacaca gtttacaaag caaagtctgt gccaagtaag atgccggagt ggcacttcat
ccagcataag ctcctccgtg aagaccgcag cgatgctaag aatcagaagt ggcagctgac
agagcatgct attgcattcc cttctgcctt ggcctgataa gaatgtagtt ccaacatttt
aatgcatgtg cttgtcaatt attctgataa aaatgtagtt gagttgaaaa cagacaagta
caaataaagc acatgtaaat cgtct           (SEQ ID NO:07)
``` amino acid sequence of zFP538
```
Met Ala His Ser Lys His Gly Leu Lys Glu Glu Met Thr Met Lys
Tyr His Met Glu Gly Cys Val Asn Gly His Lys Phe Val Ile Thr
Gly Glu Gly Ile Gly Tyr Pro Phe Lys Gly Lys Gln Thr Ile Asn
Leu Cys Val Ile Glu Gly Gly Pro Leu Pro Phe Ser Glu Asp Ile
Leu Ser Ala Gly Phe Lys Tyr Gly Asp Arg Ile Phe Thr Glu Tyr
Pro Gln Asp Ile Val Asp Tyr Phe Lys Asn Ser Cys Pro Ala Gly
Tyr Thr Trp Gly Ser Phe Leu Phe Glu Asp Gly Ala Val Cys Ile
Cys Asn Val Asp Ile Thr Val Ser Val Lys Glu Asn Cys Ile Tyr
His Lys Ser Ile Phe Asn Gly Met Asn Phe Pro Ala Asp Gly Pro
Val Met Lys Lys Met Thr Thr Asn Trp Glu Ala Ser Cys Glu Lys
Ile Met Pro Val Pro Lys Gln Gly Ile Leu Lys Gly Asp Val Ser
Met Tyr Leu Leu Leu Lys Asp Gly Gly Arg Tyr Arg Cys Gln Phe
Asp Thr Val Tyr Lys Ala Lys Ser Val Pro Ser Lys Met Pro Glu
Trp His Phe Ile Gln His Lys Leu Leu Arg Glu Asp Arg Ser Asp
Ala Lys Asn Gln Lys Trp Gln Leu Thr Glu His Ala Ile Ala Phe
Pro Ser Ala Leu Ala   (SEQ ID NO:08)
```

FIGURE 5 cDNA sequence of dsFP483

ACGGTCAGGGACACGGTGACCCACTTTGGTATTCTAACAAAATGAGTTGGTCCAAGAGTG
TGATCAAGGAAGAAATGTTGATCGATCTTCATCTGGAAGGAACGTTCAATGGGCACTACT
TTGAAATAAAAGGCAAAGGAAAAGGGAAGCCTAATGAAGGCACCAATACCGTCACGCTCG
AGGTTACCAAGGGTGGACCTCTGCCATTTGGTTGGCATATTTTGTGCCCACAATTTCAGT
ATGGAAACAAGGCATTTGTCCACCACCCTGACGACATACCTGATTATCTAAAGCTGTCAT
TTCCGGAGGGATATACATGGGAACGGTCCATGCACTTTGAAGACGGTGGCTTGTGTTGTA
TCACCAATGATATCAGTTTGACAGGCAACTGTTTCAACTACGACATCAAGTTCACTGGCT
TGAACTTTCCTCCAAATGGACCCGTTGTGCAGAAGAAGACAACTGGCTGGGAACCGAGCA
CTGAGCGTTTGTATCCTCGTGATGGCGTGTTGATAGGAGACATCCATCATGCTCTCACAG
TGGAAGGAGGTGGTCATTACGTATGTGACATTAAAACTGTTTACAGGGCCAAGAAGCCCG
TAAAGATGCCAGGGTATCACTATGTTGACACCAAACTGGTTATAAGGAGCAACGACAAAG
AATTCATGAAAGTTGAGGAGCATGAAATCGCCGTTGCACGCCACCATCCGCTCCAAAGCC
AATGAAGCTTAAGTAAAGCAAAAAGGTGACGAGGCATGATAGTATGACATGATAGTATGA
CATGATAGTATGACATGATAGTAAGAATTGTAAGCAAAAGGCTTTGCTTATTAAACTTGT
AATTGAAAAC (SEQ ID NO:09)

amino acid sequence of dsFP483

```
M S W S K S V
I K E E M L I D L H L E G T F N G H Y F
E I K G K G K G K P N E G T N T V T L E
V T K G G P L P F G W H I L C P Q F Q Y
G N K A F V H H P D D I P D Y L K L S F
P E G Y T W E R S M H F E D G G L C C I
T N D I S L T G N C F N Y D I K F T G L
N F P P N G P V V Q K K T G W E P S T
E R L Y P R D G V L I G D I H H A L T V
E G G H Y V C D I K T V Y R A K K P V
K M P G Y H Y V D T K L V I R S N D K E
F M K V E E H E I A V A R H H P L Q S Q
```
(SEQ ID NO:10)

FIGURE 6 cDNA sequence of drFP583

ATGAGGTCTTCCAAGAATGTTATCAAGGAGTTCATGAGGTTTAAGGTTCGCATGGAAGGAACGGTCAATGGGCACGAGT
TTGAAATAGAAGGCGAAGGAGAGGGGAGGCCATACGAAGGCCACAATACCGTAAAGCTTAAGGTAACCAAGGGGGGACC
TTTGCCATTTGCTTGGGATATTTTGTCACCACAATTTCAGTATGGAAGCAAGGTATATGTCAAGCACCCTGCCGACATA
CCAGACTATAAAAAGCTGTCATTTCCTGAAGGATTTAAATGGGAAAGGGTCATGAACTTTGAAGACGGTGGCGTCGTTA
CTGTAACCCAGGATTCCAGTTTGCAGGATGGCTGTTTCATCTACAAGGTCAAGTTCATTGGCGTGAACTTTCCTTCCGA
TGGACCTGTTATGCAAAAGAAGACAATGGGCTGGGAAGCCAGCACTGAGCGTTTGTATCCTCGTGATGGCGTGTTGAAA
GGAGAGATTCATAAGGCTCTGAAGCTGAAAGACGGTGGTCATTACCTAGTTGAATTCAAAAGTATTTACATGGCAAAGA
AGCCTGTGCAGCTACCAGGGTACTACTATGTTGACTCCAAACTGGATATAACAAGCCACAACGAAGACTATACAATCGT
TGAGCAGTATGAAAGAACCGAGGGACGCCACCATCTGTTCCTTTAA      (SEQ ID NO:11)

cDNA sequence of drFP583.1

GTCCTCCCAAGCAGTGGTATCAACGCAGAGTACGGGGGAGTTTCAGCCAGTGACGGT
CAGTGACAGGGTGAGCCACTTGGTATACCAACAAAATGAGGTCTTCCAAGAATGTTA
TCAAGGAGTTCATGAGGTTTAAGGTTCGCATGGAAGGAACGGTCAATGGGCACGAGT
TTGAAATAGAAGGCGAAGGAGAGGGGAGGCCATACGAAGGCCACAATACCGTAAAGC
TTAAGGTAACCAAGGGGGGACCTTTGCCATTTGCTTGGGATATTTTGTCACCACAAT
TTCAGTATGGAAGCAAGGTATATGTCAAGCACCCTGCCGACATACCAGACTATAAAA
AGCTGTCATTTCCTGAAGGATTTAAATGGGAAAGGGTCATGAACTTTGAAGACGGTG
GCGTCGTTACTGTAACCCAGGATTCCAGTTTGCAGGATGGCTGTTTCATCTACAAGT
CAAGTTCATTGGCGTTGAACTTTCCTTCCGATGGACCTGTTATGCAAAAGAAGACAA
TGGGCTGGGAAGCCAGCACTGAGCGTTTGTATCCTCGTGATGGCGTGTTGAAAGGAG
AGATTCATAAGGCTCTGAAGCTGAAAGACGGTGGTCATTACCTAGTTGAATTCAAAA
GTATTTACATGGCAAAGAAGCCTGTGCAGCTACCAGGGTACTACTATGTTGACTCCA
AACTGGATATAACAAGCCACAACGAAGACTATACAATCGTTGAGCAGTATGAAAGAA
CCGAGGGACGCCACCATCTGTTCCTTTAAGGCTGAACTTGGCTCAGACGTGGGTGAG
CGGTAATGACCACAAAAGGCAGCGAAGAAAAACCATGATCGTTTTTTTTAGGTTGGC
AGCCTGAAATCGTAGGAAATACATCAGAAATGTTACAAACAGG (SEQ ID NO:45)

amino acid sequence of drFP583

MRSSKNVIKEFMRFKVRMEGTVNGHEFEIEGEGEGRPYEGHNTVKLKVTKGGPLPFAWDILSPQFQ
YGSKVYVKHPADIPDYKKLSFPEGFKWERVMNFEDGGVVTVTQDSSLQDGCFIYKVKFIGVNFPSD
GPVMQKKTMGWEASTERLYPRDGVLKGEIHKALKLKDGGHYLVEFKSIYMAKKPVQLPGYYYVDSK
LDITSHNEDYTIVEQYERTEGRHHLFL SEQ ID NO:012)

amino acid sequence of drFP583.1

Met Arg Ser Ser Lys Asn Val Ile Lys Glu Phe Met Arg Phe Lys
Val Arg Met Glu Gly Thr Val Asn Gly His Glu Phe Glu Ile Glu
Gly Glu Gly Glu Gly Arg Pro Tyr Glu Gly His Asn Thr Val Lys
Leu Lys Val Thr Lys Gly Gly Pro Leu Pro Phe Ala Trp Asp Ile
Leu Ser Pro Gln Phe Gln Tyr Gly Ser Lys Val Tyr Val Lys His
Pro Ala Asp Ile Pro Asp Tyr Lys Lys Leu Ser Phe Pro Glu Gly
Phe Lys Trp Glu Arg Val Met Asn Phe Glu Asp Gly Gly Val Val
Thr Val Thr Gln Asp Ser Ser Leu Gln Asp Gly Cys Phe Ile Tyr
Lys Ser Ser Leu Ala Leu Asn Phe Pro Ser Asp Gly Pro Val
Met Gln Lys Lys Thr Met Gly Trp Glu Ala Ser Thr Glu Arg Leu
Gly His Tyr Leu Val Glu Phe Lys Ser Ile Ile Met Ala Lys Lys
Pro Val Gln Leu Pro Gly Tyr Tyr Tyr Val Asp Ser Lys Leu Asp
Ile Thr Ser His Asn Glu Asp Tyr Thr Ile Val Glu Gln Tyr Glu
Arg Ser Glu Gly Arg His His Leu Phe Leu
(SEQ ID NO:46)

FIGURE 7

Amino Acid and Nucleotide Sequence for asFP600

ATGGCTTCCTTTTTAAAGAAGACTATGCCCTTTAAGACGACCATTGAAGGGACGGTTAATGGCCAC
TACTTCAAGTGTACAGGAAAAGGAGAGGGCAACCCATTTGAGGGTACGCAGGAAATGAAGATAGAG
GTCATCGAAGGAGGTCCATTGCCATTTGCCTTCCACATTTTGTCAACGAGTTGTATGTACGGTAGT
AAGGCCTTCATCAAGTATGTGTCAGGAATTCCTGACTACTTCAAGCAGTCTTTCCCTGAAGGTTTT
ACTTGGGAAAGAACCACAACCTACGAGGATGGAGGCTTTCTTACAGCTCATCAGGACACAAGCCTA
GATGGAGATTGCCTCGTTTACAAGGTCAAGATTCTTGGTAATAATTTTCCTGCTGATGGCCCCGTG
ATGCAGAACAAAGCAGGAAGATGGGAGCCATCCACCGAGATAGTTTATGAAGTTGACGGTGTCCTG
CGTGGACAGTCTTTGATGGCCCTTAAGTGCCCTGGTGGTCGTCATCTGACTTGCCATCTCCATACT
ACTTACAGGTCCAAAAAACCAGCTGCTGCCTTGAAGATGCCAGGATTTCATTTTGAAGATCATCGC
ATCGAGATAATGGAGGAAGTTGAGAAAGGCAAGTGCTATAAACAGTACGAAGCAGCAGTGGGCAGG
TACTGTGATGCTGCTCCATCCAAGCTTGGACATAAC (SEQ ID NO:13)

Amino acid

MASFLKKTMP FKTTIEGTVN GHYFKCTGKG EGNPFEGTQE MKIEVIEGGP LPFAFHILST
SCMYGSKTFI KYVSGIPDYF KQSFPEGFTW ERTTTYEDGG FLTAHQDTSL DGDCLVYKVK
ILGNNFPADG PVMQNKAGRW EPATEIVYEV DGVLRGQSLM ALKCPGGRHL TCHLHTTYRS
KKPAAALKMP GFHFEDHRIE IMEEVEKGKC YKQYEAAVGR YCDAAPSKLG HN (SEQ ID
NO:14)

Figure 8 cDNA sequence of dgFP512

```
attcacctcg gtgatttgta agagaaagga tcaccatcaa gagaagagct gtaaaagtta    60
atattttact gtacttctac cagcatgagt gcacttaaag aagaaatgaa aatcaacctt   120
acaatggaag gtgttgttaa cgggcttcca tttaagatcc gtggggatgg aaaaggcaaa   180
ccataccagg gatcacagga gttaaccttg acggtggtta aaggcgggcc tctgcctttc   240
tcttatgata ttctgacaac gatgtttcag tacggcaaca gggcattcgt aaactaccca   300
gaggacatac cagatatttt caagcagacc tgttctggtc ctaatggtgg atattcctgg   360
caaaggacca tgacttatga agacggaggc gtttgcactg ctacaagcaa catcagcgtg   420
gttggcgaca ctttcaatta tgacattcac tttatgggag cgaattttcc tcttgatggt   480
ccagtgatgc agaaaagaac aatgaaatgg gaaccatcca ctgagataat gtttgaacgt   540
gatggaatgc tgagggtga cattgccatg tctctgttgc tgaagggagg gggccattac   600
cgatgtgatt ttgaaactat ttataaaccc aataaggttg tcaagatgcc agattaccat   660
tttgtggacc actgcattga gataacgagt caacaggatt attacaacgt ggttgagctg   720
accgaggttg ctgaagcccg ctactcttcg ctggagaaaa tcggcaaatc aaaggcgtaa   780
atccaagcaa tctaagaaaa caacaaggca ttaaaccgaa tcaccgtttt gaattttcg   840
ttcggaattt cttggtaaaa ctaggtttag aacgtttcat ttcgctggac ttctttgact   900
cagctgtaga caagaaaga          (SEQ ID NO:15)                         919
``` amino acid sequence of dgFP512

Met Ser Ala Leu Lys Glu Glu Met Lys Ile Asn Leu Thr Met Glu
Gly Val Val Asn Gly Leu Pro Phe Lys Ile Arg Gly Asp Gly Lys
Gly Lys Pro Tyr Gln Gly Ser Gln Glu Leu Thr Leu Thr Val Val
Lys Gly Gly Pro Leu Pro Phe Ser Tyr Asp Ile Leu Thr Thr Met
Phe Gln Tyr Gly Asn Arg Ala Phe Val Asn Tyr Pro Glu Asp Ile
Pro Asp Ile Phe Lys Gln Thr Cys Ser Gly Pro Asn Gly Gly Tyr
Ser Trp Gln Arg Thr Met Thr Tyr Glu Asp Gly Gly Val Cys Thr
Ala Thr Ser Asn Ile Ser Val Val Gly Asp Thr Phe Asn Tyr Asp
Ile His Phe Met Gly Ala Asn Phe Pro Leu Asp Gly Pro Val Met
Gln Lys Arg Thr Met Lys Trp Glu Pro Ser Thr Glu Ile Met Phe
Glu Arg Asp Gly Met Leu Arg Gly Asp Ile Ala Met Ser Leu Leu
Leu Lys Gly Gly Gly His Tyr Arg Cys Asp Phe Glu Thr Ile Tyr
Lys Pro Asn Lys Val Val Lys Met Pro Asp Tyr His Phe Val Asp
His Cys Ile Glu Ile Thr Ser Gln Gln Asp Tyr Tyr Asn Val Val
Glu Leu Thr Glu Val Ala Glu Ala Arg Tyr Ser Ser Leu Glu Lys
Ile Gly Lys Ser Lys Ala
(SEQ ID NO:16)

FIGURE 9 cDNA sequence of dmFP592

| | | | | | |
|---|---|---|---|---|---|
| agtttcagcc | agtgacaggg | tgagctgcca | ggtattctaa | caagatgagt | tgttccaaga | 60
| atgtgatcaa | ggagttcatg | aggttcaagg | ttcgtatgga | aggaacggtc | aatgggcacg | 120
| agtttgaaat | aaaaggcgaa | ggtgaaggga | ggccttacga | aggtcactgt | tccgtaaagc | 180
| ttatggtaac | caagggtgga | cctttgccat | ttgcttttga | tatttttgtca | ccacaatttc | 240
| agtatggaag | caaggtatat | gtcaaacacc | ctgccgacat | accagactat | aaaaagctgt | 300
| catttcctga | gggatttaaa | tgggaaaggg | tcatgaactt | tgaagacggt | ggcgtggtta | 360
| ctgtatccca | agattccagt | ttgaaagacg | gctgtttcat | ctacgaggtc | aagttcattg | 420
| gggtgaactt | tccttctgat | ggacctgtta | tgcagaggag | gacacggggc | tgggaagcca | 480
| gctctgagcg | tttgtatcct | cgtgatgggg | tgctgaaagg | agacatccat | atggctctga | 540
| ggctggaagg | aggcggccat | tacctcgttg | aattcaaaag | tatttacatg | gtaaagaagc | 600
| cttcagtgca | gttgccaggc | tactattatg | ttgactccaa | actggatatg | acgagccaca | 660
| acgaagatta | cacagtcgtt | gagcagtatg | aaaaaaccca | gggacgccac | catccgttca | 720
| ttaagcctct | gcagtgaact | cggctcagtc | atggattagc | ggtaatggcc | acaaaaggca | 780
| cgatgatcgt | tttttaggaa | tgcagccaaa | aattgaaggt | tatgacagta | gaaatacaag | 840
| caacaggctt | tgcttattaa | acatgtaatt | gaaaac | | | 876

(SEQ ID NO:17)

amino acid sequence of dmFP592

Met Ser Cys Ser Lys Asn Val Ile Lys Glu Phe Met Arg Phe Lys
Val Arg Met Glu Gly Thr Val Asn Gly His Glu Phe Glu Ile Lys
Gly Glu Gly Glu Gly Arg Pro Tyr Glu Gly His Cys Ser Val Lys
Leu Met Val Thr Lys Gly Gly Pro Leu Pro Phe Ala Phe Asp Ile
Leu Ser Pro Gln Phe Gln Tyr Gly Ser Lys Val Tyr Val Lys His
Pro Ala Asp Ile Pro Asp Tyr Lys Lys Leu Ser Phe Pro Glu Gly
Phe Lys Trp Glu Arg Val Met Asn Phe Glu Asp Gly Gly Val Val
Thr Val Ser Gln Asp Ser Ser Leu Lys Asp Gly Cys Phe Ile Tyr
Glu Val Lys Phe Ile Gly Val Asn Phe Pro Ser Asp Gly Pro Val
Met Gln Arg Arg Thr Arg Gly Trp Glu Ala Ser Ser Glu Arg Leu
Tyr Pro Arg Asp Gly Val Leu Lys Gly Asp Ile His Met Ala Leu
Arg Leu Glu Gly Gly Gly His Tyr Leu Val Glu Phe Lys Ser Ile
Tyr Met Val Lys Lys Pro Ser Val Gln Leu Pro Gly Tyr Tyr Tyr
Val Asp Ser Lys Leu Asp Met Thr Ser His Asn Glu Asp Tyr Thr
Val Val Glu Gln Tyr Glu Lys Thr Gln Gly Arg His His Pro Phe
Ile Lys Pro Leu Gln
(SEQ ID NO:18)

Figure 10

```
          M   A   L   S   N   E   F   I   G   D   D   M   K   M
676       ATG GCC CTG TCC AAC GAG TTC ATC GGC GAC GAC ATG AAG ATG
          TAC CGG GAC AGG TTG CTC AAG TAG CCG CTG CTG TAC TTC TAC
       T  Y   H   M   D   G   C   V   N   G   H   Y   F   T   V
721    ACC TAC CAC ATG GAC GGC TGC GTG AAC GGC CAC TAC TTC ACC GTG
       TGG ATG GTG TAC CTG CCG ACG CAC TTG CCG GTG ATG AAG TGG CAC
          K   G   E   G   S   G   K   P   Y   E   G   T   Q   T   S
766    AAG GGC GAG GGC AGC GGC AAG CCC TAC GAG GGC ACC CAG ACC TCC
       TTC CCG CTC CCG TCG CCG TTC GGG ATG CTC CCG TGG GTC TGG AGG
          T   F   K   V   T   M   A   N   G   G   P   L   A   F   S
811    ACC TTC AAG GTG ACC ATG GCC AAC GGC GGC CCC CTG GCC TTC TCC
       TGG AAG TTC CAC TGG TAC CGG TTG CCG CCG GGG GAC CGG AAG AGG
          F   D   I   L   S   T   V   F   M   Y   G   N   R   C   F
856    TTC GAC ATC CTG TCC ACC GTG TTC ATG TAC GGC AAC CGC TGC TTC
       AAG CTG TAG GAC AGG TGG CAC AAG TAC ATG CCG TTG GCG ACG AAG
          T   A   Y   P   T   S   M   P   D   Y   F   K   Q   A   F
901    ACC GCC TAC CCC ACC AGC ATG CCC GAC TAC TTC AAG CAG GCC TTC
       TGG CGG ATG GGG TGG TCG TAC GGG CTG ATG AAG TTC GTC CGG AAG
          P   D   G   M   S   Y   E   R   T   F   T   Y   E   D   G
946    CCC GAC GGC ATG TCC TAC GAG AGA ACC TTC ACC TAC GAG GAC GGC
       GGG CTG CCG TAC AGG ATG CTC TCT TGG AAG TGG ATG CTC CTG CCG
          G   V   A   T   A   S   W   E   I   S   L   K   G   N   C
991    GGC GTG GCC ACC GCC AGC TGG GAG ATC AGC CTG AAG GGC AAC TGC
       CCG CAC CGG TGG CGG TCG ACC CTC TAG TCG GAC TTC CCG TTG ACG
          F   E   H   K   S   T   F   H   G   V   N   F   P   A   D
1036   TTC GAG CAC AAG TCC ACC TTC CAC GGC GTG AAC TTC CCC GCC GAC
       AAG CTC GTG TTC AGG TGG AAG GTG CCG CAC TTG AAG GGG CGG CTG
          G   P   V   M   A   K   K   T   T   G   W   D   P   S   F
1081   GGC CCC GTG ATG GCC AAG AAG ACC ACC GGC TGG GAC CCC TCC TTC
       CCG GGG CAC TAC CGG TTC TTC TGG TGG CCG ACC CTG GGG AGG AAG
          E   K   M   T   V   C   D   G   I   L   K   G   D   V   T
1126   GAG AAG ATG ACC GTG TGC GAC GGC ATC TTG AAG GGC GAC GTG ACC
       CTC TTC TAC TGG CAC ACG CTG CCG TAG AAC TTC CCG CTG CAC TGG
          A   F   L   M   L   Q   G   G   G   N   Y   R   C   Q   F
1171   GCC TTC CTG ATG CTG CAG GGC GGC GGC AAC TAC AGA TGC CAG TTC
       CGG AAG GAC TAC GAC GTC CCG CCG CCG TTG ATG TCT ACG GTC AAG
          H   T   S   Y   K   T   K   K   P   V   T   M   P   P   N
1216   CAC ACC TCC TAC AAG ACC AAG AAG CCC GTG ACC ATG CCC CCC AAC
       GTG TGG AGG ATG TTC TGG TTC TTC GGG CAC TGG TAC GGG GGG TTG
          H   V   V   E   H   R   I   A   R   T   D   L   D   K   G
1261   CAC GTG GTG GAG CAC CGC ATC GCC AGA ACC GAC CTG GAC AAG GGC
       GTG CAC CAC CTC GTG GCG TAG CGG TCT TGG CTG GAC CTG TTC CCG
          G   N   S   V   Q   L   T   E   H   A   V   A   H   I   T
1306   GGC AAC AGC GTG CAG CTG ACC GAG CAC GCC GTG GCC CAC ATC ACC
       CCG TTG TCG CAC GTC GAC TGG CTC GTG CGG CAC CGG GTG TAG TGG
          S   V   V   P   F   *
1351   TCC GTG GTG CCC TTC TGA
       AGG CAC CAC GGG AAG ACT              (SEQ ID NO:27 & 28)
```

Figure 11
Non-aggregating mutant FP3-NA was generated from zFP506-N65M (non-humanized version). In comparison with zFP506-N65M, FP3-NA contains two additional amino acid substitutions - K5E and K10E. Also, one accidental nucleotide substitution was introduced due to PCR mistake (double underline).

Cloning into pQE30 was done using BamHI and HindIII sites:

```
GGA TCC GCT CAG TCA GAG CAC GGT CTA ACA GAA GAA ATG ACA ATG AAA
BamHI  A   Q   S   E   H   G   L   T   E   E   M   T   M   K

TAC CGT ATG GAA GGG TGC GTC GAT GGA CAT AAA TTT GTG ATC ACG GGA
 Y   R   M   E   G   C   V   D   G   H   K   F   V   I   T   G

GAG GGC ATT GGA TAT CCG TTC AAA GGG AAA CAG GCT ATT AAT CTG TGT
 E   G   I   G   Y   P   F   K   G   K   Q   A   I   N   L   C

GTG GTC GAA GGT GGA CCA TTG CCA TTT GCC GAA GAC ATA TTG TCA GCT
 V   V   E   G   G   P   L   P   F   A   E   D   I   L   S   A

GCC TTT ATG TAC GGA AAC AGG GTT TTC ACT GAA TAT CCT CAA GAC ATA
 A   F   M   Y   G   N   R   V   F   T   E   Y   P   Q   D   I

GTT GAC TAT TTC AAG AAC TCG TGT CCT GCT GGA TAT ACA TGG GAC AGG
 V   D   Y   F   K   N   S   C   P   A   G   Y   T   W   D   R

TCT TTT CTC TTT GAG GAT GGA GCA GTT TGC ATA TGT AAT GCA GAT ATA
 S   F   L   F   E   D   G   A   V   C   I   C   N   A   D   I

ACA GTG AGT GTT GAA GAA AAC TGC ATG TAT CAT GAG TCC AAA TTC TAT
 T   V   S   V   E   E   N   C   M   Y   H   E   S   K   F   Y

GGA GTG AAT TTT CCT GCT GAT GGA CCT GTG ATG AAA AAG ATG ACA GAT
 G   V   N   F   P   A   D   G   P   V   M   K   K   M   T   D

AAC TGG GAG CCA TCC TGC GAG AAG ATC ATA CCA GTA CCT AAG CAG GGG
 N   W   E   P   S   C   E   K   I   I   P   V   P   K   Q   G

ATA TTG AAA GGG GAT GTC TCC ATG TAC CTC CTT CTG AAG GAT GGT GGG
 I   L   K   G   D   V   S   M   Y   L   L   L   K   D   G   G

CGT TTA CGG TGC CAA TTC GAC ACA GTT TAC AAA GCA AAG TCT GTG CCA
 R   L   R   C   Q   F   D   T   V   Y   K   A   K   S   V   P

AGA AAG ATG CCG GAC TGG CAC TTC ATC CAG CAT AAG CTC ACC CGT GAA
 R   K   M   P   D   W   H   F   I   Q   H   K   L   T   R   E

GAC CGC AGC GAT GCT AAG AAT CAG AAA TGG CAT CTG ACA GAA CAT GCT
 D   R   S   D   A   K   N   Q   K   W   H   L   T   E   H   A

ATT GCA TCC GGA TCT GCA TTG CCC TGA AAGCTT
 I   A   S   G   S   A   L   P   *   HindIII    (SEQ ID NO:29 & 30)
```

Figure 12

Amino acid sequence of zFP506 Yellow mutant

MAQSKHGLTKEMTMKYRMEGCVDGHKFVITGEGIGYPFKGKQAINLCVVEGGPLPFAEDILSAGFKYGDRVFTEYPQDI
VDYFKNSCPAGYTWDRSFLFEDGAVCICNADITVSVEENCMYHESKFYGVNFPADGPVMKKMTDNWEPSCEKIIPVPKQ
GILKGDVSMYLLLKDGGRLRCQFDTVYKAKSVPRKMPDWHFIQHKLTREDRSDAKNQKWHLTEHAIASGSALP*
(SEQ ID NO:31)

Figure 13

Amino Acid Sequence of zFP506 Yellow/bright mutant

MAQSKHGLTKEMTMKYRMEGCVDGHKFVITGEGIGYPFKGKQAINLCVVEGGPLPFAEDILSAGFKYGDRVFTEYPQDI
VDYFKNSCPAGYTWNRSFLFEDGAVCICNADITVSVEENCVYHESKFYGVNFPADGPVMKKMTDNWEPSCEKIIPVPRQ
GILKGDVSMYLLLKDGGRLRCQFDTVYKAKSVPRKMPDWHFIQHKLTREDRSDAKNQKWHLTEHAIASGSALS*
(SEQ ID NO:32)

Figure 14

Non-aggregating mutant FP4-NA was generated from zFP538-M128V (humanized version). In comparison with zFP538-M128V, FP4-NA contains two additional amino acid substitutions - K5E and K9T. Also, two accidental nucleotide substitutions were introduced due to PCR mistakes (double underline).

Cloning into pQE30 was done using BamHI and HindIII sites:

```
GGA TCC GCC CAC AGC GAG CAC GGC CTG ACC GAG GAG ATG ACC ATG AAG
BamHI  A   H   S   E   H   G   L   T   E   E   M   T   M   K

TAC CAC ATG GAG GGC TGC GTG AAC GGC CAC AAG TTC GTG ATC ACC GGC
 Y   H   M   E   G   C   V   N   G   H   K   F   V   I   T   G

GAG GGC ATC GGC TAC CCC TTC AAG GGC AAG CAG ACC ATC AAC CTG TGC
 E   G   I   G   Y   P   F   K   G   K   Q   T   I   N   L   C

GTG ATC GAG GGC GGC CCC CTG CCC TTC AGC GAG GAC ATC CTG AGC GCC
 V   I   E   G   G   P   L   P   F   S   E   D   I   L   S   A

GGC TTC AAG TAC GGC GAC CGG ATC TTC ACC GAG TAC CCC CAG GAC ATC
 G   F   K   Y   G   D   R   I   F   T   E   Y   P   Q   D   I

GTG GAC TAC TTC AAG AAC AGC TGC CCC GCC GGC TAC ACC TGG GGC CGG
 V   D   Y   F   K   N   S   C   P   A   G   Y   T   W   G   R

AGC TTC CTG TTC GAG GAC GGC GCC GTG TGC ATC TGT AAC GTG GAC ATC
 S   F   L   F   E   D   G   A   V   C   I   C   N   V   D   I

ACC GTG AGC GTG AAG GAG AAC TGC ATC TAC CAC AAG AGC ATC TTC AAC
 T   V   S   V   K   E   N   C   I   Y   H   K   S   I   F   N

GGC GTG AAC TTC CCC GCC GAC GGC CCC GTG ATG AAG AAG ATG ACC ACC
 G   V   N   F   P   A   D   G   P   V   M   K   K   M   T   T

AAC TGG GAG GCC AGC TGC GAG AAG ATC ATG CCC GTG CCT AAG CAG GGC
 N   W   E   A   S   C   E   K   I   M   P   V   P   K   Q   G

ATC CTG AAG GGC GAC GTG AGC ATG TAC CTG CTG CTG AAG GAC GGC GGC
 I   L   K   G   D   V   S   M   Y   L   L   L   K   D   G   G

CGG TAC CGG TGC CAG TTC GAC ACC GTG TAC AAG GCC AAG AGC GTG CCC
 R   Y   R   C   Q   F   D   T   V   Y   K   A   K   S   V   P

AGC AAG ATG CCC GAG TGG CAC TTC ATC CAG CAC AAG CTG CTG CGG GAG
 S   K   M   P   E   W   H   F   I   Q   H   K   L   L   R   E

GAC CGG AGC GAC GCC AAG AAC CAG AAG TGG CAG CTG ACC GAG CAC GCC
 D   R   S   D   A   K   N   Q   K   W   Q   L   T   E   H   A

ATC GCC TTC CCC AGC GCC CTG GCC TGA AAGCTT
 I   A   F   P   S   A   L   A   *  HindIII     (SEQ ID NOS: 33-34)
```

Figure 15

All mutants are derived from drFP583 (called "pink" or FP6.) by random mutagenesis The mutants E57 and AG4 are derivative from E5

Mutant: E5 = V105A, S197T Phenotype: in *E.coli* seen as Green overnight, matures to Red over 24h at 37°C (final peaks ratio Red vs. Green is 75:25); folding is faster then FP6.

Mutant: E8 = N42H Phenotype: always has two peaks Green & Red in approx. 60:40; folding is faster than E5 (about 8h at 37°C)

Mutant: E83 = N42H, V71A, I180V Phenotype: always has two almost equal peaks Green & Red; folding is the same as for E8

Mutant: E5up = V105A Phenotype: seen as Red from the beginning; folding is faster than E5 (about 12-16h) Almost no Green peak at final point of maturation Mutant: E57 = V105A, I161T, S197A Phenotype: at common is like E5up but folding is more faster (no more that 8-10h) Very small Green peak at final point of maturation (less that 5%)

Mutant: E5down = S197T Phenotype and folding rate are exactly the same as for E5

Mutant: AG4 = V71M, V105A, S197T Phenotype: Very bright Green, no Red at all (even at the beginning); folding is faster than E5 (no more that 16h)

Mutant: AG4 = V71M, V105A, Y120H, S197T Phenotype: at common is like AG4, but more brighter (appox. twice) one.

```
  1 Met Arg Ser Ser Lys Asn Val Ile Lys Glu Phe Met Arg Phe Lys Val      16
  1 ATG CGC TCC TCC AAG AAC GTC ATC AAG GAG TTC ATG CGC TTC AAG GTG      48

17 Arg Met Glu Gly Thr Val Asn Gly His Glu Phe Glu Ile Glu Gly Glu      32
 49 CGC ATG GAG GGC ACC GTG AAC GGC CAC GAG TTC GAG ATC GAG GGC GAG      96
                                    His(CAC) for E8 and E83
 33 Gly Glu Gly Arg Pro Tyr Glu Gly His Asn Thr Val Lys Leu Lys Val      48
 97 GGC GAG GGC CGC CCC TAC GAG GGC CAC AAC ACC GTG AAG CTG AAG GTG     144

49 Thr Lys Gly Gly Pro Leu Pro Phe Ala Trp Asp Ile Leu Ser Pro Gln      64
145 ACC AAG GGC GGC CCC CTG CCC TTC GCC TGG GAC ATC CTG TCC CCC CAG     192
                       Met(ATG) for AG4 and AG45/Ala(GCG) for E83
 65 Phe Gln Tyr Gly Ser Lys Val Tyr Val Lys His Pro Ala Asp Ile Pro      80
193 TTC CAG TAC GGC TCC AAG GTG TAC GTG AAG CAC CCC GCC GAC ATC CCC     240

81 Asp Tyr Lys Lys Leu Ser Phe Pro Glu Gly Phe Lys Trp Glu Arg Val      96
241 GAC TAC AAG AAG CTG TCC TTC CCC GAG GGC TTC AAG TGG GAG CGC GTG     288
                               Ala(GCG)-for E5, E57, AG4 and AG45
 97 Met Asn Phe Glu Asp Gly Gly Val Val Thr Val Thr Gln Asp Ser Ser     112
289 ATG AAC TTC GAG GAC GGC GGC GTG GTG ACC GTG ACC CAG GAC TCC TCC     336
                         His(CAC)-for AG45
113 Leu Gln Asp Gly Cys Phe Ile Tyr Lys Val Lys Phe Ile Gly Val Asn     128
337 CTG CAG GAC GGC TGC TTC ATC TAC AAG GTG AAG TTC ATC GGC GTG AAC     384

129 Phe Pro Ser Asp Gly Pro Val Met Gln Lys Lys Thr Met Gly Trp Glu     144
385 TTC CCC TCC GAC GGC CCC GTG ATG CAG AAG AAG ACC ATG GGC TGG GAG     432

145 Ala Ser Thr Glu Arg Leu Tyr Pro Arg Asp Gly Val Leu Lys Gly Glu     160
433 GCC TCC ACC GAG CGC CTG TAC CCC CGC GAC GGC GTG CTG AAG GGC GAG     480
    Thr(ACC) for E57
161 Ile His Lys Ala Leu Lys Leu Lys Asp Gly Gly His Tyr Leu Val Glu     176
481 ATC CAC AAG GCC CTG AAG CTG AAG GAC GGC GGC CAC TAC CTG GTG GAG     528
               Val(GTC) for E83
177 Phe Lys Ser Ile Tyr Met Ala Lys Lys Pro Val Gln Leu Pro Gly Tyr     192
529 TTC AAG TCC ATC TAC ATG GCC AAG AAG CCC GTG CAG CTG CCC GGC TAC     576
                 Thr(ACC) for E5, AG4 and AG45/Ala(GCC) for E57
193 Tyr Tyr Val Asp Ser Lys Leu Asp Ile Thr Ser His Asn Glu Asp Tyr     208
577 TAC TAC GTG GAC TCC AAG CTG GAC ATC ACC TCC CAC AAC GAG GAC TAC     624

209 Thr Ile Val Glu Gln Tyr Glu Arg Thr Glu Gly Arg His His Leu Phe Leu *** 229
625 ACC ATC GTG GAG CAG TAC GAG CGC ACC GAG GGC CGC CAC CAC CTG TTC CTG TAA 678
(SEQ ID NO:11 & 12)
```

FIGURE 16

Nucleic acid sequence of humanized drFP583

ATGGTGCGCTCCTCCAAGAACGTCATCAAGGAGTTCATGCGCTTCAAGGTGCGCATGG
AGGGCACCGTGAACGGCCACGAGTTCGAGATCGAGGGCGAGGGCGAGGGCCGCCCC
TACGAGGGCCACAACACCGTGAAGCTGAAGGTGACCAAGGGCGGCCCCCTGCCCTTC
GCCTGGGACATCCTGTCCCCCCAGTTCCAGTACGGCTCCAAGGTGTACGTGAAGCACC
CCGCCGACATCCCCGACTACAAGAAGCTGTCCTTCCCCGAGGGCTTCAAGTGGGAGC
GCGTGATGAACTTCGAGGACGGCGGCGTGGTGACCGTGACCCAAGACTCCTCCTGC
AGGACGGCTGCTTCATCTACAAGGTGAAGTTCATCGGCGTGAACTTCCCCTCCGACGG
CCCCGTAATGCAGAAGAAGACCATGGGCTGGGAGGCCTCCACCGAGCGCCTGTACCC
CCGCGACGGCGTGCTGAAGGGCGAGATCCACAAGGCCCTGAAGCTGAAGGACGGCG
GCCACTACCTGGTGGAGTTCAAGTCCATCTACATGGCCAAGAAGCCCGTGCAGCTGCC
CGGCTACTACTACGTGGACTCCAAGCTGGACATCACCTCCCACAACGAGGACTACAC
CATCGTGGAGCAGTACGAGCGCACCGAGGGCCGCCACCACCTGTTCCTGTAG (SEQ ID
NO:35)

Figure 17

DNA sequence (ORF) of E5-NA

ATGGCCTCCTCCGAGAACGTCATCACCGAGTTCATGCGCTTCAAGGTGCGCATGGAGGGCACCGTGAACGGCCACGAGT
TCGAGATCGAGGGCGAGGGCGAGGGCCGCCCCTACGAGGGCCACAACACCGTGAAGTTGAAGGTGACCAAGGGCGGCCC
CCTGCCCTTCGCCTGGGACATCCTGTCCCCCCAGTTCCAGTACGGCTCCAAGGTGTACGTGAAGCACCCCGCCGACATC
CCCGACTACAAGAAGCTGTCCTTCCCCGAGGGCTTCAAGTGGGAGCGCGTGATGAACTTCGAGGACGGCGGCGTGGCGA
CCGTGACCCAGGACTCCTCCTGCAGGACGGCTGCTTCATCTACAAGGTGAAGTTCATCGGCGTGAACTTCCCCTCCGA
CGGCCCCGTGATGCAGAAGAAGACCATGGGCTGGGAGGCCTCCACCGAGCGCCTGTACCCCCGCGACGGCGTGCTGAAG
GGCGAGATCCACAAGGCCCTGAAGCTGAAGGACGGCGGCCACTACCTGGTGGAGTTCAAGTCCATCTACATGGCCAAGA
AGCCCGTGCAGCTGCCCGGCTACTACTACGTGGACACCAAGCTGGACATCACCTCCCACAACGAGGACTACACCATCGT
GGAGCAGTACGAGCGCACCGAGGGCCGCCACCACCTGTTCCTGTAA   (SEQ ID NO:36)

Figure 18

ATGGTGCGCT CCTCCAAGAA CGTCATCAAG GAGTTCATGC GCTTCAAGGT
GCGCATGGAGGGCACCGTGA ACGGCCACGA GTTCGAGATC GAGGGCGAGG GCGAGGGCCG
CCCCTACGAG GGCCACAACA CCGTGAAGCT GAAGGTGACC AAGGGCGGCC CCTGCCCTT
CGCCTGGGAC ATCCTGTCCC CCAGTTCCA GTACGGCTCC AAGGTGTACG TGAAGCACCC
CGCCGACATC CCCGACTACA AGAAGCTGTC CTTCCCCGAG GGCTTCAAGT GGGAGCGCGT
GATGAACTTCGAGGACGGCG GCGTGGCGAC CGTGACCCAA GACTCCTCC TGCAGGACGG
CTGCTTCATC TACAAGGTGA AGTTCATCGG CGTGAACTTC CCCTCCGACG GCCCCGTAAT
GCAGAAGAAG ACCATGGGCT GGGAGGCCTC CACCGAGCGC CTGTACCCCC GCGACGGCGT
GCTGAAGGGC GAGACCCACA AGGCCCTGAA GCTGAAGGAC GGCGGCCACT ACCTGGTGGA
GTTCAAGTCC ATCTACATGG CCAAGAAGCC CGTGCAGCTG CCCGGCTACT ACTACGTGGA
CGCCAAGCTG GACATCACCT CCCACAACGA GGACTACACC ATCGTGGAGC AGTACGAGCG
CACCGAGGGCCGCCACCACC TGTTCCTGTA G (SEQ ID NO:37)

Figure 19

Nucleic acid sequence FP6 (E57)-NA

ATGGCCTCCTCCGAGAACGTCATCACCGAGTTCATGCGCTTCAAGGTGCGCATGGAGGGCACCGTGA
ACGGCCACGAGTTCGAGATCGAGGGCGAGGGCGAGGGCCGCCCCTACGAGGGCCACAACACCGTG
AAGCTGAAGGTGACCAAGGGCGGCCCCCTGCCCTTCGCCTGGGACATCCTGTCCCCCCAGTTCCAGT
ACGGCTCCAAGGTGTACGTGAAGCACCCCGCCGACATCCCCGACTACAAGAAGCTGTCCTTCCCCGA
GGGCTTCAAGTGGGAGCGCGTGATGAACTTCGAGGACGGCGGCGTGGCGACCGTGACCCAGGACTC
CTCCCTGCAGGACGGCTGCTTCATCTACAAGGTGAAGTTCATCGGCGTGAACTTCCCCTCCGACGGC
CCCGTGATGCAGAAGAAGACCATGGGCTGGGAGGCCTCCACCGAGCGCCTGTACCCCGCGACGGC
GTGCTGAAGGGCGAGACCCACAAGGCCCTGAAGCTGAAGGACGGCGGCCACTACCTGGTGGAGTTC
AAGTCCATCTACATGGCCAAGAAGCCCGTGCAGCTGCCCGGCTACTACTACGTGGACGCCAAGCTGG
ACATCACCTCCCACAACGAGGACTACACCATCGTGGAGCAGTACGAGCGCACCGAGGGCCGCCACCA
CCTGTTCCTG (SEQ ID NO:38)

Figure 20

Non-aggregating mutant FP7-NA was generated from M35-5 (FP7a). In comparison with M35-5, FP7-NA contains two additional substitutions - K6T and K7E. Nucleotide substitutions in the codon for Leu-4 were introduced to optimize codon usage (double underline).

Cloning into pQE30 was done using BamHI and HindIII sites:

```
GGA TCC GCC TCC CTG CTG ACC GAG ACC ATG CCC TTC AGG ACC ACC ATC
BamHI  A   S   L   L   T   E   T   M   P   F   R   T   T   I

GAG GGC ACC GTG AAC GGC CAC TAC TTC AAG TGC ACC GGC AAG GGC GAG
 E   G   T   V   N   G   H   Y   F   K   C   T   G   K   G   E

GGC AAC CCC CTC GAG GGC ACC CAG GAG ATG AAG ATC GAG GTG ATC GAG
 G   N   P   L   E   G   T   Q   E   M   K   I   E   V   I   E

GGC GGC CCC CTG CCC TTC GCC TTC CAC ATC CTG TCC ACC TCC TGC ATG
 G   G   P   L   P   F   A   F   H   I   L   S   T   S   C   M

TAC GGC TCC AAG GCC TTC ATC AAG TAC GTG TCC GGC ATC CCC GAC TAC
 Y   G   S   K   A   F   I   K   Y   V   S   G   I   P   D   Y

TTC AAG CAG TCC CTC CCC GAG GGC TTC ACC TGG GAG CGC ACC ACC ACC
 F   K   Q   S   L   P   E   G   F   T   W   E   R   T   T   T

TAC GAG GAC GGC GGC TTC CTG ACC GCC CAC CAG GAC ACC TCC CTG GAC
 Y   E   D   G   G   F   L   T   A   H   Q   D   T   S   L   D

GGC GAC TGC CTG GTG TAC AAG GTG AAG ATC CTG GGC AAC AAC TTC CCC
 G   D   C   L   V   Y   K   V   K   I   L   G   N   N   F   P

GCC GAC GGC CCC GTG ATG CAG AAC AAG GCC GGC CGC TGG GAG CCC TCC
 A   D   G   P   V   M   Q   N   K   A   G   R   W   E   P   S

ACC GAG ATC GTG TAC GAG GTG GAC GGC GTG CTG CGC GGC CAG TCC CTG
 T   E   I   V   Y   E   V   D   G   V   L   R   G   Q   S   L

ATG GCC CTG GAG TGC CCC GGC GGT CGC CAC CTG ACC TGC CAC CTG CAC
 M   A   L   E   C   P   G   G   R   H   L   T   C   H   L   H

ACC ACC TAC CGC TCC AAG AAG CCC GCC TCC GCC CTG AAG ATG CCC GGC
 T   T   Y   R   S   K   K   P   A   S   A   L   K   M   P   G

TTC CAC TTC GAG GAC CAC CGC ATC GAG ATC CTG GAG GAG GTG GAG AAG
 F   H   F   E   D   H   R   I   E   I   L   E   E   V   E   K

GGC AAG TGC TAC AAG CAG TAC GAG GCC GCC GTG GGC CGC TAC TGC GAC
 G   K   C   Y   K   Q   Y   E   A   A   V   G   R   Y   C   D

GCC GCC CCC TCC AAG CTG GGC CAC AAC TGAAGCTT
 A   A   P   S   K   L   G   H   N   *   HindIII  (SEQ ID NO:39 & 40)
```

FIGURE 21

```
ATG GCC TCC TTC CTG AAG AAG ACC ATG CCC TTC AAG ACC ACC ATC GAG
 M   A   S   F   L   K   K   T   M   P   F   K   T   T   I   E

GGC ACC GTG AAC GGC CAC TAC TTC AAG TGC ACC GGC AAG GGC GAG GGC
 G   T   V   N   G   H   Y   F   K   C   T   G   K   G   E   G

AAC CCC TTC GAG GGC ACC CAG GAG ATG AAG ATC GAG GTG ATC GAG GGC
 N   P   F   E   G   T   Q   E   M   K   I   E   V   I   E   G

GGC CCC CTG CCC TTC GCC TTC CAC ATC CTG TCC ACC TCC TGC ATG TAC
 G   P   L   P   F   A   F   H   I   L   S   T   S   C   M   Y

GGC TCC AAG GCC TTC ATC AAG TAC GTG TCC GGC ATC CCC GAC TAC TTC
 G   S   K   A   F   I   K   Y   V   S   G   I   P   D   Y   F

AAG CAG TCC TTC CCC GAG GGC TTC ACC TGG GAG CGC ACC ACC ACC TAC
 K   Q   S   F   P   E   G   F   T   W   E   R   T   T   T   Y

GAG GAC GGC GGC TTC CTG ACC GCC CAC CAG GAC ACC TCC CTG GAC GGC
 E   D   G   G   F   L   T   A   H   Q   D   T   S   L   D   G

GAC TGC CTG GTG TAC AAG GTG AAG ATC CTG GGC AAC AAC TTC CCC GCC
 D   C   L   V   Y   K   V   K   I   L   G   N   N   F   P   A

GAC GGC CCC GTG ATG CAG AAC AAG GCC GGC CGC TGG GAG CCC TCC ACC
 D   G   P   V   M   Q   N   K   A   G   R   W   E   P   S   T

GAG ATC GTG TAC GAG GTG GAC GGC GTG CTG CGC GGC CAG TCC CTG ATG
 E   I   V   Y   E   V   D   G   V   L   R   G   Q   S   L   M

GCC CTG AAG TGC CCC GGC GGC CGC CAC CTG ACC TGC CAC CTG CAC ACC
 A   L   K   C   P   G   G   R   H   L   T   C   H   L   H   T

ACC TAC CGC TCC AAG AAG CCC GCC TCC GCC CTG AAG ATG CCC GGC TTC
 T   Y   R   S   K   K   P   A   S   A   L   K   M   P   G   F

CAC TTC GAG GAC CAC CGC ATC GAG ATC ATG GAG GAG GTG GAG AAG GGC
 H   F   E   D   H   R   I   E   I   M   E   E   V   E   K   G

AAG TGC TAC AAG CAG TAC GAG GCC GCC GTG GGC CGC TAC TGC GAC GCC
 K   C   Y   K   Q   Y   E   A   A   V   G   R   Y   C   D   A

GCC CCC TCC AAG CTG GGC CAC AAC TgA
 A   P   S   K   L   G   H   N   *    (SEQ ID NO:41 & 42)
```

Figure 22

Sequence of humanized 6/9 hybrid gene and 6/9-Q3 mutant

```
                                          for 6/9-2G and 6/9-Q3  CAG(Q)
  1   ATG AGC TGC AGC AAG AAC GTG ATC AAG GAG TTC ATG CGG TTC AAG GTG    48
  1    M   S   C   S   K   N   V   I   K   E   F   M   R   F   K   V    16

49   CGG ATG GAG GGC ACC GTG AAC GGC CAC GAG TTC GAG ATC AAG GGC GAG    96
 17    R   M   E   G   T   V   N   G   H   E   F   E   I   K   G   E    32

97   GGC GAG GGC CGG CCC TAC GAG GGC CAC TGC AGC GTG AAG CTC ATG GTG   144
 33    G   E   G   R   P   Y   E   G   H   C   S   V   K   L   M   V    48

145   ACC AAG GGC GGC CCC CTC CCC TTC GCC TTC GAC ATC CTC AGC CCC CAG   192
 49    T   K   G   G   P   L   P   F   A   F   D   I   L   S   P   Q    64

193   TTC CAG TAC GGC AGC AAG GTG TAC GTG AAG CAC CCC GCC GAC ATC CCC   240
 65    F   Q   Y   G   S   K   V   Y   V   K   H   P   A   D   I   P    80
                     ATG(M) for 6/9-Q3
241   GAC TAC AAG AAG CTC AGC TTC CCC GAG GGC TTC AAG TGG GAG CGG GTG   288
 81    D   Y   K   K   L   S   F   P   E   G   F   K   W   E   R   V    96

289   ATG AAC TTC GAG GAC GGC GGC GTG GTG ACC GTG AGC CAG GAC AGC AGC   336
 97    M   N   F   E   D   G   G   V   V   T   V   S   Q   D   S   S   112

337   CTC AAG GAC GGC TGC TTC ATC TAC GAG GTG AAG TTC ATC GGC GTG AAC   384
113    L   K   D   G   C   F   I   Y   E   V   K   F   I   G   V   N   128

385   TTC CCC AGC GAC GGC CCC GTG ATG CAG CGG CGG ACC CGG GGC TGG GAG   432
129    F   P   S   D   G   P   V   M   Q   R   R   T   R   G   W   E   144

433   GCC AGC AGC GAG CGG CTC TAC CCC CGG GAC GGC GTG CTC AAG GGC GAC   480
145    A   S   S   E   R   L   Y   P   R   D   G   V   L   K   G   D   160

481   ATC CAC ATG GCC CTC CGG CTC GAG GGC GGC GGC CAC TAC CTC GTG GAG   528
161    I   H   M   A   L   R   L   E   G   G   G   H   Y   L   V   E   176

529   TTC AAG AGC ATC TAC ATG GCC AAG AAG CCC GTG CAG CTC CCC GGC TAC   576
177    F   K   S   I   Y   M   A   K   K   P   V   Q   L   P   G   Y   192

577   TAC TAC GTG GAC AGC AAG CTC GAC ATC ACC AGC CAC AAC GAG GAC TAC   624
193    Y   Y   V   D   S   K   L   D   I   T   S   H   N   E   D   Y   208
                                          TCC(S) for 6/9-2G and 6/9-Q3
625   ACC ATC GTG GAG CAG TAC GAG CGG ACC GAG GGC CGG CAC CAC CTC TTC   672
209    T   I   V   E   Q   Y   E   R   T   E   G   R   H   H   L   F   224

673   CTC TGA                                                           678
225    L   *                                                            226
```

(SEQ ID NO:43 & 44)

SEQUENCE LISTING

```
<160> NUMBER OF SEQ ID NOS: 46

<210> SEQ ID NO 1
<211> LENGTH: 687
<212> TYPE: DNA
<213> ORGANISM: anemonia majano

<400> SEQUENCE: 1
atggctcttt caaacaagtt tatcggagat gacatgaaaa tgacctacca tatggatggc      60
tgtgtcaatg ggcattactt taccgtcaaa ggtgaaggca acgggaagcc atacgaaggg     120
acgcagacct cgacttttaa agtcaccatg gccaacggtg ggccccttgc attctccttt     180
gacatactat ctacagtgtt caagtatgga aatcgatgct ttactgcgta tcctaccagt     240
atgcccgact atttcaaaca agcatttcct gacggaatgt catatgaaag gacttttacc     300
tatgaagatg gaggagttgc tacagccagt tgggaaataa gccttaaagg caactgcttt     360
gagcacaaat ccacgtttca tggagtgaac tttcctgctg atggacctgt gatggcgaag     420
atgacaactg gttgggaccc atcttttgag aaaatgactg tctgcgatgg aatattgaag     480
ggtgatgtca ccgcgttcct catgctgcaa ggaggtggca attacagatg ccaattccac     540
acttcttaca agacaaaaaa accggtgacg atgccaccaa accatgcggt ggaacatcgc     600
```

```
attgcgagga ccgaccttga caaaggtggc aacagtgttc agctgacgga gcacgctgtt    660
gcacatataa cctctgttgt cccttc                                          687
```

<210> SEQ ID NO 2
<211> LENGTH: 229
<212> TYPE: PRT
<213> ORGANISM: anemonia majano

<400> SEQUENCE: 2

```
Met Ala Leu Ser Asn Lys Phe Ile Gly Asp Asp Met Lys Met Thr Tyr
  1               5                  10                  15
His Met Asp Gly Cys Val Asn Gly His Tyr Phe Thr Val Lys Gly Glu
                 20                  25                  30
Gly Asn Gly Lys Pro Tyr Glu Gly Thr Gln Thr Ser Thr Phe Lys Val
             35                  40                  45
Thr Met Ala Asn Gly Gly Pro Leu Ala Phe Ser Phe Asp Ile Leu Ser
         50                  55                  60
Thr Val Phe Lys Tyr Gly Asn Arg Cys Phe Thr Ala Tyr Pro Thr Ser
 65                  70                  75                  80
Met Pro Asp Tyr Phe Lys Gln Ala Phe Pro Asp Gly Met Ser Tyr Glu
                 85                  90                  95
Arg Thr Phe Thr Tyr Glu Asp Gly Gly Val Ala Thr Ala Ser Trp Glu
            100                 105                 110
Ile Ser Leu Lys Gly Asn Cys Phe Glu His Lys Ser Thr Phe His Gly
        115                 120                 125
Val Asn Phe Pro Ala Asp Gly Pro Val Met Ala Lys Met Thr Thr Gly
    130                 135                 140
Trp Asp Pro Ser Phe Glu Lys Met Thr Val Cys Asp Gly Ile Leu Lys
145                 150                 155                 160
Gly Asp Val Thr Ala Phe Leu Met Leu Gln Gly Gly Asn Tyr Arg
                165                 170                 175
Cys Gln Phe His Thr Ser Tyr Lys Thr Lys Lys Pro Val Thr Met Pro
            180                 185                 190
Pro Asn His Ala Val Glu His Arg Ile Ala Arg Thr Asp Leu Asp Lys
        195                 200                 205
Gly Gly Asn Ser Val Gln Leu Thr Glu His Ala Val Ala His Ile Thr
    210                 215                 220
Ser Val Val Pro Phe
225
```

<210> SEQ ID NO 3
<211> LENGTH: 1116
<212> TYPE: DNA
<213> ORGANISM: Clavularia species
<220> FEATURE:
<221> NAME/KEY: misc_feature
<222> LOCATION: 8, 12, 13, 17, 65, 77, 102, 104
<223> OTHER INFORMATION: n = A,T,C or G

<400> SEQUENCE: 3

```
tatagganca tnngggngat tggggtccaa agcattgtaa ccaacgcaga taacccccag    60
tggtntcaaa cgcaganaac gcgggaacat tggaaaattg antnttaagg aggcaaggaa   120
tcgggagtaa agttgcgaga aactgaaaaa atgaagtgta aatttgtgtt ctgcctgtcc   180
ttcttggtcc tcgccatcac aaacgcgaac attttttga gaaacgaggc tgacttagaa   240
gagaagacat tgagaatacc aaaagctcta accaccatgg gtgtgattaa accagacatg   300
```

```
aagattaagc tgaagatgga aggaaatgta aacgggcatg cttttgtgat cgaaggagaa    360
ggagaaggaa agccttacga tgggacacac actttaaacc tggaagtgaa ggaaggtgcg    420
cctctgcctt tttcttacga tatcttgtca aacgcgttcc agtacggaaa cagagcattg    480
acaaaatacc cagacgatat agcagactat ttcaagcagt cgtttcccga gggatattcc    540
tgggaaagaa ccatgacttt tgaagacaaa ggcattgtca agtgaaaag tgacataagc     600
atggaggaag actcctttat ctatgaaatt cgttttgatg ggatgaactt tcctcccaat    660
ggtccggtta tgcagaaaaa aactttgaag tgggaaccat ccactgagat tatgtacgtg    720
cgtgatggag tgctggtcgg agatattagc cattctctgt tgctggaggg aggtggccat    780
taccgatgtg acttcaaaag tatttacaaa gcaaaaaag ttgtcaaatt gccagactat     840
cactttgtgg accatcgcat tgagatcttg aaccatgaca aggattacaa caaagtaacg    900
ctgtatgaga atgcagttgc tcgctattct ttgctgccaa gtcaggccta gacaacaagg    960
atactgaaaa catatttgtc tgagggtttg tgttgttttt taaaagacat cagctcagca   1020
ttcgttagtt gtaacaaaaa atagctttaa tttttggtgg gattaaatca tagggatttg   1080
ttttagtaat cattttgctt aataaaaagt gccttg                              1116

<210> SEQ ID NO 4
<211> LENGTH: 266
<212> TYPE: PRT
<213> ORGANISM: Clavularia species

<400> SEQUENCE: 4

Met Lys Cys Lys Phe Val Phe Cys Leu Ser Phe Leu Val Leu Ala Ile
1               5                   10                  15

Thr Asn Ala Asn Ile Phe Leu Arg Asn Glu Ala Asp Leu Glu Glu Lys
            20                  25                  30

Thr Leu Arg Ile Pro Lys Ala Leu Thr Thr Met Gly Val Ile Lys Pro
        35                  40                  45

Asp Met Lys Ile Lys Leu Lys Met Glu Gly Asn Val Asn Gly His Ala
    50                  55                  60

Phe Val Ile Glu Gly Glu Gly Gly Lys Pro Tyr Asp Gly Thr His
65                  70                  75                  80

Thr Leu Asn Leu Glu Val Lys Glu Gly Ala Pro Leu Pro Phe Ser Tyr
                85                  90                  95

Asp Ile Leu Ser Asn Ala Phe Gln Tyr Gly Asn Arg Ala Leu Thr Lys
            100                 105                 110

Tyr Pro Asp Asp Ile Ala Asp Tyr Phe Lys Gln Ser Phe Pro Glu Gly
        115                 120                 125

Tyr Ser Trp Glu Arg Thr Met Thr Phe Glu Asp Lys Gly Ile Val Lys
    130                 135                 140

Val Lys Ser Asp Ile Ser Met Glu Glu Asp Ser Phe Ile Tyr Glu Ile
145                 150                 155                 160

Arg Phe Asp Gly Met Asn Phe Pro Pro Asn Gly Pro Val Met Gln Lys
                165                 170                 175

Lys Thr Leu Lys Trp Glu Pro Ser Thr Glu Ile Met Tyr Val Arg Asp
            180                 185                 190

Gly Val Leu Val Gly Asp Ile Ser His Ser Leu Leu Glu Gly Gly
        195                 200                 205

Gly His Tyr Arg Cys Asp Phe Lys Ser Ile Tyr Lys Ala Lys Lys Val
    210                 215                 220

Val Lys Leu Pro Asp Tyr His Phe Val Asp His Arg Ile Glu Ile Leu
```

```
                225                 230                 235                 240
Asn His Asp Lys Asp Tyr Asn Lys Val Thr Leu Tyr Glu Asn Ala Val
                    245                 250                 255

Ala Arg Tyr Ser Leu Leu Pro Ser Gln Ala
        260                 265

<210> SEQ ID NO 5
<211> LENGTH: 693
<212> TYPE: DNA
<213> ORGANISM: Zoanthus species

<400> SEQUENCE: 5
atggctcagt caaagcacgg tctaacaaaa gaaatgacaa tgaaataccg tatggaaggg      60
tgcgtcgatg gacataaatt tgtgatcacg ggagagggca ttggatatcc gttcaaaggg     120
aaacaggcta ttaatctgtg tgtggtcgaa ggtggaccat tgccatttgc cgaagacata     180
ttgtcagctg cctttatgta cggaaacagg gttttcactg aatatcctca agacatagct     240
gactatttca gaactcgtgt cctgctggt tatacatggg acaggtcttt tctctttgag      300
gatggagcag tttgcatatg taatgcagat ataacagtga gtgttgaaga aaactgcatg     360
tatcatgagt ccaaatttta tggagtgaat tttcctgctg atggacctgt gatgaaaaag     420
atgacagata actgggagcc atcctgcgag aagatcatac cagtacctaa gcaggggata     480
ttgaaggggg atgtctccat gtacctcctt ctgaaggatg gtgggcgttt acggtgccaa     540
ttcgacacag tttacaaagc aaagtctgtg ccaagaaaga tgccggactg cacttcatc     600 cagcataagc tcacccgtga agaccgcagc gatgctaaga tcagaaatg gcatctgaca     660 gaacatgcta ttgcatccgg atctgcattg ccc                                 693

<210> SEQ ID NO 6
<211> LENGTH: 231
<212> TYPE: PRT
<213> ORGANISM: Zoanthus species

<400> SEQUENCE: 6

Met Ala Gln Ser Lys His Gly Leu Thr Lys Glu Met Thr Met Lys Tyr
1               5                   10                  15

Arg Met Glu Gly Cys Val Asp Gly His Lys Phe Val Ile Thr Gly Glu
            20                  25                  30

Gly Ile Gly Tyr Pro Phe Lys Gly Lys Gln Ala Ile Asn Leu Cys Val
        35                  40                  45

Val Glu Gly Gly Pro Leu Pro Phe Ala Glu Asp Ile Leu Ser Ala Ala
    50                  55                  60

Phe Asn Tyr Gly Asn Arg Val Phe Thr Glu Tyr Pro Gln Asp Ile Ala
65                  70                  75                  80

Asp Tyr Phe Lys Asn Ser Cys Pro Ala Gly Tyr Thr Trp Asp Arg Ser
                85                  90                  95

Phe Leu Phe Glu Asp Gly Ala Val Cys Ile Cys Asn Ala Asp Ile Thr
            100                 105                 110

Val Ser Val Glu Glu Asn Cys Met Tyr His Glu Ser Lys Phe Tyr Gly
        115                 120                 125

Val Asn Phe Pro Ala Asp Gly Pro Val Met Lys Met Thr Asp Asn
    130                 135                 140

Trp Glu Pro Ser Cys Glu Lys Ile Ile Pro Val Pro Lys Gln Gly Ile
145                 150                 155                 160

Leu Lys Gly Asp Val Ser Met Tyr Leu Leu Leu Lys Asp Gly Gly Arg
```

```
            165                 170                 175
Leu Arg Cys Gln Phe Asp Thr Val Tyr Lys Ala Lys Ser Val Pro Arg
            180                 185                 190

Lys Met Pro Asp Trp His Phe Ile Gln His Lys Leu Thr Arg Glu Asp
        195                 200                 205

Arg Ser Asp Ala Lys Asn Gln Lys Trp His Leu Thr Glu His Ala Ile
    210                 215                 220

Ala Ser Gly Ser Ala Leu Pro
225                 230

<210> SEQ ID NO 7
<211> LENGTH: 865
<212> TYPE: DNA
<213> ORGANISM: Zoanthus species

<400> SEQUENCE: 7
gagttgagtt tctcgacttc agttgtatca attttggggc atcaagcgat ctattttcaa        60
catggctcat tcaaagcacg gtctaaaaga agaaatgaca atgaaatacc acatggaagg       120
gtgcgtcaac ggacataaat tgtgatcac  gggcgaaggc attggatatc cgttcaaagg       180
gaaacagact attaatctgt gtgtgatcga aggggggacca ttgccatttt ccgaagacat      240
attgtcagct ggctttaagt acggagacag gattttcact gaatatcctc aagacatagt      300
agactatttc aagaactcgt gtcctgctgg atatacatgg ggcaggtctt ttctctttga      360
ggatggagca gtctgcatat gcaatgtaga tataacagtg agtgtcaaag aaaactgcat      420
ttatcataag agcatattta atggaatgaa ttttcctgct gatggacctg tgatgaaaaa      480
gatgacaact aactgggaag catcctgcga agatcatg ccagtaccta agcaggggat      540
actgaaaggg gatgtctcca tgtacctcct tctgaaggat ggtgggcgtt accggtgcca      600
gttcgacaca gtttacaaag caaagtctgt gccaagtaag atgccggagt ggcacttcat      660
ccagcataag ctcctccgtg aagaccgcag cgatgctaag aatcagaagt ggcagctgac      720
agagcatgct attgcattcc cttctgcctt ggcctgataa aatgtagtt  ccaacatttt      780
aatgcatgtg cttgtcaatt attctgataa aaatgtagtt gagttgaaaa cagacaagta      840
caaataaagc acatgtaaat cgtct                                             865

<210> SEQ ID NO 8
<211> LENGTH: 230
<212> TYPE: PRT
<213> ORGANISM: Zoanthus species

<400> SEQUENCE: 8

Met Ala His Ser Lys His Gly Leu Lys Glu Glu Met Thr Met Lys Tyr
1               5                   10                  15

His Met Glu Gly Cys Val Asn Gly His Lys Phe Val Ile Thr Gly Glu
            20                  25                  30

Gly Ile Gly Tyr Pro Phe Lys Gly Lys Gln Thr Ile Asn Leu Cys Val
        35                  40                  45

Ile Glu Gly Gly Pro Leu Pro Phe Ser Glu Asp Ile Leu Ser Ala Gly
    50                  55                  60

Phe Lys Tyr Gly Asp Arg Ile Phe Thr Glu Tyr Pro Gln Asp Ile Val
65                  70                  75                  80

Asp Tyr Phe Lys Asn Ser Cys Pro Ala Gly Tyr Thr Trp Gly Ser Phe
            85                  90                  95

Leu Phe Glu Asp Gly Ala Val Cys Ile Cys Asn Val Asp Ile Thr Val
```

```
                100                 105                 110
Ser Val Lys Glu Asn Cys Ile Tyr His Lys Ser Ile Phe Asn Gly Met
            115                 120                 125

Asn Phe Pro Ala Asp Gly Pro Val Met Lys Met Thr Thr Asn Trp
        130                 135                 140

Glu Ala Ser Cys Glu Lys Ile Met Pro Val Pro Lys Gln Gly Ile Leu
145                 150                 155                 160

Lys Gly Asp Val Ser Met Tyr Leu Leu Lys Asp Gly Gly Arg Tyr
                165                 170                 175

Arg Cys Gln Phe Asp Thr Val Tyr Lys Ala Lys Ser Val Pro Ser Lys
            180                 185                 190

Met Pro Glu Trp His Phe Ile Gln His Lys Leu Leu Arg Glu Asp Arg
        195                 200                 205

Ser Asp Ala Lys Asn Gln Lys Trp Gln Leu Thr Glu His Ala Ile Ala
        210                 215                 220

Phe Pro Ser Ala Leu Ala
225                 230

<210> SEQ ID NO 9
<211> LENGTH: 850
<212> TYPE: DNA
<213> ORGANISM: Disosoma striata

<400> SEQUENCE: 9
acggtcaggg acacggtgac ccactttggt attctaacaa aatgagttgg tccaagagtg      60
tgatcaagga agaaatgttg atcgatcttc atctggaagg aacgttcaat gggcactact     120
ttgaaataaa aggcaaagga aaagggaagc ctaatgaagg caccaatacc gtcacgctcg     180
aggttaccaa gggtggacct ctgccatttg gttggcatat tttgtgccca caatttcagt     240
atggaaacaa ggcatttgtc caccaccctg acgacatacc tgattatcta aagctgtcat     300
ttccggaggg atatacatgg aacggtccaa tgcactttga agacggtggc ttgtgttgta     360
tcaccaatga tatcagtttg acaggcaact gtttcaacta cgacatcaag ttcactggct     420
tgaactttcc tccaaatgga cccgttgtgc agaagaagac aactggctgg gaaccgagca     480
ctgagcgttt gtatcctcgt gatggcgtgt tgataggaga catccatcat gctctcacag     540
tggaaggagg tggtcattac gtatgtgaca ttaaaactgt ttacagggcc aagaagcccg     600
taaagatgcc agggtatcac tatgttgaca ccaaactggt tataaggagc aacgacaaag     660
aattcatgaa agttgaggag catgaaatcg ccgttgcacg ccaccatccg ctccaaagcc     720
aatgaagctt aagtaaagca aaaggtgac gaggcatgat agtatgacat gatagtatga     780
catgatagta tgacatgata gtaagaattg taagcaaaag ctttgcttaa ttaaacttgt     840
aattgaaaac                                                            850

<210> SEQ ID NO 10
<211> LENGTH: 227
<212> TYPE: PRT
<213> ORGANISM: Discosoma striata

<400> SEQUENCE: 10

Met Ser Trp Ser Lys Ser Val Ile Lys Glu Glu Met Leu Ile Asp Leu
1               5                   10                  15

His Leu Glu Gly Thr Phe Asn Gly His Tyr Phe Glu Ile Lys Gly Lys
            20                  25                  30

Gly Lys Gly Lys Pro Asn Glu Gly Thr Asn Thr Val Thr Leu Glu Val
```

```
                35                  40                  45
Thr Lys Gly Gly Pro Leu Pro Phe Gly Trp His Ile Leu Cys Pro Gln
 50                  55                  60

Phe Gln Tyr Gly Asn Lys Ala Phe Val His His Pro Asp Asp Ile Pro
 65                  70                  75                  80

Asp Tyr Leu Lys Leu Ser Phe Pro Glu Gly Tyr Thr Trp Glu Arg Ser
                 85                  90                  95

Met His Phe Glu Asp Gly Gly Leu Cys Cys Ile Thr Asn Asp Ile Ser
                100                 105                 110

Leu Thr Gly Asn Cys Phe Asn Tyr Asp Ile Lys Phe Thr Gly Leu Asn
            115                 120                 125

Phe Pro Pro Asn Gly Pro Val Val Gln Lys Lys Thr Thr Gly Trp Glu
130                 135                 140

Pro Ser Thr Glu Arg Leu Tyr Pro Arg Asp Gly Val Leu Ile Gly Asp
145                 150                 155                 160

Ile His His Ala Leu Thr Val Glu Gly Gly His Tyr Val Cys Asp
                165                 170                 175

Ile Lys Thr Val Tyr Arg Ala Lys Lys Pro Val Lys Met Pro Gly Tyr
            180                 185                 190

His Tyr Val Asp Thr Lys Leu Val Ile Arg Ser Asn Asp Lys Glu Phe
        195                 200                 205

Met Lys Val Glu Glu His Glu Ile Ala Val Ala Arg His His Pro Leu
210                 215                 220

Gln Ser Gln
225

<210> SEQ ID NO 11
<211> LENGTH: 678
<212> TYPE: DNA
<213> ORGANISM: Discosoma species

<400> SEQUENCE: 11
atgaggtctt ccaagaatgt tatcaaggag ttcatgaggt ttaaggttcg catggaagga      60
acggtcaatg ggcacgagtt tgaaatagaa ggcgaaggag aggggaggcc atacgaaggc     120
cacaataccg taaagcttaa ggtaaccaag gggggacctt tgccatttgc ttggatatt     180 ttgtcaccac aatttcagta tggaagcaag gtatatgtca agcaccctgc cgacatacca     240
gactataaaa agctgtcatt tcctgaagga tttaaatggg aaagggtcat gaactttgaa     300
gacggtggcg tcgttactgt aacccaggat tccagtttgc aggatggctg tttcatctac     360
aaggtcaagt tcattggcgt gaactttcct tccgatggac ctgttatgca aaagaagaca     420
atgggctggg aagccagcac tgagcgtttg tatcctcgtg atggcgtgtt gaaggagag      480 attcataagg ctctgaagct gaaagacggt ggtcattacc tagttgaatt caaaagtatt     540
tacatggcaa agaagcctgt gcagctacca gggtactact atgttgactc aaactggat     600 ataacaagcc acaacgaaga ctatacaatc gttgagcagt atgaaagaac cgagggacgc     660
caccatctgt cctttaa                                                    678

<210> SEQ ID NO 12
<211> LENGTH: 225
<212> TYPE: PRT
<213> ORGANISM: Discosoma species

<400> SEQUENCE: 12

Met Arg Ser Ser Lys Asn Val Ile Lys Glu Phe Met Arg Phe Lys Val
```

```
                 1               5                 10                15
            Arg Met Glu Gly Thr Val Asn Gly His Glu Phe Glu Ile Glu Gly Glu
                             20                  25                  30

Gly Glu Gly Arg Pro Tyr Glu Gly His Asn Thr Val Lys Leu Lys Val
                         35                  40                  45

Thr Lys Gly Gly Pro Leu Pro Phe Ala Trp Asp Ile Leu Ser Pro Gln
                     50                  55                  60

Phe Gln Tyr Gly Ser Lys Val Tyr Val Lys His Pro Ala Asp Ile Pro
             65                  70                  75                  80

Asp Tyr Lys Lys Leu Ser Phe Pro Glu Gly Phe Lys Trp Glu Arg Val
                             85                  90                  95

Met Asn Phe Glu Asp Gly Gly Val Val Thr Val Thr Gln Asp Ser Ser
                        100                 105                 110

Leu Gln Asp Gly Cys Phe Ile Tyr Lys Val Lys Phe Ile Gly Val Asn
                        115                 120                 125

Phe Pro Ser Asp Gly Pro Val Met Gln Lys Lys Thr Met Gly Trp Glu
                    130                 135                 140

Ala Ser Thr Glu Arg Leu Tyr Pro Arg Asp Gly Val Leu Lys Gly Glu
            145                 150                 155                 160

Ile His Lys Ala Leu Lys Leu Lys Asp Gly Gly His Tyr Leu Val Glu
                            165                 170                 175

Phe Lys Ser Ile Tyr Met Ala Lys Lys Pro Val Gln Leu Pro Gly Tyr
                        180                 185                 190

Tyr Tyr Val Asp Ser Lys Leu Asp Ile Thr Ser His Asn Glu Asp Tyr
                        195                 200                 205

Thr Ile Val Glu Gln Tyr Glu Arg Thr Glu Gly Arg His His Leu Phe
                    210                 215                 220

Leu
            225

<210> SEQ ID NO 13
<211> LENGTH: 696
<212> TYPE: DNA
<213> ORGANISM: Anemonia sulcata

<400> SEQUENCE: 13
atggcttcct ttttaaagaa gactatgccc tttaagacga ccattgaagg gacggttaat        60
ggccactact tcaagtgtac aggaaaagga gagggcaacc catttgaggg tacgcaggaa       120
atgaagatag aggtcatcga aggaggtcca ttgccatttg ccttccacat tttgtcaacg       180
agttgtatgt acggtagtaa ggccttcatc aagtatgtgt caggaattcc tgactacttc       240
aagcagtctt ccctgaagg ttttacttgg aaagaaccaa caacctacga ggatggaggc       300
tttcttacag ctcatcagga cacaagccta gatggagatt gcctcgttta caaggtcaag       360
attcttggta taattttcc tgctgatggc cccgtgatgc agaacaaagc aggaagatgg       420
gagccatcca ccgagatagt ttatgaagtt gacggtgtcc tgcgtggaca gtctttgatg       480
gcccttaagt gccctggtgg tcgtcatctg acttgccatc tccatactac ttacaggtcc       540
aaaaaaccag ctgctgcctt gaagatgcca ggatttcatt ttgaagatca tcgcatcgag       600
ataatggagg aagttgagaa aggcaagtgc tataaaacagt acgaagcagc agtgggcagg       660
tactgtgatg ctgctccatc caagcttgga cataac                                 696

<210> SEQ ID NO 14
<211> LENGTH: 232
```

<212> TYPE: PRT
<213> ORGANISM: Anemonia sulcata

<400> SEQUENCE: 14

```
Met Ala Ser Phe Leu Lys Lys Thr Met Pro Phe Lys Thr Thr Ile Glu
1               5                   10                  15

Gly Thr Val Asn Gly His Tyr Phe Lys Cys Thr Gly Lys Gly Glu Gly
            20                  25                  30

Asn Pro Phe Glu Gly Thr Gln Glu Met Lys Ile Glu Val Ile Glu Gly
        35                  40                  45

Gly Pro Leu Pro Phe Ala Phe His Ile Leu Ser Thr Ser Cys Met Tyr
50                  55                  60

Gly Ser Lys Thr Phe Ile Lys Tyr Val Ser Gly Ile Pro Asp Tyr Phe
65                  70                  75                  80

Lys Gln Ser Phe Pro Glu Gly Phe Thr Trp Glu Arg Thr Thr Thr Tyr
                85                  90                  95

Glu Asp Gly Gly Phe Leu Thr Ala His Gln Asp Thr Ser Leu Asp Gly
            100                 105                 110

Asp Cys Leu Val Tyr Lys Val Lys Ile Leu Gly Asn Asn Phe Pro Ala
        115                 120                 125

Asp Gly Pro Val Met Gln Asn Lys Ala Gly Arg Trp Glu Pro Ala Thr
130                 135                 140

Glu Ile Val Tyr Glu Val Asp Gly Val Leu Arg Gly Gln Ser Leu Met
145                 150                 155                 160

Ala Leu Lys Cys Pro Gly Gly Arg His Leu Thr Cys His Leu His Thr
                165                 170                 175

Thr Tyr Arg Ser Lys Lys Pro Ala Ala Ala Leu Lys Met Pro Gly Phe
            180                 185                 190

His Phe Glu Asp His Arg Ile Glu Ile Met Glu Glu Val Glu Lys Gly
        195                 200                 205

Lys Cys Tyr Lys Gln Tyr Glu Ala Ala Val Gly Arg Tyr Cys Asp Ala
    210                 215                 220

Ala Pro Ser Lys Leu Gly His Asn
225                 230
```

<210> SEQ ID NO 15
<211> LENGTH: 919
<212> TYPE: DNA
<213> ORGANISM: Discosoma species

<400> SEQUENCE: 15

```
attcacctcg gtgatttgta agagaaagga tcaccatcaa gagaagagct gtaaagtta      60
atattttact gtacttctac cagcatgagt gcacttaaag aagaaatgaa atcaacctt     120
acaatggaag tgttgttaa cgggcttcca tttaagatcc gtggggatgg aaaaggcaaa    180
ccataccagg gatcacagga gttaaccttg acgtggttaa aaggcgggcc tctgcctttc   240
tcttatgata ttctgacaac gatgtttcag tacggcaaca gggcattcgt aaactaccca   300
gaggacatac cagatatttt caagcagacc tgttctggtc ctaatggtgg atattcctgg   360
caaaggacca tgacttatga agacggaggc gtttgcactg ctacaagcaa catcagcgtg   420
gttggcgaca ctttcaatta tgacattcac tttatgggag cgaattttcc tcttgatggt   480
ccagtgatgc agaaaagaac aatgaaatgg gaaccatcca ctgagataat gtttgaacgt   540
gatgaaatgc tgaggggtga cattgccatg tctctgttgc tgaagggagg ggccattac    600
cgatgtgatt ttgaaactat ttataaaccc aataaggttg tcaagatgcc agattaccat   660
```

```
tttgtggacc actgcattga gataacgagt caacaggatt attacaacgt ggttgagctg      720
accgaggttg ctgaagcccg ctactcttcg ctggagaaaa tcggcaaatc aaaggcgtaa      780
atccaagcaa tctaagaaaa caacaaggca ttaaaccgaa tcaccgtttt gaattttcg       840 ttcggaattt cttggtaaaa ctaggtttag aacgtttcat ttcgctggac ttctttgact      900
cagctgtaga caagaaaga                                                   919
```

<210> SEQ ID NO 16
<211> LENGTH: 231
<212> TYPE: PRT
<213> ORGANISM: Discosoma species

<400> SEQUENCE: 16

```
Met Ser Ala Leu Lys Glu Glu Met Lys Ile Asn Leu Thr Met Glu Gly
 1               5                  10                  15

Val Val Asn Gly Leu Pro Phe Lys Ile Arg Gly Asp Gly Lys Gly Lys
            20                  25                  30

Pro Tyr Gln Gly Ser Gln Glu Leu Thr Leu Thr Val Lys Gly Gly
        35                  40                  45

Pro Leu Pro Phe Ser Tyr Asp Ile Leu Thr Thr Met Phe Gln Tyr Gly
    50                  55                  60

Asn Arg Ala Phe Val Asn Tyr Pro Glu Asp Ile Pro Asp Ile Phe Lys
65                  70                  75                  80

Gln Thr Cys Ser Gly Pro Asn Gly Gly Tyr Ser Trp Gln Arg Thr Met
                85                  90                  95

Thr Tyr Glu Asp Gly Gly Val Cys Thr Ala Thr Ser Asn Ile Ser Val
            100                 105                 110

Val Gly Asp Thr Phe Asn Tyr Asp Ile His Phe Met Gly Ala Asn Phe
        115                 120                 125

Pro Leu Asp Gly Pro Val Met Gln Lys Arg Thr Met Lys Trp Glu Pro
    130                 135                 140

Ser Thr Glu Ile Met Phe Glu Arg Asp Gly Met Leu Arg Gly Asp Ile
145                 150                 155                 160

Ala Met Ser Leu Leu Leu Lys Gly Gly Gly His Tyr Arg Cys Asp Phe
                165                 170                 175

Glu Thr Ile Tyr Lys Pro Asn Lys Val Val Lys Met Pro Asp Tyr His
            180                 185                 190

Phe Val Asp His Cys Ile Glu Ile Thr Ser Gln Gln Asp Tyr Tyr Asn
        195                 200                 205

Val Val Glu Leu Thr Glu Val Ala Glu Ala Arg Tyr Ser Ser Leu Glu
    210                 215                 220

Lys Ile Gly Lys Ser Lys Ala
225                 230
```

<210> SEQ ID NO 17
<211> LENGTH: 876
<212> TYPE: DNA
<213> ORGANISM: Discosoma species

<400> SEQUENCE: 17

```
agtttcagcc agtgacaggg tgagctgcca ggtattctaa caagatgagt tgttccaaga      60
atgtgatcaa ggagttcatg aggttcaagg ttcgtatgga aggaacggtc aatgggcacg     120
agtttgaaat aaaaggcgaa ggtgaaggga ggccttacga aggtcactgt tccgtaaagc     180
ttatggtaac caagggtgga cctttgccat ttgcttttga tattttgtca ccacaatttc     240
```

-continued

```
agtatggaag caaggtatat gtcaaacacc ctgccgacat accagactat aaaaagctgt    300
catttcctga gggatttaaa tgggaaaggg tcatgaactt tgaagacggt ggcgtggtta    360
ctgtatccca agattccagt ttgaaagacg gctgtttcat ctacgaggtc aagttcattg    420
gggtgaactt tccttctgat ggacctgtta tgcagaggag gacacggggc tgggaagcca    480
gctctgagcg tttgtatcct cgtgatgggg tgctgaaagg agacatccat atggctctga    540
ggctggaagg aggcggccat tacctcgttg aattcaaaag tatttacatg gtaaagaagc    600
cttcagtgca gttgccaggc tactattatg ttgactccaa actggatatg acagccaca    660 acgaagatta cacagtcgtt gagcagtatg aaaaaaccca gggacgccac catccgttca    720
ttaagcctct gcagtgaact cggctcagtc atggattagc ggtaatggcc acaaaaggca    780
cgatgatcgt ttttaggaa tgcagccaaa aattgaaggt tatgacagta gaaatacaag    840
caacaggctt tgcttattaa acatgtaatt gaaaac                             876
```

<210> SEQ ID NO 18
<211> LENGTH: 230
<212> TYPE: PRT
<213> ORGANISM: Discosoma species

<400> SEQUENCE: 18

```
Met Ser Cys Ser Lys Asn Val Ile Lys Glu Phe Met Arg Phe Lys Val
  1               5                  10                  15

Arg Met Glu Gly Thr Val Asn Gly His Glu Phe Glu Ile Lys Gly Glu
             20                  25                  30

Gly Glu Gly Arg Pro Tyr Glu Gly His Cys Ser Val Lys Leu Met Val
         35                  40                  45

Thr Lys Gly Gly Pro Leu Pro Phe Ala Phe Asp Ile Leu Ser Pro Gln
     50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Val Thr Val Ser Gln Asp Ser Ser
            100                 105                 110

Leu Lys Asp Gly Cys Phe Ile Tyr Glu Val Lys Phe Ile Gly Val Asn
        115                 120                 125

Phe Pro Ser Asp Gly Pro Val Met Gln Arg Arg Thr Arg Gly Trp Glu
    130                 135                 140

Ala Ser Ser Glu Arg Leu Tyr Pro Arg Asp Gly Val Leu Lys Gly Asp
145                 150                 155                 160

Ile His Met Ala Leu Arg Leu Glu Gly Gly His Tyr Leu Val Glu
                165                 170                 175

Phe Lys Ser Ile Tyr Met Val Lys Pro Ser Val Gln Leu Pro Gly
            180                 185                 190

Tyr Tyr Tyr Val Asp Ser Lys Leu Asp Met Thr Ser His Asn Glu Asp
    195                 200                 205

Tyr Thr Val Val Glu Gln Tyr Glu Lys Thr Gln Gly Arg His His Pro
210                 215                 220

Phe Ile Lys Pro Leu Gln
225                 230
```

<210> SEQ ID NO 19
<211> LENGTH: 26

```
<212> TYPE: DNA
<213> ORGANISM: Artificial Sequence
<220> FEATURE:
<223> OTHER INFORMATION: Primer

<400> SEQUENCE: 19
atgtgcaata ccaacatgtc tgtacc                                          26

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ctaggggaaa taagttagca c                                               21

<210> SEQ ID NO 21
<211> LENGTH: 41
<212> TYPE: DNA
<213> ORGANISM: Artificial Sequence
<220> FEATURE:
<223> OTHER INFORMATION: Primer

<400> SEQUENCE: 21
ggaattccag ccatggtgtg caataccaac atgtctgtac c                         41

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
tcccccgggg ggaaataagt tagcac                                          26

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
acatggatcc aggtcttcca agaatgttat c                                    31

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
tagtactcga gccaagttca gcctta                                          26

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
```

```
acatggatcc agttgttcca agaatgtgat                                      30
```

<210> SEQ ID NO 26
<211> LENGTH: 27
<212> TYPE: DNA
<213> ORGANISM: Artificial Sequence
<220> FEATURE:
<223> OTHER INFORMATION: Primer

<400> SEQUENCE: 26

```
tagtactcga ggccattacc gctaatc                                         27
```

<210> SEQ ID NO 27
<211> LENGTH: 690
<212> TYPE: DNA
<213> ORGANISM: Anemonia majano

<400> SEQUENCE: 27

```
atggccctgt ccaacgagtt catcggcgac gacatgaaga tgacctacca catggacggc      60
tgcgtgaacg gccactactt caccgtgaag ggcgagggca gcggcaagcc ctacgagggc     120
acccagacct ccaccttcaa ggtgaccatg gccaacggcg gccccctggc cttctccttc     180
gacatcctgt ccaccgtgtt catgtacggc aaccgctgct tcaccgccta ccccaccagc     240
atgcccgact acttcaagca ggccttcccc gacggcatgt cctacgagag aaccttcacc     300
tacgaggacg gcggcgtggc caccgccagc tgggagatca gcctgaaggg caactgcttc     360
gagcacaagt ccaccttcca cggcgtgaac ttccccgccg acggccccgt gatggccaag     420
aagaccaccg gctgggaccc ctccttcgag aagatgaccg tgtgcgacgg catcttgaag     480
ggcgacgtga ccgccttcct gatgctgcag ggcggcggca actacagatg ccagttccac     540
acctcctaca agaccaagaa gcccgtgacc atgccccca accacgtggt ggagcaccgc     600
atcgccagaa ccgacctgga caagggcggc aacagcgtgc agctgaccga gcacgccgtg     660
gcccacatca cctccgtggt gcccttctga                                     690
```

<210> SEQ ID NO 28
<211> LENGTH: 229
<212> TYPE: PRT
<213> ORGANISM: Anemonia majano

<400> SEQUENCE: 28

```
Met Ala Leu Ser Asn Glu Phe Ile Gly Asp Asp Met Lys Met Thr Tyr
  1               5                  10                  15

His Met Asp Gly Cys Val Asn Gly His Tyr Phe Thr Val Lys Gly Glu
             20                  25                  30

Gly Ser Gly Lys Pro Tyr Glu Gly Thr Gln Thr Ser Thr Phe Lys Val
         35                  40                  45

Thr Met Ala Asn Gly Gly Pro Leu Ala Phe Ser Phe Asp Ile Leu Ser
     50                  55                  60

Thr Val Phe Met Tyr Gly Asn Arg Cys Phe Thr Ala Tyr Pro Thr Ser
 65                  70                  75                  80

Met Pro Asp Tyr Phe Lys Gln Ala Phe Pro Asp Gly Met Ser Tyr Glu
                 85                  90                  95

Arg Thr Phe Thr Tyr Glu Asp Gly Gly Val Ala Thr Ala Ser Trp Glu
            100                 105                 110

Ile Ser Leu Lys Gly Asn Cys Phe Glu His Lys Ser Thr Phe His Gly
        115                 120                 125

Val Asn Phe Pro Ala Asp Gly Pro Val Met Ala Lys Lys Thr Thr Gly
```

-continued

```
                130                 135                 140
Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Asn Tyr Arg
                165                 170                 175

Cys Gln Phe His Thr Ser Tyr Lys Thr Lys Pro Val Thr Met Pro
                180                 185                 190

Pro Asn His Val Val Glu His Arg Ile Ala Arg Thr Asp Leu Asp Lys
            195                 200                 205

Gly Gly Asn Ser Val Gln Leu Thr Glu His Ala Val Ala His Ile Thr
210                 215                 220

Ser Val Val Pro Phe
225
```

<210> SEQ ID NO 29
<211> LENGTH: 705
<212> TYPE: DNA
<213> ORGANISM: Zoanthus species

<400> SEQUENCE: 29

```
ggatccgctc agtcagagca cggtctaaca gaagaaatga caatgaaata ccgtatggaa      60
gggtgcgtcg atggacataa atttgtgatc acgggagagg gcattggata tccgttcaaa     120
gggaaacagg ctattaatct gtgtgtggtc gaaggtggac cattgccatt tgccgaagac     180
atattgtcag ctgcctttat gtacggaaac agggttttca ctgaatatcc tcaagacata     240
gttgactatt tcaagaactc cgtgtcctgct ggatatacat gggacaggtc ttttctcttt     300
gaggatggag cagtttgcat atgtaatgca gatataacag tgagtgttga agaaaactgc     360
atgtatcatg agtccaaatt ctatggagtg aatttccctg ctgatggacc tgtgatgaaa     420
aagatgacag ataactggga gccatcctgc gagaagatca taccagtacc taagcagggg     480
atattgaaag gggatgtctc catgtacctc cttctgaagg atggtgggcg tttacggtgc     540
caattcgaca cagtttacaa agcaaagtct gtgccaagaa agatgccgga ctggcacttc     600
atccagcata agctcacccg tgaagaccgc agcgatgcta agaatcagaa atggcatctg     660
acagaacatg ctattgcatc cggatctgca ttgccctgaa agctt                     705
```

<210> SEQ ID NO 30
<211> LENGTH: 230
<212> TYPE: PRT
<213> ORGANISM: Zoanthus species

<400> SEQUENCE: 30

```
Ala Gln Ser Glu His Gly Leu Thr Glu Glu Met Thr Met Lys Tyr Arg
 1                  5                  10                 15

Met Glu Gly Cys Val Asp Gly His Lys Phe Val Ile Thr Gly Glu Gly
                20                  25                  30

Ile Gly Tyr Pro Phe Lys Gly Lys Gln Ala Ile Asn Leu Cys Val Val
            35                  40                  45

Glu Gly Gly Pro Leu Pro Phe Ala Glu Asp Ile Leu Ser Ala Ala Phe
        50                  55                  60

Met Tyr Gly Asn Arg Val Phe Thr Glu Tyr Pro Gln Asp Ile Val Asp
65                  70                  75                  80

Tyr Phe Lys Asn Ser Cys Pro Ala Gly Tyr Thr Trp Asp Arg Ser Phe
                85                  90                  95

Leu Phe Glu Asp Gly Ala Val Cys Ile Cys Asn Ala Asp Ile Thr Val
```

```
                100                 105                 110
Ser Val Glu Glu Asn Cys Met Tyr His Glu Ser Lys Phe Tyr Gly Val
        115                 120                 125

Asn Phe Pro Ala Asp Gly Pro Val Met Lys Lys Met Thr Asp Asn Trp
    130                 135                 140

Glu Pro Ser Cys Glu Lys Ile Ile Pro Val Pro Lys Gln Gly Ile Leu
145                 150                 155                 160

Lys Gly Asp Val Ser Met Tyr Leu Leu Lys Asp Gly Gly Arg Leu
                165                 170                 175

Arg Cys Gln Phe Asp Thr Val Tyr Lys Ala Lys Ser Val Pro Arg Lys
                180                 185                 190

Met Pro Asp Trp His Phe Ile Gln His Lys Leu Thr Arg Glu Asp Arg
            195                 200                 205

Ser Asp Ala Lys Asn Gln Lys Trp His Leu Thr Glu His Ala Ile Ala
    210                 215                 220

Ser Gly Ser Ala Leu Pro
225                 230

<210> SEQ ID NO 31
<211> LENGTH: 231
<212> TYPE: PRT
<213> ORGANISM: Zoanthus species

<400> SEQUENCE: 31

Met Ala Gln Ser Lys His Gly Leu Thr Lys Glu Met Thr Met Lys Tyr
1               5                   10                  15

Arg Met Glu Gly Cys Val Asp Gly His Lys Phe Val Ile Thr Gly Glu
                20                  25                  30

Gly Ile Gly Tyr Pro Phe Lys Gly Lys Gln Ala Ile Asn Leu Cys Val
            35                  40                  45

Val Glu Gly Gly Pro Leu Pro Phe Ala Glu Asp Ile Leu Ser Ala Gly
        50                  55                  60

Phe Lys Tyr Gly Asp Arg Val Phe Thr Glu Tyr Pro Gln Asp Ile Val
65                  70                  75                  80

Asp Tyr Phe Lys Asn Ser Cys Pro Ala Gly Tyr Thr Trp Asp Arg Ser
                85                  90                  95

Phe Leu Phe Glu Asp Gly Ala Val Cys Ile Cys Asn Ala Asp Ile Thr
            100                 105                 110

Val Ser Val Glu Glu Asn Cys Met Tyr His Glu Ser Lys Phe Tyr Gly
        115                 120                 125

Val Asn Phe Pro Ala Asp Gly Pro Val Met Lys Lys Met Thr Asp Asn
    130                 135                 140

Trp Glu Pro Ser Cys Glu Lys Ile Ile Pro Val Pro Lys Gln Gly Ile
145                 150                 155                 160

Leu Lys Gly Asp Val Ser Met Tyr Leu Leu Lys Asp Gly Gly Arg
                165                 170                 175

Leu Arg Cys Gln Phe Asp Thr Val Tyr Lys Ala Lys Ser Val Pro Arg
                180                 185                 190

Lys Met Pro Asp Trp His Phe Ile Gln His Lys Leu Thr Arg Glu Asp
            195                 200                 205

Arg Ser Asp Ala Lys Asn Gln Lys Trp His Leu Thr Glu His Ala Ile
    210                 215                 220

Ala Ser Gly Ser Ala Leu Pro
225                 230
```

<210> SEQ ID NO 32
<211> LENGTH: 231
<212> TYPE: PRT
<213> ORGANISM: Zoanthus species

<400> SEQUENCE: 32

Met Ala Gln Ser Lys His Gly Leu Thr Lys Glu Met Thr Met Lys Tyr
1               5                   10                  15

Arg Met Glu Gly Cys Val Asp Gly His Lys Phe Val Ile Thr Gly Glu
            20                  25                  30

Gly Ile Gly Tyr Pro Phe Lys Gly Lys Gln Ala Ile Asn Leu Cys Val
        35                  40                  45

Val Glu Gly Gly Pro Leu Pro Phe Ala Glu Asp Ile Leu Ser Ala Gly
    50                  55                  60

Phe Lys Tyr Gly Asp Arg Val Phe Thr Glu Tyr Pro Gln Asp Ile Val
65                  70                  75                  80

Asp Tyr Phe Lys Asn Ser Cys Pro Ala Gly Tyr Thr Trp Asn Arg Ser
                85                  90                  95

Phe Leu Phe Glu Asp Gly Ala Val Cys Ile Cys Asn Ala Asp Ile Thr
            100                 105                 110

Val Ser Val Glu Glu Asn Cys Val Tyr His Glu Ser Lys Phe Tyr Gly
        115                 120                 125

Val Asn Phe Pro Ala Asp Gly Pro Val Met Lys Lys Met Thr Asp Asn
    130                 135                 140

Trp Glu Pro Ser Cys Glu Lys Ile Ile Pro Val Pro Arg Gln Gly Ile
145                 150                 155                 160

Leu Lys Gly Asp Val Ser Met Tyr Leu Leu Leu Lys Asp Gly Gly Arg
                165                 170                 175

Leu Arg Cys Gln Phe Asp Thr Val Tyr Lys Ala Lys Ser Val Pro Arg
            180                 185                 190

Lys Met Pro Asp Trp His Phe Ile Gln His Lys Leu Thr Arg Glu Asp
        195                 200                 205

Arg Ser Asp Ala Lys Asn Gln Lys Trp His Leu Thr Glu His Ala Ile
    210                 215                 220

Ala Ser Gly Ser Ala Leu Ser
225                 230

<210> SEQ ID NO 33
<211> LENGTH: 657
<212> TYPE: DNA
<213> ORGANISM: Zoanthus species

<400> SEQUENCE: 33
taccacatgg agggctgcgt gaacggccac aagttcgtga tcaccggcga gggcatcggc      60
taccccttca aggcaagca gaccatcaac ctgtgcgtga tcgagggcgg ccccctgccc     120
ttcagcgagg acatcctgag cgccggcttc aagtacggcg accggatctt caccgagtac     180
ccccaggaca tcgtggacta cttcaagaac agctgccccg ccggctacac ctggggccgg     240
agcttcctgt tcgaggacgg cgccgtgtgc atctgtaacg cggacatcac cgtgagcgtg     300
aaggagaact gcatctacca caagagcatc ttcaacggcg tgaacttccc cgccgacggc     360
cccgtgatga agaagatgac caccaactgg gaggccagct gcgagaagat catgcccgtg     420
cctaagcagg gcatcctgaa gggcgacgtg agcatgtacc tgctgctgaa ggacggcggc     480
cggtaccggt gccagttcga caccgtgtac aaggccaaga gcgtgcccag caagatgccc     540

```
gagtggcact tcatccagca caagctgctg cgggaggacc ggagcgacgc caagaaccag      600
aagtggcagc tgaccgagca cgccatcgcc ttccccagcg ccctggcctg aaagctt        657
```

<210> SEQ ID NO 34
<211> LENGTH: 230
<212> TYPE: PRT
<213> ORGANISM: Zoanthus species

<400> SEQUENCE: 34

```
Ala His Ser Glu His Gly Leu Thr Glu Glu Met Thr Met Lys Tyr His
 1               5                  10                  15

Met Glu Gly Cys Val Asn Gly His Lys Phe Val Ile Thr Gly Glu Gly
            20                  25                  30

Ile Gly Tyr Pro Phe Lys Gly Lys Gln Thr Ile Asn Leu Cys Val Ile
        35                  40                  45

Glu Gly Gly Pro Leu Pro Phe Ser Glu Asp Ile Leu Ser Ala Gly Phe
    50                  55                  60

Lys Tyr Gly Asp Arg Ile Phe Thr Glu Tyr Pro Gln Asp Ile Val Asp
65                  70                  75                  80

Tyr Phe Lys Asn Ser Cys Pro Ala Gly Tyr Thr Trp Gly Arg Ser Phe
                85                  90                  95

Leu Phe Glu Asp Gly Ala Val Cys Ile Cys Asn Val Asp Ile Thr Val
            100                 105                 110

Ser Val Lys Glu Asn Cys Ile Tyr His Lys Ser Ile Phe Asn Gly Val
        115                 120                 125

Asn Phe Pro Ala Asp Gly Pro Val Met Lys Lys Met Thr Thr Asn Trp
    130                 135                 140

Glu Ala Ser Cys Glu Lys Ile Met Pro Val Pro Lys Gln Gly Ile Leu
145                 150                 155                 160

Lys Gly Asp Val Ser Met Tyr Leu Leu Leu Lys Asp Gly Gly Arg Tyr
                165                 170                 175

Arg Cys Gln Phe Asp Thr Val Tyr Lys Ala Lys Ser Val Pro Ser Lys
            180                 185                 190

Met Pro Glu Trp His Phe Ile Gln His Lys Leu Leu Arg Glu Asp Arg
        195                 200                 205

Ser Asp Ala Lys Asn Gln Lys Trp Gln Leu Thr Glu His Ala Ile Ala
    210                 215                 220

Phe Pro Ser Ala Leu Ala
225                 230
```

<210> SEQ ID NO 35
<211> LENGTH: 681
<212> TYPE: DNA
<213> ORGANISM: Discosoma species

<400> SEQUENCE: 35

```
atggtgcgct cctccaagaa cgtcatcaag gagttcatgc gcttcaaggt gcgcatggag      60
ggcaccgtga acggccacga gttcgagatc gagggcgagg cgagggccg ccctacgag       120 ggccacaaca ccgtgaagct gaaggtgacc aagggcggcc ccctgccctt cgcctgggac     180
atcctgtccc cccagttcca gtacggctcc aaggtgtacg tgaagcaccc cgccgacatc     240
cccgactaca agaagctgtc cttccccgag ggcttcaagt gggagcgcgt gatgaacttc     300
gaggacggcg gcgtggtgac cgtgacccaa gactcctccc tgcaggacgg ctgcttcatc     360
tacaaggtga agttcatcgg cgtgaacttc ccctccgacg gccccgtaat gcagaagaag     420
```

```
accatgggct gggaggcctc caccgagcgc ctgtaccccc gcgacggcgt gctgaagggc      480
gagatccaca aggccctgaa gctgaaggac ggcggccact acctggtgga gttcaagtcc      540
atctacatgg ccaagaagcc cgtgcagctg cccggctact actacgtgga ctccaagctg      600
gacatcacct cccacaacga ggactacacc atcgtggagc agtacgagcg caccgagggc      660
cgccaccacc tgttcctgta g                                                681
```

<210> SEQ ID NO 36
<211> LENGTH: 678
<212> TYPE: DNA
<213> ORGANISM: Discosoma species

<400> SEQUENCE: 36

```
atggcctcct ccgagaacgt catcaccgag ttcatgcgct tcaaggtgcg catggagggc       60
accgtgaacg gccacgagtt cgagatcgag ggcgagggcg agggccgccc ctacgagggc      120
cacaacaccg tgaagttgaa ggtgaccaag ggcggccccc tgcccttcgc ctgggacatc      180
ctgtcccccc agttccagta cggctccaag gtgtacgtga agcaccccgc cgacatcccc      240
gactacaaga gctgtccttt ccccgagggc ttcaagtggg agcgcgtgat gaacttcgag      300
gacggcggcg tggcgaccgt gacccaggac tcctccctgc aggacggctg cttcatctac      360
aaggtgaagt tcatcggcgt gaacttcccc tccgacggcc ccgtgatgca gaagaagacc      420
atgggctggg aggcctccac cgagcgcctg taccccgcg acggcgtgct gaagggcgag       480
atccacaagg ccctgaagct gaaggacggc ggccactacc tggtggagtt caagtccatc      540
tacatggcca agaagcccgt gcagctgccc ggctactact acgtggacac caagctggac      600
atcacctccc acaacgagga ctacaccatc gtggagcagt acgagcgcac cgagggccgc      660
caccacctgt tcctgtaa                                                    678
```

<210> SEQ ID NO 37
<211> LENGTH: 681
<212> TYPE: DNA
<213> ORGANISM: Discosoma species

<400> SEQUENCE: 37

```
atggtgcgct cctccaagaa cgtcatcaag gagttcatgc gcttcaaggt gcgcatggag       60
ggcaccgtga acgccacga gttcgagatc gagggcgagg gcgagggccg ccctacgag       120 ggccacaaca ccgtgaagct gaaggtgacc aagggcggcc ccctgccctt cgcctgggac      180
atcctgtccc ccagttcca gtacggctcc aaggtgtacg tgaagcaccc cgccgacatc      240
cccgactaca agaagctgtc cttccccgag ggcttcaagt gggagcgcgt gatgaacttc      300
gaggacggcg gcgtggcgac cgtgacccaa gactcctccc tgcaggacgg ctgcttcatc      360
tacaaggtga gttcatcgg cgtgaacttc ccctccgacg gccccgtaat gcagaagaag      420
accatgggct gggaggcctc caccgagcgc ctgtaccccc gcgacggcgt gctgaagggc      480
gagacccaca aggccctgaa gctgaaggac ggcggccact acctggtgga gttcaagtcc      540
atctacatgg ccaagaagcc cgtgcagctg cccggctact actacgtgga cgccaagctg      600
gacatcacct cccacaacga ggactacacc atcgtggagc agtacgagcg caccgagggc      660
cgccaccacc tgttcctgta g                                                681
```

<210> SEQ ID NO 38
<211> LENGTH: 675
<212> TYPE: DNA
<213> ORGANISM: Discosoma species

<400> SEQUENCE: 38

```
atggcctcct ccgagaacgt catcaccgag ttcatgcgct tcaaggtgcg catggagggc      60
accgtgaacg gccacgagtt cgagatcgag ggcgagggcg agggccgccc ctacgagggc     120
cacaacaccg tgaagctgaa ggtgaccaag ggcggccccc tgcccttcgc ctgggacatc     180
ctgtccccc agttccagta cggctccaag gtgtacgtga agcacccgc cgacatcccc       240
gactacaaga agctgtcctt ccccgagggc ttcaagtggg agcgcgtgat gaacttcgag     300
gacgcggcg tggcgaccgt gacccaggac tcctccctgc aggacggctg cttcatctac      360
aaggtgaagt tcatcggcgt gaacttcccc tccgacggcc ccgtgatgca gaagaagacc     420
atgggctggg aggcctccac cgagcgcctg taccccgcg acggcgtgct gaagggcgag      480
acccacaagg ccctgaagct gaaggacggc ggccactacc tggtggagtt caagtccatc     540
tacatggcca agaagcccgt gcagctgccc ggctactact acgtggacgc caagctggac     600
atcacctccc acaacgagga ctacaccatc gtggagcagt acgagcgcac cgagggccgc     660
caccacctgt cctg                                                       675
```

```
<210> SEQ ID NO 39
<211> LENGTH: 707
<212> TYPE: DNA
<213> ORGANISM: Anemonia sulcata
```

<400> SEQUENCE: 39

```
ggatccgcct ccctgctgac cgagaccatg cccttcagga ccaccatcga gggcaccgtg      60
aacggccact acttcaagtg caccggcaag ggcgagggca ccccctcga gggcacccag      120
gagatgaaga tcgaggtgat cgaggcggc ccctgccct tcgccttcca catcctgtcc       180
acctcctgca tgtacggctc caaggccttc atcaagtacg tgtccggcat ccccgactac     240
ttcaagcagt ccctcccga gggcttcacc tgggagcgca ccaccacta cgaggacggc      300
ggcttcctga ccgcccacca ggacacctcc ctggacggcg actgcctggt gtacaaggtg    360
aagatcctgg gcaacaactt ccccgccgac ggccccgtga tgcagaacaa ggccggccgc    420
tgggagccct ccaccgagat cgtgtacgag gtggacggcg tgctgcgcgg ccagtccctg    480
atggccctgg agtgccccgg cggtcgccac ctgacctgcc acctgcacac cacctaccgc    540
tccaagaagc ccgcctccgc cctgaagatg cccggcttcc acttcgagga ccaccgcatc    600
gagatcctgg aggaggtgga aagggcaag tgctacaagc agtacgaggc cgccgtgggc      660
cgctactgcg acgccgcccc ctccaagctg ggccacaact gaagctt                   707
```

```
<210> SEQ ID NO 40
<211> LENGTH: 231
<212> TYPE: PRT
<213> ORGANISM: Anemonia sulcata
```

<400> SEQUENCE: 40

```
Ala Ser Leu Leu Thr Glu Thr Met Pro Phe Arg Thr Thr Ile Glu Gly
 1               5                  10                  15

Thr Val Asn Gly His Tyr Phe Lys Cys Thr Gly Lys Gly Glu Gly Asn
                20                  25                  30

Pro Leu Glu Gly Thr Gln Glu Met Lys Ile Glu Val Ile Glu Gly Gly
            35                  40                  45

Pro Leu Pro Phe Ala Phe His Ile Leu Ser Thr Ser Cys Met Tyr Gly
        50                  55                  60
```

Ser Lys Ala Phe Ile Lys Tyr Val Ser Gly Ile Pro Asp Tyr Phe Lys
 65                  70                  75                  80

Gln Ser Leu Pro Glu Gly Phe Thr Trp Glu Arg Thr Thr Thr Tyr Glu
                 85                  90                  95

Asp Gly Gly Phe Leu Thr Ala His Gln Asp Thr Ser Leu Asp Gly Asp
            100                 105                 110

Cys Leu Val Tyr Lys Val Lys Ile Leu Gly Asn Asn Phe Pro Ala Asp
        115                 120                 125

Gly Pro Val Met Gln Asn Lys Ala Gly Arg Trp Glu Pro Ser Thr Glu
    130                 135                 140

Ile Val Tyr Glu Val Asp Gly Val Leu Arg Gly Gln Ser Leu Met Ala
145                 150                 155                 160

Leu Glu Cys Pro Gly Gly Arg His Leu Thr Cys His Leu His Thr Thr
                165                 170                 175

Tyr Arg Ser Lys Lys Pro Ala Ser Ala Leu Lys Met Pro Gly Phe His
            180                 185                 190

Phe Glu Asp His Arg Ile Glu Ile Leu Glu Glu Val Glu Lys Gly Lys
        195                 200                 205

Cys Tyr Lys Gln Tyr Glu Ala Ala Val Gly Arg Tyr Cys Asp Ala Ala
    210                 215                 220

Pro Ser Lys Leu Gly His Asn
225                 230

<210> SEQ ID NO 41
<211> LENGTH: 699
<212> TYPE: DNA
<213> ORGANISM: Anemonia sulcata

<400> SEQUENCE: 41
atggcctcct tcctgaagaa gaccatgccc ttcaagacca ccatcgaggg caccgtgaac      60
ggccactact tcaagtgcac cggcaagggc gagggcaacc ccttcgaggg cacccaggag     120
atgaagatcg aggtgatcga gggcggcccc ctgcccttcg ccttccacat cctgtccacc     180
tcctgcatgt acggctccaa ggccttcatc aagtacgtgt ccggcatccc cgactacttc     240
aagcagtcct tccccgaggg cttcacctgg agcgcacca ccacctacga ggacggcggc      300
ttcctgaccg cccaccagga cacctccctg gacggcgact gcctggtgta caaggtgaag     360
atcctgggca caacttccc cgccgacggc cccgtgatgc agaacaaggc cggccgctgg      420
gagccctcca ccgagatcgt gtacgaggtg gacggcgtgc tgcgcggcca gtccctgatg     480
gccctgaagt gccccggcgg ccgccacctg acctgccacc tgcacaccac ctaccgctcc     540
aagaagcccg cctccgccct gaagatgccc ggcttccact cgaggacca ccgcatcgag      600 atcatggagg aggtggagaa gggcaagtgc tacaagcagt acgaggccgc cgtgggccgc     660
tactgcgacg ccgcccccctc caagctgggc cacaactga                            699

<210> SEQ ID NO 42
<211> LENGTH: 232
<212> TYPE: PRT
<213> ORGANISM: Anemonia sulcata

<400> SEQUENCE: 42

Met Ala Ser Phe Leu Lys Lys Thr Met Pro Phe Lys Thr Thr Ile Glu
  1               5                  10                  15

Gly Thr Val Asn Gly His Tyr Phe Lys Cys Thr Gly Lys Gly Glu Gly
             20                  25                  30

Asn Pro Phe Glu Gly Thr Gln Glu Met Lys Ile Glu Val Ile Glu Gly
            35                  40                  45

Gly Pro Leu Pro Phe Ala Phe His Ile Leu Ser Thr Ser Cys Met Tyr
        50                  55                  60

Gly Ser Lys Ala Phe Ile Lys Tyr Val Ser Gly Ile Pro Asp Tyr Phe
65                  70                  75                  80

Lys Gln Ser Phe Pro Glu Gly Phe Thr Trp Glu Arg Thr Thr Thr Tyr
                85                  90                  95

Glu Asp Gly Gly Phe Leu Thr Ala His Gln Asp Thr Ser Leu Asp Gly
            100                 105                 110

Asp Cys Leu Val Tyr Lys Val Lys Ile Leu Gly Asn Asn Phe Pro Ala
        115                 120                 125

Asp Gly Pro Val Met Gln Asn Lys Ala Gly Arg Trp Glu Pro Ser Thr
    130                 135                 140

Glu Ile Val Tyr Glu Val Asp Gly Val Leu Arg Gly Gln Ser Leu Met
145                 150                 155                 160

Ala Leu Lys Cys Pro Gly Gly Arg His Leu Thr Cys His Leu His Thr
                165                 170                 175

Thr Tyr Arg Ser Lys Lys Pro Ala Ser Ala Leu Lys Met Pro Gly Phe
            180                 185                 190

His Phe Glu Asp His Arg Ile Glu Ile Met Glu Glu Val Glu Lys Gly
        195                 200                 205

Lys Cys Tyr Lys Gln Tyr Glu Ala Ala Val Gly Arg Tyr Cys Asp Ala
    210                 215                 220

Ala Pro Ser Lys Leu Gly His Asn
225                 230

<210> SEQ ID NO 43
<211> LENGTH: 678
<212> TYPE: DNA
<213> ORGANISM: Artificial Sequence
<220> FEATURE:
<223> OTHER INFORMATION: hybrid construct

<400> SEQUENCE: 43
atgagctgca gcaagaacgt gatcaaggag ttcatgcggt tcaaggtgcg gatggagggc      60
accgtgaacg ccaccgagtt cgagatcaag ggcgagggcg agggccggcc ctacgagggc     120
cactgcagcg tgaagctcat ggtgaccaag ggcggccccc tcccttcgc cttcgacatc     180 ctcagccccc agttccagta cggcagcaag gtgtacgtga agcaccccgc cgacatcccc     240
gactacaaga agctcagctt ccccgagggc ttcaagtggg agcgggtgat gaacttcgag     300
gacggcggcg tggtgaccgt gagccaggac agcagcctca aggacggctg cttcatctac     360
gaggtgaagt tcatcggcgt gaacttcccc agcgacggcc ccgtgatgca gcggcggacc     420
cggggctggg aggccagcag cgagcggctc taccccgggg acggcgtgct caagggcgac     480
atccacatgg ccctccggct cgagggcggc ggccactacc tcgtggagtt caagagcatc     540
tacatggcca agaagcccgt gcagctcccc ggctactact acgtggacag caagctcgac     600
atcaccagcc acaacgagga ctacaccatc gtggagcagt acgagcggac cgagggccgg     660
caccacctct cctcctga                                                    678

<210> SEQ ID NO 44
<211> LENGTH: 225
<212> TYPE: PRT
<213> ORGANISM: Artificial Sequence
<220> FEATURE:

<223> OTHER INFORMATION: hybrid construct

<400> SEQUENCE: 44

```
Met Ser Cys Ser Lys Asn Val Ile Lys Glu Phe Met Arg Phe Lys Val
1               5                   10                  15
Arg Met Glu Gly Thr Val Asn Gly His Glu Phe Glu Ile Lys Gly Glu
            20                  25                  30
Gly Glu Gly Arg Pro Tyr Glu Gly His Cys Ser Val Lys Leu Met Val
        35                  40                  45
Thr Lys Gly Gly Pro Leu Pro Phe Ala Phe Asp Ile Leu Ser Pro Gln
    50                  55                  60
Phe Gln Tyr Gly Ser Lys Val Tyr Val Lys His Pro Ala Asp Ile Pro
65                  70                  75                  80
Asp Tyr Lys Lys Leu Ser Phe Pro Glu Gly Phe Lys Trp Glu Arg Val
                85                  90                  95
Met Asn Phe Glu Asp Gly Gly Val Val Thr Val Ser Gln Asp Ser Ser
            100                 105                 110
Leu Lys Asp Gly Cys Phe Ile Tyr Glu Val Lys Phe Ile Gly Val Asn
        115                 120                 125
Phe Pro Ser Asp Gly Pro Val Met Gln Arg Arg Thr Arg Gly Trp Glu
    130                 135                 140
Ala Ser Ser Glu Arg Leu Tyr Pro Arg Asp Gly Val Leu Lys Gly Asp
145                 150                 155                 160
Ile His Met Ala Leu Arg Leu Glu Gly Gly Gly His Tyr Leu Val Glu
                165                 170                 175
Phe Lys Ser Ile Tyr Met Ala Lys Lys Pro Val Gln Leu Pro Gly Tyr
            180                 185                 190
Tyr Tyr Val Asp Ser Lys Leu Asp Ile Thr Ser His Asn Glu Asp Tyr
        195                 200                 205
Thr Ile Val Glu Gln Tyr Glu Arg Thr Glu Gly Arg His His Leu Phe
    210                 215                 220
Leu
225
```

<210> SEQ ID NO 45
<211> LENGTH: 898
<212> TYPE: DNA
<213> ORGANISM: Discosoma species

<400> SEQUENCE: 45

```
gtcctcccaa gcagtggtat caacgcagag tacggggag tttcagccag tgacggtcag      60
tgacagggtg agccacttgg tataccaaca aaatgaggtc ttccaagaat gttatcaagg     120
agttcatgag gtttaaggtt cgcatggaag gaacggtcaa tgggcacgag tttgaaatag     180
aaggcgaagg agaggggagg ccatacgaag gccacaatac cgtaaagctt aaggtaacca     240
agggggggacc tttgccattt gcttgggata ttttgtcacc acaatttcag tatggaagca     300
aggtatatgt caagcaccct gccgacatac cagactataa aaagctgtca tttcctgaag     360
gatttaaatg ggaaagggtc atgaactttg aagacggtgg cgtcgttact gtaacccagg     420
attccagttt gcaggatggc tgtttcatct acaagtcaag ttcattggcg ttaactttc      480
cttccgatgg acctgttatg caaaagaaga caatgggctg ggaagccagc actgagcgtt     540
tgtatcctcg tgatggcgtg ttgaaggag agattcataa ggctctgaag ctgaagacg       600
gtggtcatta cctagttgaa ttcaaaagta tttacatggc aaagaagcct gtgcagctac     660
```

```
cagggtacta ctatgttgac tccaaactgg atataacaag ccacaacgaa gactatacaa    720
tcgttgagca gtatgaaaga accgagggac gccaccatct gttcctttaa ggctgaactt    780
ggctcagacg tgggtgagcg gtaatgacca caaaaggcag cgaagaaaaa ccatgatcgt    840 ttttttagg ttggcagcct gaaatcgtag gaaatacatc agaaatgtta caaacagg      898
```

<210> SEQ ID NO 46
<211> LENGTH: 205
<212> TYPE: PRT
<213> ORGANISM: Discosoma species

<400> SEQUENCE: 46

```
Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
                20                  25                  30

Gly Glu Gly Arg Pro Tyr Glu Gly His Asn Thr Val Lys Leu Lys Val
            35                  40                  45

Thr Lys Gly Gly Pro Leu Pro Phe Ala Trp Asp Ile Leu Ser Pro Gln
 50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Ser Ser Ser Leu Ala Leu Asn
        115                 120                 125

Phe Pro Ser Asp Gly Pro Val Met Gln Lys Lys Thr Met Gly Trp Glu
130                 135                 140

Ala Ser Thr Glu Arg Leu Gly His Tyr Leu Val Glu Phe Lys Ser Ile
145                 150                 155                 160

Ile Met Ala Lys Lys Pro Val Gln Leu Pro Gly Tyr Tyr Val Asp
                165                 170                 175

Ser Lys Leu Asp Ile Thr Ser His Asn Glu Asp Tyr Thr Ile Val Glu
            180                 185                 190

Gln Tyr Glu Arg Ser Glu Gly Arg His His Leu Phe Leu
        195                 200                 205
```

NUCLEIC ACIDS ENCODING CHROMOPHORES/FLUOROPHORES AND METHODS FOR USING THE SAME

CROSS REFERENCE TO RELATED APPLICATIONS

This application is a divisional application of application Ser. No. 10/006,922 filed on Dec. 4, 2001 and now issued as U.S. Pat. No. 7,166,444; which application is a continuation-in-part of Application Serial No. PCT/US00/28477 filed on Oct. 13, 2000; which application is a continuation-in-part of the following applications: application Ser. No. 09/418,529 filed Oct. 14, 1999 now abandoned; application Ser. No. 09/418,917 filed Oct. 15, 1999 now abandoned; application Ser. No. 09/418,922 filed Oct. 15, 1999 now abandoned; application Ser. No. 09/444,338 filed Nov. 19, 1999 now abandoned; application Ser. No. 09/444,341 filed Nov. 19, 1999 now abandoned; application Ser. No. 09/457,556 filed Dec. 9, 1999 now abandoned; application Ser. No. 09/458,477 filed Dec. 9, 1999 now abandoned; application Ser. No. 09/458,144 filed Dec. 9, 1999 now abandoned; and application Ser. No. 09/457,898 filed Dec. 9, 1999 now abandoned; all of which applications claim priority to application Ser. No. 09/210,330 filed Dec. 11, 1998 now abandoned; as well as application Ser. No. 60/211,627 filed on Jun. 14, 2000; application Ser. No. 60/211,687 filed on Jun. 14, 2000; application Ser. No. 60/211,609 filed on Jun. 14, 2000; application Ser. No. 60/211,626 filed on Jun. 14, 2000; application Ser. No. 60/211,880 filed on Jun. 14, 2000; application Ser. No. 60/211,607 filed on Jun. 14, 2000; application Ser. No. 60/211,766 filed on Jun. 14, 2000; application Ser. No. 60/211,888 filed on Jun. 14, 2000; and application Ser. No. 60/212,070 filed on Jun. 14, 2000; as well as International Application Serial No. PCT/US99/29405 filed Dec. 10, 1999, which application claims priority to application Ser. No. 09/210,330 filed Dec. 11, 1998 now abandoned; the disclosures of which application are incorporated in their entirety herein.

INTRODUCTION

1. Field of the Invention

The field of this invention is chromoproteins and fluorescent proteins.

2. Background of the Invention

Labeling is a tool for marking a protein, cell, or organism of interest and plays a prominent role in many biochemistry, molecular biology and medical diagnostic applications. A variety of different labels have been developed, including radiolabels, chromolabels, fluorescent labels, chemiluminescent labels, etc. However, there is continued interest in the development of new labels. Of particular interest is the development of new protein labels, including chromo- and/or fluorescent protein labels.

Relevant Literature

U.S. Patents of interest include: U.S. Pat. Nos. 6,066,476; 6,020,192; 5,985,577; 5,976,796; 5,968,750; 5,968,738; 5,958,713; 5,919,445; 5,874,304; and 5,491,084. International Patent Publications of interest include: WO 00/46233; WO 99/49019; and DE 197 18 640 A. Also of interest are: Anderluh et al., Biochemical and Biophysical Research Communications (1996) 220:437-442; Dove et al., Biological Bulletin (1995) 189:288-297; Fradkov et al., FEBS Lett. (2000) 479(3):127-30; Gurskaya et al., FEBS Lett., (2001) 507(1):16-20; Gurskaya et al., BMC Biochem. (2001) 2:6; Lukyanov, K., et al (2000) J Biol Chemistry 275(34):25879-25882; Macek et al., Eur. J. Biochem. (1995) 234:329-335; Martynov et al., J Biol. Chem. (2001) 276:21012-6; Matz, M. V., et al. (1999) Nature Biotechnol., 17:969-973; Terskikh et al., Science (2000) 290:1585-8; Tsien, Annual Rev. of Biochemistry (1998) 67:509-544; Tsien, Nat. Biotech. (1999) 17:956-957; Ward et al., J. Biol. Chem. (1979) 254:781-788; Wiedermann et al., Jarhrestagung der Deutschen Gesellschact fur Tropenokologie-gto. Ulm. 17-19 Feb. 1999. Poster P-4.20; Yarbrough et al., Proc Natl Acad Sci USA (2001) 98:462-7.

SUMMARY OF THE INVENTION

Nucleic acid compositions encoding novel chromo/fluoroproteins and mutants thereof, as well as the proteins encoded the same, are provided. The proteins of interest are proteins that are colored and/or fluorescent, where this feature arises from the interaction of two or more residues of the protein. The subject proteins are further characterized in that they are either obtained from non-bioluminescent Cnidarian, e.g., Anthozoan, species or are obtained from Anthozoan non-Pennatulacean (sea pen) species. Specific proteins of interest include proteins obtained from the following specific Anthozoan species: *Anemonia majano* (NFP-1), *Clavularia* sp. (NFP-2), *Zoanthus* sp. (NFP-3 & NFP-4), *Discosoma striata* (NFP-5), *Discosoma* sp. "red" (NFP-6), *Anemonia sulcata* (NFP-7), *Discosoma* sp "green" (NFP-8), and *Discosoma* sp. "magenta" (NFP-9). Also of interest are proteins that are substantially similar to, or mutants of, the above specific proteins. Also provided are fragments of the nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

BRIEF DESCRIPTION OF THE FIGURES

FIG. 1 provides the nucleotide and amino acid sequence of wild type amFP486 (NFP-1). (SEQ ID NO:01 & 02)

FIG. 2 provides the nucleotide and amino acid sequence of wild type cFP484 (NFP-2). (SEQ ID NO:03 & 04)

FIG. 3 provides the nucleotide and amino acid sequence of wild type zFP506 (NFP-3). (SEQ ID NO:05 & 06)

FIG. 4 provides the nucleotide and amino acid sequence of wild type zFP538 (NFP-4). (SEQ ID NO:07 & 08)

FIG. 5 provides the nucleotide and amino acid sequence of wild type dsFP483 NFP-5). (SEQ ID NO:09 & 10)

FIG. 6 provides the nucleotide and amino acid sequence of wild type drFP583 (NFP-6). (SEQ ID NO:11 & 12); as well as the nucleotide and amino acid sequence of an alternative version thereof.

FIG. 7 provides the nucleotide and amino acid sequence of wild type asFP600 (NFP-7). (SEQ ID NO:13 & 14)

FIG. 8 provides the nucleotide and amino acid sequence of wild type dgFP512 (NFP-8). (SEQ ID NO:15 & 16)

FIG. 9 provides the nucleotide and amino acid sequence of wild type dmFP592 (NFP-9). (SEQ ID NO:17 & 18)

FIG. 10 provides the nucleotide and amino acid sequence of mut32-NA (SEQ ID NO: 27 & 28)

FIG. 11 provides the nucleotide and amino acid sequence of FP3-NA (SEQ ID NO:29 & 30)

FIG. 12 provides the amino acid sequence of FP3-yellow (SEQ ID NO:31)

FIG. 13 provides the amino acid sequence of FP3-Yellow bright (SEQ ID NO:32)

FIG. 14 provides the nucleotide and amino acid sequence of NFP4-NA (SEQ ID NO:33 & 34).

FIG. 15 provides additional sequence information of NFP-6 mutants.

FIG. 16 provides the nucleotide sequence of humanized NFP-6. (SEQ ID NO:35)

FIG. 17 provides the nucleotide sequence of mutant E5-NA. (SEQ ID NO:36)

FIG. 18 provides the nucleotide sequence of mutant E57. (SEQ ID NO:37)

FIG. 19 provides the nucleotide sequence of mutant E57-NA (SEQ ID NO:38)

FIG. 20 provides the nucleotide and amino acid sequence of mutant FP7-NA (SEQ ID NO:39 & 40).

FIG. 21 provides the nucleotide and amino acid sequence of humanized FP7. (SEQ ID NO:41 & 42).

FIG. 22 provides the nucleotide and amino acid sequence of humanized 6/9Q (SEQ ID NO:43 & 44).

DEFINITIONS

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

As used herein, the term "hybridization" refers to the process of association of two nucleic acid strands to form an antiparallel duplex stabilized by means of hydrogen bonding between residues of the opposite nucleic acid strands.

The term "oligonucleotide" refers to a short (under 100 bases in length) nucleic acid molecule.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to heterologous promoter or enhancer elements and whose product may be assayed easily and quantifiably when the construct is introduced into tissues or cells.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243 (1969), 3552-59 is used.

The term "immunologically active" defines the capability of the natural, recombinant or synthetic chromo/fluorescent protein, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal. The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a polypeptide, an antibody, or a host cell that is in an environment different from that in which the polynucleotide, the polypeptide, the antibody, or the host cell naturally occurs.

Bioluminescence (BL) is defined as emission of light by living organisms that is well visible in the dark and affects visual behavior of animals (See e.g., Harvey, E. N. (1952). *Bioluminescence*. New York: Academic Press; Hastings, J. W. (1995). Bioluminescence. In: *Cell Physiology* (ed. by N. Speralakis). pp. 651-681. New York: Academic Press.; Wilson, T. and Hastings, J. W. (1998). Bioluminescence. *Annu Rev Cell Dev Biol* 14, 197-230.). Bioluminescence does not include so-called ultra-weak light emission, which can be detected in virtually all living structures using sensitive luminometric equipment (Murphy, M. E. and Sies, H.(1990). Visible-range low-level chemiluminescence in biological systems. *Meth. Enzymol.* 186, 595-610; Radotic, K, Radenovic, C, Jeremic, M. (1998.) Spontaneous ultra-weak bioluminescence in plants: origin, mechanisms and properties. *Gen Physiol Biophys* 17, 289-308), and from weak light emission which most probably does not play any ecological role, such as the glowing of bamboo growth cone (Totsune, H., Nakano, M., Inaba, H.(1993). Chemiluminescence from bamboo shoot cut. *Biochem. Biophys. Res Comm.* 194, 1025-1029) or emission of light during fertilization of animal eggs (Klebanoff, S. J., Froeder, C. A., Eddy, E. M., Shapiro, B. M. (1979). Metabolic similarities between fertilization and phagocytosis. Conservation of peroxidatic mechanism. *J. Exp. Med.* 149, 938-953; Schomer, B. and Epel, D. (1998). Redox changes during fertilization and maturation of marine invertebrate eggs. *Dev Biol* 203, 1-11).

DESCRIPTION OF THE SPECIFIC EMBODIMENTS

Nucleic acid compositions encoding novel chromo/fluoroproteins and mutants thereof, as well as the proteins encoded the same, are provided. The proteins of interest are proteins that are colored and/or fluorescent, where this feature arises from the interaction of two or more residues of the protein. The subject proteins are further characterized in that they are either obtained from non-bioluminescent Cnidarian, e.g., Anthozoan, species or are obtained from non-Pennatulacean (sea pen) Anthozoan species. Specific proteins of interest include proteins obtained from the following specific Anthozoan species: *Anemonia majano* (NFP-1), *Clavularia* sp. (NFP-2), *Zoanthus* sp. (NFP-3 & NFP-4), *Discosoma striata* (NFP-5), *Discosoma* sp. "red" (NFP-6), *Anemonia sulcata* (NFP-7), *Discosoma* sp "green" (NFP-8), and *Discosoma* sp. "magenta" (NFP-9). Also of interest are proteins that are substantially similar to, or mutants of, the above specific proteins. Also provided are fragments of the nucleic acids and the peptides encoded thereby, as well as antibodies to the subject proteins, and transgenic cells and organisms that include the subject nucleic acid/protein compositions. The subject protein and nucleic acid compositions find use in a variety of different applications. Finally, kits for use in such applications, e.g., that include the subject nucleic acid compositions, are provided.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, methodologies and other invention components that are described in the publications which might be used in connection with the presently described invention.

In further describing the subject invention, the subject nucleic acid compositions will be described first, followed by a discussion of the subject protein compositions, antibody compositions and transgenic cells/organisms. Next a review of representative methods in which the subject proteins find use is provided.

Nucleic Acid Compositions

As summarized above, the subject invention provides nucleic acid compositions encoding chromo- and fluoroproteins and mutants thereof, as well as fragments and homologues of these proteins. By chromo and/or fluorescent protein is meant a protein that is colored, i.e., is pigmented, where the protein may or may not be fluorescent, e.g., it may exhibit low, medium or high fluorescence upon irradiation with light of an excitation wavelength. In any event, the subject proteins of interest are those in which the colored characteristic, i.e., the chromo and/or fluorescent characteristic, is one that arises from the interaction of two or more residues of the protein, and not from a single residue, more specifically a single side chain of a single residue, of the protein. As such, fluorescent proteins of the subject invention do not include proteins that exhibit fluorescence only from residues that act by themselves as intrinsic fluors, i.e., tryptophan, tyrosine and phenylalanine. As such, the fluorescent proteins of the subject invention are fluorescent proteins whose fluorescence arises from some structure in the protein that is other than the above specified single residues, e.g., it arises from an interaction of two or more residues.

By nucleic acid composition is meant a composition comprising a sequence of DNA having an open reading frame that encodes a chromo/fluoro polypeptide of the subject invention, i.e., a chromo/fluoroprotein gene, and is capable, under appropriate conditions, of being expressed as a chromo/fluoro protein according to the subject invention. Also encompassed in this term are nucleic acids that are homologous, substantially similar or identical to the nucleic acids of the present invention. Thus, the subject invention provides genes and coding sequences thereof encoding the proteins of the subject invention, as well as homologs thereof. The subject nucleic acids are present in other than their natural environment, e.g., they are isolated, present in enriched amounts, etc., from their naturally occurring environment, e.g., the organism from which they are obtained.

The nucleic acids are further characterized in that they encode proteins that are either from: (1) non-bioluminescent species, often non-bioluminescent Cnidarian species, e.g., non-bioluminescent Anthozoan species; or (2) from Anthozoan species that are not Pennatulacean species, i.e., that are not sea pens. As such, the nucleic acids may encode proteins from bioluminescent Anthozoan species, so long as these species are not Pennatulacean species, e.g., that are not Renillan or Ptilosarcan species. Specific nucleic acid compositions of interest are those that encode proteins (and mutants thereof) from the following specific Anthozoan species: *Anemonia majano*, *Clavularia* sp., *Zoanthus* sp., *Discosoma striata*, *Discosoma* sp. "red", *Anemonia sulcata*, *Discosoma* sp "green", and *Discosoma* sp. "magenta." Each of these particular types of nucleic acid compositions of interest is now discussed in greater detail individually.

*Anemonia majano* (NFP-1; AmCyan; RCFP-1)

In these embodiments, the nucleic acid compositions are found in, derived from, or are mutants, homologues of, a nucleic acid found in an organism from the Anthozoan Sub-class Zoantharia, often Order Actiniaria, more often Sub-order Endomyaria, usually Family Actiniidae, and more usually Genus *Anemonia*, where in many embodiments, the organism is *Anemonia majano*, where the specific wild type protein of interest is amFP486 (i.e., NFP-1; RCFP-1). The wild type cDNA coding sequence for amFP486 is provided in SEQ ID NO: 01. In addition to nucleic acids encoding the wild type protein and fragments thereof, also of interest are nucleic acids that encode homologues and mutants of the wild type protein. Specific mutants of interest include, but are not limited to: Mut15, Mut32, and FP1-NA (a non-aggregating mutant), where these specific mutants are further described in the experimental section, infra.

*Clavularia* sp. (NFP-2, RCPF-2)

In these embodiments, the nucleic acid compositions are found in, derived from, or are mutants or homologues of, nucleic acids found in Anthozoan organisms from Sub-class Alcyonaria, often Order Stolonifera, and more often the Family Clavulariidae, where the organism is usually from the Genus *Clavularia*, and in certain embodiments, the organism is *Clavularia* sp., where the specific wild type fluorescent protein of interest is cFP484 (i.e., NFP-2; RCFP-2). The wild type cDNA coding sequence for cFP484 is provided in SEQ ID NO: 03. In addition to nucleic acids encoding the wild type sequence and fragments thereof, also of interest are nucleic acids that encode homologues and mutants of the wild type protein. Specific mutants of interest include, but are not limited to: Δ19 cFP484 and Δ38 cFP484, where these specific mutants are further described in the experimental section, infra.

*Zoanthus* sp. I (NFP-3; ZsGreen; RCFP-3)

In these embodiments, the nucleic acid compositions are found in, derived from, or are mutants or homologues of, nucleic acids found in Anthozoan organisms from Sub-class Zoantharia, often Order Zoanthidea, more often Sub-order Brachycnemia, usually Family Zoanthidae, and more usually Genus *Zoanthus*, where in certain embodiments, the organism is *Zoanthus* sp., where the specific wild type fluorescent protein of interest is zFP506 (i.e., NFP-3; RCFP-3). The wild type cDNA coding sequence for zFP506 is provided in SEQ ID NO: 05. In addition to nucleic acids encoding the wild type sequence and fragments thereof, also of interest are nucleic acids that encode homologues and mutants of the wild type protein. Specific mutants of interest include, but are not limited to: N66M; NFP-3NA (a non-aggregating mutant); yellow; yellow bright, etc., where these specific mutants are further described in the experimental section, infra.

*Zoanthus* sp. II (NFP-4; ZsYellow; RCFP-4)

In these embodiments, the nucleic acid compositions are found in, derived from, or are mutants or homologues of, nucleic acids found in Anthozoan organisms from Sub-class Zoantharia, often Order Zoanthidea, more often Sub-order Brachycnemia, usually Family Zoanthidae, and more usually Genus *Zoanthus*, where in certain embodiments, the organism is *Zoanthus* sp., where the specific wild type fluorescent protein of interest is zFP538 (NFP4; RCFP-4). The wild type cDNA coding sequence for zFP538 is provided in SEQ ID NO. 07. In addition to nucleic acids encoding the wild type sequence and fragments thereof, also of interest are nucleic acids that encode homologues and mutants of the wild type protein. Specific mutants of interest include, but are not limited to: M129V; FP4-NA (a non-aggregating mutant); green; etc., where these specific mutants are further described in the experimental section, infra.

*Discosoma striata* (NFP-5; RCFP-5)

In these embodiments, the nucleic acid compositions are found in, derived from, or are mutants or homologues of, nucleic acids found in Anthozoan organisms from Sub-class Zoantharia, often Order Corallimopharia, more often Family Discosomatidae, and usually Genus *Discosoma*, where in certain embodiments, the organism is *Discosoma striata*, where the specific wild type fluorescent protein of interest is dsFP483 (NFP-5; RCFP-5). The wild type cDNA coding sequence for dsFP483 is provided in SEQ ID NO: 09. In addition to nucleic acids encoding the wild type sequence and fragments thereof, also of interest are nucleic acids that encode homologues and mutants of the wild type protein.

*Discosoma* sp. "red" (NFP-6; RCFP-6; DsRed; DsRed2)

In these embodiments, the nucleic acid compositions are found in, derived from, or are mutants or homologues of, nucleic acids found in Anthozoan organisms from Sub-class Zoantharia, often Order Corallimopharia, more often Family Discosomatidae, and usually Genus *Discosoma*, where in certain embodiments, the organism is *Discosoma* sp. "red"., where the specific wild type fluorescent protein of interest is drFP583 (NFP-6; RCFP-6). The wild type cDNA coding sequence for drFP583 is provided in SEQ ID NO: 11. In addition to nucleic acids encoding the wild type sequence and fragments thereof, also of interest are nucleic acids that encode homologues and mutants of the wild type protein. Specific mutants of interest include, but are not limited to: E5, E5-NA (a non-aggregating mutant); E8, E5up, E5down, E57, FP6-NA (a non-aggregating mutant), AG4, AG45, E83, 6/9 Q, 6/9 Q-NA, 6/92G; etc., where these specific mutants are further described in the experimental section, infra.

*Anemonia sulcata* (NFP-7; AsRed; RCFP-7)

In these embodiments, the nucleic acid compositions are found in, derived from, or are mutants or homologues of, nucleic acids found in Anthozoan organisms from Sub-class Zoantharia, often Order Actiniaria, more often Sub-Order Endomyaria, usually Family Actiniidae, and more usually Genus *Anemonia*, e.g., where in certain embodiments the organism is *Anemonia sulcata*, where the specific wild type fluorescent protein of interest is asFP600 (NFP-7; RCFP-7). The wild type cDNA coding sequence for asFP600 is provided in SEQ ID NO:14. In addition to nucleic acids encoding the wild type sequence and fragments thereof, also of interest are nucleic acids that encode homologues and mutants of the wild type protein. Specific mutants of interest include, but are not limited to: Mut1; Mut35-5/Mut1; FP7-NA (a non-aggregating mutant), etc., where these specific mutants are further described in the experimental section, infra.

*Discosoma* sp "green" (NFP-8; RCFP-8)

In these embodiments, the nucleic acid compositions are found in, derived from, or are mutants or homologues of, nucleic acids found in Anthozoan organisms from Sub-class Zoantharia, often Order Corallimopharia, more often Family Discosomatidae, and usually Genus *Discosoma*, where in certain embodiments, the organism is *Discosoma* sp. "green"., where the specific wild type fluorescent protein of interest is dgFP512 (NFP-8; RCFP-8). The wild type cDNA coding sequence for dgFP512 is provided in SEQ ID NO: 15. In addition to nucleic acids encoding the wild type sequence and fragments thereof, also of interest are nucleic acids that encode homologues and mutants of the wild type protein.

*Discosoma* sp. "magenta" (NFP-9; RCFP-9)

In these embodiments, the nucleic acid compositions are found in, derived from, or are mutants or homologues of, nucleic acids found in Anthozoan organisms from Sub-class Zoantharia, often Order Corallimopharia, more often Family Discosomatidae, and usually Genus Discosomam where in certain embodiments, the organism is *Discosoma* sp. "magenta"., where the specific wild type fluorescent protein of interest is dmFP592 (NFP-9; RCFP-9). The wild type cDNA coding sequence for dmFP592 is provided in SEQ ID NO: 17. In addition to nucleic acids encoding the wild type sequence and fragments thereof, also of interest are nucleic acids that encode homologues and mutants of the wild type protein.

In addition to the above described specific nucleic acid compositions, also of interest are homologues of the above sequences. With respect to homologues of the subject nucleic acids, the source of homologous genes may be any species of plant or animal or the sequence may be wholly or partially synthetic. In certain embodiments, sequence similarity between homologues is at least about 20%, sometimes at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17). The sequences provided herein are essential for recognizing related and homologous nucleic acids in database searches. Of particular interest in certain embodiments are nucleic acids of substantially the same length as the nucleic acid identified as SEQ ID NOS: 01, 03, 05, 07, 09, 11, 13, 15, or 17, where by substantially the same length is meant that any difference in length does not exceed about 20 number %, usually does not exceed about 10 number % and more usually does not exceed about 5 number %; and have sequence identity to any of these sequences of at least about 90%, usually at least about 95% and more usually at least about 99% over the entire length of the nucleic acid. In many embodiments, the nucleic acids have a sequence that is substantially similar (i.e. the same as) or identical to the sequences of SEQ ID NOS: 01, 03, 05, 07, 09, 11, 13, 15, or 17. By substantially similar is meant that sequence identity will generally be at least about 60%, usually at least about 75% and often at least about 80, 85, 90, or even 95%.

Also provided are nucleic acids that encode the proteins encoded by the above described nucleic acids, but differ in sequence from the above described nucleic acids due to the degeneracy of the genetic code.

Also provided are nucleic acids that hybridize to the above described nucleic acid under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 μg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

Nucleic acids encoding mutants of the proteins of the invention are also provided. Mutant nucleic acids can be generated by random mutagenesis or targeted mutagenesis, using well-known techniques which are routine in the art. In some embodiments, chromo-or fluorescent proteins encoded by nucleic acids encoding homologues or mutants have the same fluorescent properties as the wild-type fluorescent protein. In other embodiments, homologue or mutant nucleic acids encode chromo- or fluorescent proteins with altered spectral properties, as described in more detail herein.

One category of mutant that is of particular interest is the non-aggregating mutant. In many embodiments, the non-aggregating mutant differs from the wild type sequence by a mutation in the N-terminus that modulates the charges appearing on side groups of the N-terminus residues, e.g., to reverse or neutralize the charge, in a manner sufficient to produce a non-aggregating mutant of the naturally occurring protein or mutant, where a particular protein is considered to be non-aggregating if it is determined be non-aggregating using the assay reported in U.S. Patent Application Ser. No. 60/270,983, the disclosure of which is herein incorporated by reference. More specifically, basic residues located near the N-termini of the proteins are substituted, e.g., Lys and Arg residues close to the N-terminus are substituted with negatively charged or neutral residues. Specific non-aggregating mutants of interest include, but are not limited to: FP1-NA; FP3-NA; FP4-NA; FP6-NA; E5-NA; 6/9Q-NA; 7A-NA; and the like, where these particular non-aggregating mutants are further described infra.

Another category of mutant of particular interest is the modulated oligomerization mutant. A mutant is considered to be a modulated oligomerization mutant if its oligomerization properties are different as compared to the wild type protein. For example, if a particular mutant oligomerizes to a greater or lesser extent than the wild type, it is considered to be an oligomerization mutant. Of particular interest are oligomerization mutants that do not oligomerize, i.e., are monomers under physiological (e.g., intracellular) conditions, or oligomerize to a lesser extent that the wild type, e.g., are dimers or trimers under intracellular conditions.

Nucleic acids of the subject invention may be cDNA or genomic DNA or a fragment thereof. In certain embodiments, the nucleic acids of the subject invention include one or more of the open reading frames encoding specific fluorescent proteins and polypeptides, and introns, as well as adjacent 5' and 3' non-coding nucleotide sequences involved in the regulation of expression, up to about 20 kb beyond the coding region, but possibly further in either direction. The subject nucleic acids may be introduced into an appropriate vector for extrachromosomal maintenance or for integration into a host genome, as described in greater detail below.

The term "cDNA" as used herein is intended to include all nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest comprises the nucleic acid present between the initiation codon and the stop codon, as defined in the listed sequences, including all of the introns that are normally present in a native chromosome. It may further include 5' and 3' un-translated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject proteins. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least about 15 nt, usually at least about 18 nt or about 25 nt, and may be at least about 50 nt. In some embodiments, the subject nucleic acid molecules may be about 100 nt, about 200 nt, about 300 nt, about 400 nt, about 500 nt, about 600 nt, about 700 nt, or about 720 nt in length. The subject nucleic acids may encode fragments of the subject proteins or the full-length proteins, e.g., the subject nucleic acids may encode polypeptides of about 25 aa, about 50 aa, about 75 aa, about 100 aa, about 125 aa, about 150 aa, about 200 aa, about 210 aa, about 220 aa, about 230 aa, or about 240 aa, up to the entire protein.

The subject nucleic acids are isolated and obtained in substantial purity, generally as other than an intact chromosome. Usually, the DNA will be obtained substantially free of other nucleic acid sequences that do not include a nucleic acid of the subject invention or fragment thereof, generally being at least about 50%, usually at least about 90% pure and are typically "recombinant", i.e. flanked by one or more nucleotides with which it is not normally associated on a naturally occurring chromosome.

The subject polynucleotides (e.g., a polynucleotide having a sequence of SEQ ID NOS: 01 to 17 etc.), the corresponding cDNA, the full-length gene and constructs of the subject polynucleotides are provided. These molecules can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual, 2nd Ed.*, (1989) Cold Spring Harbor Press, Cold Spring Harbor, N.Y., and under current regulations described in United States Dept. of HHS, National Institute of Health (NIH) Guidelines for Recombinant DNA Research.

Also provided are nucleic acids that encode fusion proteins of the subject proteins, or fragments thereof, which are fused to a second protein, e.g., a degradation sequence, a signal peptide, etc. Fusion proteins may comprise a subject polypeptide, or fragment thereof, and a non-Anthozoan polypeptide ("the fusion partner") fused in-frame at the N-terminus and/or C-terminus of the subject polypeptide. Fusion partners include, but are not limited to, polypeptides that can bind antibody specific to the fusion partner (e.g., epitope tags); antibodies or binding fragments thereof; polypeptides that provide a catalytic function or induce a cellular response; ligands or receptors or mimetics thereof; and the like. In such fusion proteins, the fusion partner is generally not naturally associated with the subject Anthozoan portion of the fusion protein, and is typically not an Anthozoan protein or derivative/fragment thereof, i.e., it is not found in Anthozoan species.

Also provided are constructs comprising the subject nucleic acids inserted into a vector, where such constructs may be used for a number of different applications, including propagation, protein production, etc. Viral and non-viral vectors may be prepared and used, including plasmids. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the subject proteins. For expression, the gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, a subject polynucleotide, e.g., as set forth in SEQ ID NOS:01; 03; 05; 07; 09; 11; 13; 15 or 17, is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described above.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, e.g. COS 7 cells, HEK 293, CHO, Xenopus Oocytes, etc., may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (*USA*) (1983) 80:21-25; and Siebenlist et al., *Cell* (1980) 20:269.

Yeast. Expression systems in yeast include those described in Hinnen et al., *Proc. Natl. Acad. Sci.* (*USA*) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154: 737; Van den Berg et al., *Bio/Technology*(1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284-289; Tilburn et al., *Gene* (1983) 26:205-221; Yelton et al.; *Proc. Natl. Acad. Sci.* (*USA*) (1984) 81:1470-1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409; Maeda et al., *Nature* (1985) 315:592-594; Lebacq-Verheyden et al., *Mol. Cell. Biol.* (1988) 8:3129; Smith et al., *Proc. Natl. Acad. Sci.* (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of the subject proteins without manipulation of the encoding nucleic acid itself, but instead through integration of a regulatory sequence into the genome of cell that already includes a gene encoding the desired protein, as described in the above incorporated patent documents.

Also provided are homologs of the subject nucleic acids. Homologs are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM-sodium chloride/1.5 mM sodium citrate). Nucleic acids having a region of substantial identity to the provided sequences, e.g. allelic variants, genetically altered versions of the gene, etc., bind to the provided sequences under stringent hybridization conditions. By using probes, particularly labeled probes of DNA sequences, one can isolate homologous or related genes.

Also of interest are promoter elements of the subject genomic sequences, where the sequence of the 5' flanking region may be utilized for promoter elements, including enhancer binding sites, e.g., that provide for regulation of expression in cells/tissues where the subject proteins gene are expressed.

Also provided are small DNA fragments of the subject nucleic acids, which fragments are useful as primers for PCR, hybridization screening probes, etc. Larger DNA fragments, i.e., greater than 100 nt are useful for production of the encoded polypeptide, as described in the previous section. For use in geometric amplification reactions, such as geometric PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of Anthozoan protein gene expression in the sample.

The subject nucleic acids, including flanking promoter regions and coding regions, may be mutated in various ways known in the art to generate targeted changes in promoter strength, sequence of the encoded protein, properties of the encoded protein, including fluorescent properties of the encoded protein, etc. The DNA sequence or protein product of such a mutation will usually be substantially similar to the sequences provided herein, e.g. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon, e.g. of stretches of 10, 20, 50, 75, 100, 150 or more aa residues. Techniques for in vitro mutagenesis of cloned genes are known. Examples of protocols for site specific mutagenesis may be found in Gustin et al. (1993), *Biotechniques* 14:22; Barany (1985), *Gene* 37:111-23; Colicelli et al. (1985), *Mol. Gen. Genet.* 199:537-9; and Prentki et al. (1984), *Gene* 29:303-13. Methods for site specific mutagenesis can be found in Sambrook et al., *Molecular Cloning: A Laboratory Manual*, CSH Press 1989, pp. 15.3-15.108; Weiner et al. (1993), *Gene* 126:3541; Sayers et al. (1992), *Biotechniques* 13:592-6; Jones and Winistorfer (1992), *Biotechniques* 12:528-30; Barton et al. (1990), *Nucleic Acids Res* 18:7349-55; Marotti and Tomich (1989), *Gene Anal Tech.* 6:67-70; and Zhu (1989), *Anal Biochem* 177:120-4. Such mutated nucleic acid derivatives may be used to study structure-function relationships of a particular chromo/fluorescent protein, or to alter properties of the protein that affect its function or regulation.

Of particular interest in many embodiments is the following specific mutation protocol, which protocol finds use in mutating chromoproteins (e.g., colored proteins that have little if any fluorescence) into fluorescent mutants. In this protocol, the sequence of the candidate protein is aligned with the amino acid sequence of *Aequorea victoria* wild type GFP, according to the protocol reported in Matz et al., "Fluorescent proteins from non-bioluminescent Anthozoa species," Nature Biotechnology (October 1999) 17: 969-973. Residue 148 of the aligned chromoprotein is identified and then changed to Ser, e.g., by site directed mutagenesis, which results in the production of a fluorescent mutant of the wild type chromoprotein. See e.g., NFP-7 described below, which wild type protein is a chromoprotein that is mutated into a fluorescent protein by substitution of Ser for the native Ala residue at position 148.

Also of interest are humanized versions of the subject nucleic acids. As used herein, the term "humanized" refers to changes made to the a nucleic acid sequence to optimize the codons for expression of the protein in human cells (Yang et al., *Nucleic. Acids Research* 24 (1996), 4592-4593). See also U.S. Pat. No. 5,795,737 which describes humanization of proteins, the disclosure of which is herein incorporated by reference.

Protein/Polypeptide Compositions

Also provided by the subject invention are chromo- and/or fluorescent proteins and mutants thereof, as well as polypeptide compositions related thereto. As the subject proteins are chromoproteins, they are colored proteins, which may be fluorescent, low or non-fluorescent. As used herein, the terms chromoprotein and fluorescent protein do not include luciferases, such as Renilla luciferase, and refer to any protein that is pigmented or colored and/or fluoresces when irradiated with light, e.g., white light or light of a specific wavelength (or narrow band of wavelengths such as an excitation wavelength). The term polypeptide composition as used herein refers to both the full-length protein, as well as portions or fragments thereof. Also included in this term are variations of the naturally occurring protein, where such variations are homologous or substantially similar to the naturally occurring protein, and mutants of the naturally occurring proteins, as described in greater detail below. The subject polypeptides are present in other than their natural environment.

In many embodiments, the subject proteins have an absorbance maximum ranging from about 300 to 700, usually from about 350 to 650 and more usually from about 400 to 600 nm. Where the subject proteins are fluorescent proteins, by which is meant that they can be excited at one wavelength of light following which they will emit light at another wavelength, the excitation spectra of the subject proteins typically ranges from about 300 to 700, usually from about 350 to 650 and more usually from about 400 to 600 nm while the emission spectra of the subject proteins typically ranges from about 400 to 800, usually from about 425 to 775 and more usually from about 450 to 750 nm. The subject proteins generally have a maximum extinction coefficient that ranges from about 10,000 to 50,000 and usually from about 15,000 to 45,000. The subject proteins typically range in length from about 150 to 300 and usually from about 200 to 300 amino acid residues, and generally have a molecular weight ranging from about 15 to 35 kDa, usually from about 17.5 to 32.5 kDa.

In certain embodiments, the subject proteins are bright, where by bright is meant that the chromoproteins and their fluorescent mutants can be detected by common methods (e.g., visual screening, spectrophotometry, spectrofluorometry, fluorescent microscopy, by FACS machines, etc.) Fluorescence brightness of particular fluorescent proteins is determined by its quantum yield multiplied by maximal extinction coefficient. Brightness of a chromoproteins may be expressed by its maximal extinction coefficient.

In certain embodiments, the subject proteins fold rapidly following expression in the host cell. By rapidly folding is meant that the proteins achieve their tertiary structure that gives rise to their chromo- or fluorescent quality in a short period of time. In these embodiments, the proteins fold in a period of time that generally does not exceed about 3 days, usually does not exceed about 2 days and more usually does not exceed about 1 day.

Specific proteins of interest are chromo/fluoroproteins (and mutants thereof) from the following specific Anthozoan species: *Anemonia majano, Clavularia* sp., *Zoanthus* sp., *Zoanthus* sp., *Discosoma striata, Discosoma* sp. "red", *Anemonia sulcata, Discosoma* sp "green", *Discosoma* sp. "magenta." Each of these particular types of polypeptide compositions of interest is now discussed in greater detail individually.

*Anemonia majano* (NFP-1; AmCyan)

In many embodiments, the proteins have an absorbance maximum ranging from about 250 to 650, usually from about 400 to 500 and more usually from about 440 to 480 nm while the emission maximum typically ranges from about 270 to 670, usually from about 420 to 520 and more usually from about 460 to 500 nm. The subject proteins typically range in length from about 200 to 250, usually from about 210 to 240 amino acid residues, and generally have a molecular weight ranging from about 20 to 30, usually from about 22.50 to 27.50 kDa. Of particular interest in many embodiments is amFP486 (NFP-1), which has an amino acid sequence as shown in SEQ ID NO:02. Also of interest are mutants of this sequence, where specific mutants of interest include, but are not limited to: Mut15, Mut32, and FP1-NA (a non-aggregating mutant), where these specific mutants are further described in the experimental section, infra.

*Clavularia* sp. (NFP-2)

In certain embodiments, the proteins have an absorbance maximum that typically ranges from about 250 to 650, usually from about 400 to 500 and more usually from about 440 to 480 nm and an emission maximum that typically ranges from about 270 to 670, usually from about 420 to 520 and more usually from about 460 to 500 nm, where the subject proteins typically range in length from about 225 to 300, usually from about 250 to 275 amino acid residues, and generally have a molecular weight ranging from about 25 to 35, usually from about 27.50 to 32.50 kDa. Of particular interest is the cFP484 protein having the sequence shown in SEQ ID NO:04. Specific mutants of interest include, but are not limited to: Δ19 cFP484 and Δ38 cFP484, where these specific mutants are further described in the experimental section, infra.

*Zoanthus* sp I. (NFP-3; ZsGreen)

In many embodiments, the proteins have an absorbance maximum that typically ranges from about 300 to 700, usually from about 450 to 550 and more usually from about 480 to 510 nm and an emission maximum that typically ranges from about 320 to 720, usually from about 470 to 570 and more usually from about 500 to 530 nm. The subject proteins typically range in length from about 200 to 250, usually from about 220 to 240 amino acid residues, and generally have a molecular weight ranging from about 20 to 30, usually from about 22.50 to 27.50 kDa. Of particular interest is the protein zFP506 (NFP-3) which has an amino acid sequence as shown in SEQ ID NO:06. Specific mutants of interest include, but are not limited to: N66M; FP-3NA (a non-aggregating mutant); yellow; yellow bright, etc., where these specific mutants are further described in the experimental section, infra.

*Zoanthus* sp. II (NFP-4; ZsYellow)

In many embodiments, the proteins have an excitation maximum that typically ranges from about 300 to 650, usually from about 475 to 575 and more usually from about 500 to 550 nm and an emission maximum that typically ranges from about 310 to 660, usually from about 485 to 585 and more usually from about 510 to 560 nm. The subject proteins typically range in length from about 200 to 250, usually from about 220 to 240 amino acid residues, and generally have a molecular weight ranging from about 20 to 30, usually from about 22.50 to 27.50 kDa. Specific mutants of interest include, but are not limited to: M129V; NFP4-NA (a non-aggregating mutant); green; etc., where these specific mutants are further described in the experimental section, infra.

*Discosoma striata* (NFP-5)

In many embodiments, the proteins have an excitation maximum that typically ranges from about 240 to 640, usually from about 500 to 600 and more usually from about 530 to 560 nm and an emission maximum that typically ranges from about 280 to 680, usually from about 540 to 640 and more usually from about 570 to 600 nm. The subject proteins typically range in length from about 200 to 250, usually from about 220 to 240 amino acid residues, and generally have a molecular weight ranging from about 20 to 30, usually from about 22.50 to 27.50 kDa. Of particular interest in many embodiments is the protein dsFP483 (NFP-5) which has an amino acid sequence as shown in SEQ ID NO:10, as well as mutants thereof.

*Discosoma* sp. "red" (NFP-6; DsRed; DsRed2)

In many embodiments, the proteins have an absorbance maximum that typically ranges from about 250 to 750, usually from about 500 to 600 and more usually from about 540 to 580 nm and have an emission maximum that typically ranges from about 275 to 775, usually from about 525 to 625 and more usually from about 565 to 605 nm. The subject proteins typically range in length from about 200 to 250, usually from about 220 to 240 amino acid residues, and generally have a molecular weight ranging from about 20 to 30, usually from about 22.50 to 27.50 kDa. Of particular interest is the drFP583 (NFP-6) protein that has an amino acid sequence as shown in SEQ ID NO:12. Specific mutants of interest include, but are not limited to: E5, E5-NA (a non-aggregating mutant), E8, E5up, E5down, E57, FP6-NA (a non-aggregating mutant), AG4, AG45, E83, 6/9 Q, 6/9 Q-NA, 6/92G, etc., where these specific mutants are further described in the experimental section, infra.

*Anemonia sulcata* (NFP-7; AsRed)

In many embodiments, the proteins have an absorbance maximum that typically ranges from about 370 to 770, usually from about 520 to 620 and more usually from about 560 to 580 nm and an emission maximum that typically ranges from about 395 to 795, usually from about 545 to 645 and more usually from about 585 to 605 nm. The subject proteins typically range in length from about 200 to 250, usually from about 220 to 240 amino acid residues, and generally have a molecular weight ranging from about 20 to 30, usually from about 22.50 to 27.50 kDa. Of particular interest is the asFP595(asFP600) (NFP-7) protein that has an amino acid sequence as shown in SEQ ID NO:14. Specific mutants of interest include, but are not limited to: Mut1; Mut35-5/Mut1; FP7-NA (a non-aggregating mutant), etc., where these specific mutants are further described in the experimental section, infra.

*Discosoma* sp "Green" (NFP-8)

In many embodiments, the proteins have an absorbance maximum that typically ranges from about 300 to 700, usually from about 450 to 650 and more usually from about 490 to 510 nm and an emission maximum that typically ranges from about 310 to 710, usually from about 460 to 660 and more usually from about 500 to 520 nm. The subject proteins typically range in length from about 200 to 250, usually from about 220 to 240 amino acid residues, and generally have a molecular weight ranging from about 20 to 30, usually from about 22.50 to 27.50 kDa. Of particular interest is the dgFP512 protein (NFP-8) protein that has an amino acid sequence as shown in SEQ ID NO:16, as well as mutants thereof.

*Discosoma* sp. "Magenta" (NFP-9)

In many embodiments, the proteins have an absorbance maximum that typically ranges from about 375 to 775, usually from about 525 to 625 and more usually from about 560 to 590 nm and an emission maximum that typically ranges from about 395 to 795, usually from about 545 to 645 and more usually from about 580 to 610 nm. The subject proteins typically range in length from about 200 to 250, usually from about 220 to 240 amino acid residues, and generally have a molecular weight ranging from about 20 to 30, usually from about 22.50 to 27.50 kDa. Of particular interest is the dmFP592 (NFP-9) protein that has an amino acid sequence as shown in SEQ ID NO:18, as well as mutants thereof.

Homologs or proteins (or fragments thereof) that vary in sequence from the above provided specific amino acid sequences of the subject invention, i.e., SEQ ID NOS: 02; 04; 06; 08; 10; 12; 14;16 or 18, are also provided. By homolog is meant a protein having at least about 10%, usually at least about 20% and more usually at least about 30%, and in many embodiments at least about 35%, usually at least about 40% and more usually at least about 60% amino acid sequence identity to the protein of the subject invention, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151-153. (Parameters used are ktuple 1, gap, penalty 3, window, 5 and diagonals saved 5). In many embodiments, homologues of interest have much higher sequence identify, e.g., 65%, 70%, 75%, 80%, 85%, 90% or higher.

Also provided are proteins that are substantially identical to the wild type protein, where by substantially identical is meant that the protein has an amino acid sequence identity to the sequence of wild type protein of at least about 60%, usually at least about 65% and more usually at least about 70%, where in some instances the identity may be much higher, e.g., 75%, 80%, 85%, 90%, 95% or higher.

In many embodiments, the subject homologues have structural features found in the above provided specific sequences, where such structural features include the β-can fold.

Proteins which are mutants of the above-described naturally occurring proteins are also provided. Mutants may retain biological properties of the wild-type (e.g., naturally occurring) proteins, or may have biological properties which differ from the wild-type proteins. The term "biological property" of the subject proteins includes, but is not limited to, spectral properties, such as absorbance maximum, emission maximum, maximum extinction coefficient, brightness (e.g., as compared to the wild-type protein or another reference protein such as green fluorescent protein from *A. Victoria*), and the like; in vivo and/or in vitro stability (e.g., half-life); etc. Mutants include single amino acid changes, deletions of one or more amino acids, N-terminal truncations, C-terminal truncations, insertions, etc.

Mutants can be generated using standard techniques of molecular biology, e.g., random mutagenesis, and targeted mutagenesis. Several mutants are described herein. Given the guidance provided in the Examples, and using standard techniques, those skilled in the art can readily generate a wide variety of additional mutants and test whether a biological property has been altered. For example, fluorescence intensity can be measured using a spectrophotometer at various excitation wavelengths.

Those proteins of the subject invention that are naturally occurring proteins are present in a non-naturally occurring environment, e.g., are separated from their naturally occurring environment. In certain embodiments, the subject proteins are present in a composition that is enriched for the subject protein as compared to its naturally occurring environment. For example, purified protein is provided, where by purified is meant that the protein is present in a composition that is substantially free of non-chromo/fluoroprotein proteins of interest, where by substantially free is meant that less than 90%, usually less than 60% and more usually less than 50% of the composition is made up of non-chromoproteins or mutants thereof of interest. The proteins of the subject invention may also be present as an isolate, by which is meant that the protein is substantially free of other proteins and other naturally occurring biologic molecules, such as oligosaccharides, polynucleotides and fragments thereof, and the like, where the term "substantially free" in this instance means that less than 70%, usually less than 60% and more usually less than 50% of the composition containing the isolated protein is some other naturally occurring biological molecule. In certain embodiments, the proteins are present in substantially pure form, where by "substantially pure form" is meant at least 95%, usually at least 97% and more usually at least 99% pure.

In addition to the naturally occurring proteins, polypeptides that vary from the naturally occurring proteins, e.g., the mutant proteins described above, are also provided. Generally such polypeptides include an amino acid sequence encoded by an open reading frame (ORF) of the gene encoding the subject wild type protein, including the full length protein and fragments thereof, particularly biologically active fragments and/or fragments corresponding to functional domains, and the like; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to the subject protein of at least about 10 aa, and usually at least about 15 aa, and in many embodiments at least about 50 aa in length. In some embodiments, the subject polypeptides are about 25 aa, about 50 aa, about 75 aa, about 100 aa, about 125 aa, about 150 aa, about 200 aa, about 210 aa, about 220 aa, about 230 aa, or about 240 aa in length, up to the entire protein. In some embodiments, a protein fragment retains all or substantially all of a biological property of the wild-type protein.

The subject proteins and polypeptides may be obtained from naturally occurring sources or synthetically produced. For example, wild type proteins may be derived from biological sources which express the proteins, e.g., non-bioluminescent Cnidarian, e.g., Anthozoan, species, such as the specific ones listed above. The subject proteins may also be derived from synthetic means, e.g., by expressing a recombinant gene or nucleic acid coding sequence encoding the protein of interest in a suitable host, as described above. Any convenient protein purification procedures may be employed, where suitable protein purification methodologies are described in Guide to Protein Purification, (Deuthser ed.) (Academic Press, 1990). For example, a lysate may prepared from the original source and purified using HPLC, exclusion chromatography, gel electrophoresis, affinity chromatography, and the like.

Antibody Compositions

Also provided are antibodies that specifically bind to the subject fluorescent proteins. Suitable antibodies are obtained by immunizing a host animal with peptides comprising all or a portion of the subject protein. Suitable host animals include mouse, rat sheep, goat, hamster, rabbit, etc. The origin of the protein immunogen will generally be a Cnidarian species, specifically a non-bioluminescent Cnidarian species, such as an Anthozoan species or a non-Petalucean Anthozoan species. The host animal will generally be a different species than the immunogen, e.g., mice, etc.

The immunogen may comprise the complete protein, or fragments and derivatives thereof. Preferred immunogens comprise all or a part of the protein, where these residues contain the post-translation modifications found on the native target protein. Immunogens are produced in a variety of ways known in the art, e.g., expression of cloned genes using conventional recombinant methods, isolation from Anthozoan species of origin, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also of interest in certain embodiments are humanized antibodies. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Transgenics

The subject nucleic acids can be used to generate transgenic, non-human plants or animals or site specific gene modifications in cell lines. Transgenic cells of the subject invention include on or more nucleic acids according to the subject invention present as a transgene, where included within this definition are the parent cells transformed to include the transgene and the progeny thereof. In many embodiments, the transgenic cells are cells that do not normally harbor or contain a nucleic acid according to the subject invention. In those embodiments where the transgenic cells do naturally contain the subject nucleic acids, the nucleic acid will be present in the cell in a position other than its natural location, i.e. integrated into the genomic material of the cell at a non-natural location. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

Transgenic organisms of the subject invention include cells and multicellular organisms, e.g., plants and animals, that are endogenous knockouts in which expression of the endogenous gene is at least reduced if not eliminated. Transgenic organisms of interest also include cells and multicellular organisms, e.g., plants and animals, in which the protein or variants thereof is expressed in cells or tissues where it is not normally expressed and/or at levels not normally present in such cells or tissues.

DNA constructs for homologous recombination will comprise at least a portion of the gene of the subject invention, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc. Representative examples of the use of transgenic animals include those described infra.

Transgenic plants may be produced in a similar manner. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants are also reviewed in Plant Biochemistry and Molecular Biology (eds Lea & Leegood, John Wiley & Sons) (1993) pp 275-295. In brief, a suitable plant cell or tissue is harvested, depending on the nature of the plant species. As such, in certain instances, protoplasts will be isolated, where such protoplasts may be isolated from a variety of different plant tissues, e.g. leaf, hypocty1, root, etc. For protoplast isolation, the harvested cells are incubated in the presence of cellulases in order to remove the cell wall, where the exact incubation conditions vary depending on the type of plant and/or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells, where a variety of different techniques are available for such introduction. With isolated protoplasts, the opportunity arise for introduction via DNA-mediated gene transfer protocols, including: incubation of the protoplasts with naked DNA, e.g. plasmids, comprising the exogenous coding sequence of interest in the presence of polyvalent cations, e.g. PEG or PLO; and electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, e.g. auxins and cytokinins. With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained. Instead of the naked DNA approaches described above, another convenient method of producing transgenic plants is *Agrobacterium* mediated transformation. With *Agrobacterium* mediated transformation, co-integrative or binary vectors comprising the exogenous DNA are prepared and then introduced into an appropriate *Agrobacterium* strain, e.g. *A. tumefaciens*. The resultant bacteria are then incubated with prepared protoplasts or tissue explants, e.g. leaf disks, and a callus is produced. The callus is then grown under selective conditions, selected and subjected to growth media to induce root and shoot growth to ultimately produce a transgenic plant.

Utility

The subject chromoproteins and fluorescent mutants thereof find use in a variety of different applications, where the applications necessarily differ depending on whether the protein is a chromoprotein or a fluorescent protein. Representative uses for each of these types of proteins will be described below, where the follow described uses are merely representative and are in no way meant to limit the use of the subject proteins to those described below.

Chromoproteins

The subject chromoproteins of the present invention find use in a variety of different applications. One application of interest is the use of the subject proteins as coloring agents which are capable of imparting color or pigment to a particular composition of matter. Of particular interest in certain embodiments are non-toxic chromoproteins. The subject chromoproteins may be incorporated into a variety of different compositions of matter, where representative compositions of matter include: food compositions, pharmaceuticals, cosmetics, living organisms, e.g., animals and plants, and the like. Where used as a coloring agent or pigment, a sufficient amount of the chromoprotein is incorporated into the composition of matter to impart the desired color or pigment thereto. The chromoprotein may be incorporated into the composition of matter using any convenient protocol, where the particular protocol employed will necessarily depend, at least in part, on the nature of the composition of matter to be colored. Protocols that may be employed include, but are not limited to: blending, diffusion, friction, spraying, injection, tattooing, and the like.

The chromoproteins may also find use as labels in analyte detection assays, e.g., assays for biological analytes of interest. For example, the chromoproteins may be incorporated into adducts with analyte specific antibodies or binding fragments thereof and subsequently employed in immunoassays for analytes of interest in a complex sample, as described in U.S. Pat. No. 4,302,536; the disclosure of which is herein incorporated by reference. Instead of antibodies or binding fragments thereof, the subject chromoproteins or chromogenic fragments thereof may be conjugated to ligands that specifically bind to an analyte of interest, or other moieties, growth factors, hormones, and the like; as is readily apparent to those of skill in the art.

In yet other embodiments, the subject chromoproteins may be used as selectable markers in recombinant DNA applications, e.g., the production of transgenic cells and organisms, as described above. As such, one can engineer a particular transgenic production protocol to employ expression of the subject chromoproteins as a selectable marker, either for a successful or unsuccessful protocol. Thus, appearance of the color of the subject chromoprotein in the phenotype of the transgenic organism produced by a particular process can be used to indicate that the particular organism successfully harbors the transgene of interest, often integrated in a manner that provides for expression of the transgene in the organism. When used a selectable marker, a nucleic acid encoding for the subject chromoprotein can be employed in the transgenic generation process, where this process is described in greater detail supra. Particular transgenic organisms of interest where the subject proteins may be employed as selectable markers include transgenic plants, animals, bacteria, fungi, and the like.

In yet other embodiments, the chromoproteins (and fluorescent proteins) of the subject invention find use in sunscreens, as selective filters, etc., in a manner similar to the uses of the proteins described in WO 00/46233.

Fluorescent Proteins

The subject fluorescent proteins of the present invention (as well as other components of the subject invention described above) find use in a variety of different applications, where such applications include, but are not limited to, the following. The first application of interest is the use of the subject proteins in fluorescence resonance energy transfer (FRET) applications. In these applications, the subject proteins serve as donor and/or acceptors in combination with a second fluorescent protein or dye, e.g., a fluorescent protein as described in Matz et al., Nature Biotechnology (October 1999) 17:969-973, a green fluorescent protein from *Aequoria victoria* or fluorescent mutant thereof, e.g., as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference, other fluorescent dyes, e.g., coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemilumescent dyes, e.g., luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference. Specific examples of where FRET assays employing the subject fluorescent proteins may be used include, but are not limited to: the detection of protein-protein interactions, e.g., mammalian two-hybrid system, transcription factor dimerization, membrane protein multimerization, multiprotein complex formation, etc., as a biosensor for a number of different events, where a peptide or protein covalently links a FRET fluorescent combination including the subject fluorescent proteins and the linking peptide or protein is, e.g., a protease specific substrate, e.g., for caspase mediated cleavage, a linker that undergoes conformational change upon receiving a signal which increases or decreases FRET, e.g., PKA regulatory domain (cAMP-sensor), phosphorylation, e.g., where there is a phosphorylation site in the linker or the linker has binding specificity to phosphorylated/dephosphorylated domain of another protein, or the linker has $Ca^{2+}$ binding domain. Representative fluorescence resonance energy transfer or FRET applications in which the subject proteins find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; 5,439,797; the disclosures of which are herein incorporated by reference.

The subject fluorescent proteins also find use as biosensors in prokaryotic and eukaryotic cells, e.g. as $Ca^{2+}$ ion indicator; as pH indicator, as phorphorylation indicator, as an indicator of other ions, e.g., magnesium, sodium, potassium, chloride and halides. For example, for detection of Ca ion, proteins containing an EF-hand motif are known to translocate from the cytosol to membranes upon $Ca^{2+}$ binding. These proteins contain a myristoyl group that is buried within the molecule by hydrophobic interactions with other regions of the protein. Binding of $Ca^{2+}$ induces a conformational change exposing the myristoyl group which then is available for the insertion into the lipid bilayer (called a "$Ca^{2+}$-myristoyl switch"). Fusion of such a EF-hand containing protein to Fluorescent Proteins (FP) could make it an indicator of intracellular $Ca^{2+}$ by monitoring the translocation from the cytosol to the plasma membrane by confocal microscopy. EF-hand proteins suitable for use in this system include, but are not limited to: recoverin (1-3), calcineurin B, troponin C, visinin, neurocalcin, calmodulin, parvalbumin, and the like. For pH, a system based on hisactophilins may be employed. Hisactophilins are myristoylated histidine-rich proteins known to exist in *Dictyostelium*. Their binding to actin and acidic lipids is sharply pH-dependent within the range of cytoplasmic pH variations. In living cells membrane binding seems to override the interaction of hisactophilins with actin filaments. At pH 6.5 they locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By fusing FPs (Fluoresent Proteins) to hisactophilin the intracellular distribution of the fusion protein can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells. Substantial pH-dependent redistribution of hisactophilin-FP from the cytosol to the plasma membrane occurs within 1-2 min and reaches a steady state level after 5-10 min. The reverse reaction takes place on a similar time scale. As such, hisactophilin-fluorescent protein fusion protein that acts in an analogous fashion can be used to monitor cytosolic pH changes in real time in live mammalian cells. Such methods have use in high throughput applications, e.g., in the measurement of pH changes as consequence of growth factor receptor activation (e.g. epithelial or platelet-derived growth factor) chemotactic stimulation/cell locomotion, in the detection of intracellular pH changes as second messenger, in the monitoring of intracellular pH in pH manipulating experiments, and the like. For detection of PKC activity, the reporter system exploits the fact that a molecule called MARCKS (myristoylated alanine-rich C kinase substrate) is a PKC substrate. It is anchored to the plasma membrane via myristoylation and a stretch of positively charged amino acids (ED-domain) that bind to the negatively charged plasma membrane via electrostatic interactions. Upon PKC activation the ED-domain becomes phosphorylated by PKC, thereby becoming negatively charged, and as a consequence of electrostatic repulsion MARCKS translocates from the plasma membrane to the cytoplasm (called the "myristoyl-electrostatic switch"). Fusion of the N-terminus of MARCKS ranging from the myristoylation motif to the ED-domain of MARCKS to fluorescent proteins of the present invention makes the above a detector system for PKC activity. When phosphorylated by PKC, the fusion protein translocates from the plasma membrane to the cytosol. This translocation is followed by standard fluorescence microscopy or confocal microscopy e.g. using the Cellomics technology or other High Content Screening systems (e.g. Universal Imaging Corp./Becton Dickinson). The above reporter system has application in High Content Screening, e.g., screening for PKC inhibitors, and as an indicator for PKC activity in many screening scenarios for potential reagents interfering with this signal transduction pathway. Methods of using fluorescent proteins as biosensors also include those described in U.S. Pat. Nos. 972,638; 5,824,485 and 5,650,135 (as well as the references cited therein) the disclosures of which are herein incorporated by reference.

The subject fluorescent proteins also find use in applications involving the automated screening of arrays of cells expressing fluorescent reporting groups by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth, etc.; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B1 and cyclinE; protease cleavage with subsequent movement of cleaved substrate, phospholipids, with markers for intracellular structures such as endoplasmic reticulum, Golgi apparatus, mitochondria, peroxisomes, nucleus, nucleoli, plasma membrane, histones, endosomes, lysosomes, microtubules, actin) as tools for High Content Screening: co-localization of other fluorescent fusion proteins with these localization markers as indicators of movements of intracellular fluorescent fusion proteins/peptides or as marker alone; and the like. Examples of applications involving the automated screening of arrays of cells in which the subject fluorescent proteins find use include: U.S. Pat. No. 5,989,835; as well as WO/0017624; WO 00/26408; WO 00/17643; and WO 00/03246; the disclosures of which are herein incorporated by reference.

The subject fluorescent proteins also find use in high through-put screening assays. The subject fluorescent proteins are stable proteins with half-lives of more than 24 h. Also provided are destabilized versions of the subject fluorescent proteins with shorter half-lives that can be used as transcription reporters for drug discovery. For example, a protein according to the subject invention can be fused with a putative proteolytic signal sequence derived from a protein with shorter half-life, e.g., PEST sequence from the mouse ornithine decarboxylase gene, mouse cyclin B1 destruction box and ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject fluorescent proteins for drug screening, e.g., AP1, NFAT, NFkB, Smad, STAT, p53, E2F, Rb, myc, CRE, ER, GR and TRE, and the like.

The subject proteins can be used as second messenger detectors, e.g., by fusing the subject proteins to specific domains: e.g., PKCgamma Ca binding domain, PKCgamma DAG binding domain, SH2 domain and SH3 domain, etc.

Secreted forms of the subject proteins can be prepared, e.g. by fusing secreted leading sequences to the subject proteins to construct secreted forms of the subject proteins, which in turn can be used in a variety of different applications.

The subject proteins also find use in fluorescence activated cell sorting applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo marker in animals (e.g., transgenic animals). For example, expression of the subject protein can be driven by tissue specific promoters, where such methods find use in research for gene therapy, e.g., testing efficiency of transgenic expression, among other applications. A representative application of fluorescent proteins in transgenic animals that illustrates this class of applications of the subject proteins is found in WO 00/02997, the disclosure of which is herein incorporated by reference.

Additional applications of the subject proteins include: as markers following injection into cells or animals and in calibration for quantitative measurements (fluorescence and protein); as markers or reporters in oxygen biosensor devices for monitoring cell viability; as markers or labels for animals, pets, toys, food, etc.; and the like.

The subject fluorescent proteins also find use in protease cleavage assays. For example, cleavage inactivated fluorescence assays can be developed using the subject proteins, where the subject proteins are engineered to include a protease specific cleavage sequence without destroying the fluorescent character of the protein. Upon cleavage of the fluorescent protein by an activated protease fluorescence would sharply decrease due to the destruction of a functional chromophor. Alternatively, cleavage activated fluorescence can be developed using the subject proteins, where the subject proteins are engineered to contain an additional spacer sequence in close proximity/or inside the chromophor. This variant would be significantly decreased in its fluorescent activity, because parts of the functional chromophor would be divided by the spacer. The spacer would be framed by two identical protease specific cleavage sites. Upon cleavage via the activated protease the spacer would be cut out and the two residual "subunits" of the fluorescent protein would be able to reassemble to generate a functional fluorescent protein. Both of the above types of application could be developed in assays for a variety of different types of proteases, e.g., caspases, etc.

The subject proteins can also be used is assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes also allowing colocalization of membrane proteins in specific phospholipid rafts can be accomplished with the subject proteins. For example, the PH domain of GRP1 has a high affinity to phosphatidylinositol tri-phosphate (PIP3) but not to PIP2. As such, a fusion protein between the PH domain of GRP1 and the subject proteins can be constructed to specifically label PIP3 rich areas in biological membranes.

Yet another application of the subject proteins is as a fluorescent timer, in which the switch of one fluorescent color to another (e.g. green to red) concomitant with the ageing of the fluorescent protein is used to determine the activation/deactivation of gene expression, e.g., developmental gene expression, cell cycle dependent gene expression, circadian rhythm specific gene expression, and the like The antibodies of the subject invention, described above, also find use in a number of applications, including the differentiation of the subject proteins from other fluorescent proteins.

Kits

Also provided by the subject invention are kits for use in practicing one or more of the above described applications, where the subject kits typically include elements for making the subject proteins, e.g., a construct comprising a vector that includes a coding region for the subject protein. The subject kit components are typically present in a suitable storage medium, e.g., buffered solution, typically in a suitable container. Also present in the subject kits may be antibodies to the provided protein. In certain embodiments, the kit comprises a plurality of different vectors each encoding the subject protein, where the vectors are designed for expression in different environments and/or under different conditions, e.g., constitutive expression where the vector includes a strong promoter for expression in mammalian cells, a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

Experimental

I. Wild-Type Anthozoan Proteins

The following table summarizes the properties of nine specific wild type Anthozoan proteins of the subject invention:

TABLE I

| NFP | Species | Identifier | Absorb. Max. Nm | Emission Max. Nm | Maximum Extinction Coeff. | Relative Quantum Yield* | Relative Brightness** |
|---|---|---|---|---|---|---|---|
| 1 | *Anemonia majano* | amFP486 | 458 | 486 | 40,000 | 0.3 | 0.43 |
| 2 | *Clavularia* sp. | cFP484 | 456 | 484 | 35,300 | 0.6 | 0.77 |
| 3 | *Zoanthus* sp. | zFP506 | 496 | 506 | 35,600 | 0.79 | 1.02 |
| 4 | *Zoanthus* sp. | zFP538 | 528 | 538 | 20,200 | 0.52 | 0.38 |
| 5 | *Discosoma striata* | dsFP483 | 443 | 483 | 23,900 | 0.57 | 0.50 |
| 6 | *Discosoma* sp. "red" | drFP583 | 558 | 583 | 22,500 | 0.29 | 0.24 |
| 7 | *Anemonia sulcata* | asFP600 | 572 | 596 | 56,200 | <0.001 | — |
| 8 | *Discosoma* sp "green" | dgFP512 | 502 | 512 | 20,360 | 0.3 | 0.21 |
| 9 | *Discosoma* sp. "magenta" | dmFP592 | 573 | 593 | 21,800 | 0.11 | 0.09 |

*relative quantum yield was determined as compared to the quantum yield of *A. victoria* GFP.
**relative brightness is extinction coefficient multiplied by quantum yield divided by the same value for *A. victoria* GFP.

The sequences of the above wild type proteins and cDNAs encoding the same are provided in FIGS. 1 to 9.

II. amFP486 Characterization and Mutants thereof (NFP-1; AmCyan)

A. Construction of amFP486 Mutants

Two mutants of amFP486 were generated, Mut15 and Mut32. Mut32 has the following amino acid substitutions relative to the wildtype: K65M according to GFP alignment numbering as described in Matz et al., supra, or K68M according to self numbering. Mut15 has the following amino acid substitutions relative to the wildtype: K65L according to GFP alignment numbering as described in Matz et al., supra, or K68L according to self numbering. Compared with wildtype amFP486 nucleic acid sequence, Mut15 has the following point mutations: A101G, T129C, AAA 202-204TTG, and C240T. (i.e., A to G at position 101 (numbered from beginning of ATG), T to C at position 129; AAA to TTG at positions 202-204; C to T at position 240).

Table 2 lists the spectral properties of Mut15 and Mut32.

In addition, a non aggregating mutant of Mut 32 was prepared, where this mutant had the following substitutions: K6E, K68M as compared to wild type. The orf nucleotide and amino acid sequences of this mutant are provided in FIG. 10.

Additional mutants of NFP-1 include (according to GFP numbering): Y66H; Y66W; A167M; and A167I.

B. Construction and Functional Analysis of Vectors

Mut32 DNA was amplified via PCR and reconstructed to EGFP-N1 backbone with BamHI and NotI restriction enzyme sites. This vector has the same multiple cloning sites as EGFP-N1 (Clontech Laboratories, Palo Alto, Calif.).

Functional tests of the generated vectors were performed by transient transfection in 293 cells. After 24-hour expression, brighter fluorescent intensity and less photobleaching of pCNFPMut32-N1 were observed by microscopy when compared with pECFP-N1 side by side.

Mut32 has fast folding and bright fluorescent intensity, which makes it useful for number of applications. Some fusion proteins were tested, such as PKC-gamma-CNFP. PKC was observed to translocate from cytosol to the plasma membrane when cells were treated with PMA (phorbol 12-myristate 13-acetate).

TABLE 2

Spectral Properties of the Isolated Mut15 and Mut32

| Species | NFP Name | Absorbance Maximum nm | Emission Maximum nm | Maximum Extinction Coeff. | Quantum Yield | Relative Brightness* |
|---|---|---|---|---|---|---|
| *Anemonia majano* | Mut15 | 460 | 485 | 53,400 | 0.32 | 0.78 |
| *Anemonia majano* | Mut32 | 466 | 488 | 36,000 | 0.42 | 0.69 |

*relative brightness is extinction coefficient multiplied by quantum yield divided by the same value for *A. victoria* GFP.

C. Generation of Destabilized amFP486 Vectors as Transcription Reporters

Three destabilized amFP486 vectors were constructed by fusing different mouse ODC degradation domains such as d1, d2 and d376 to the C-terminal of wild type amFP486 as described in U.S. Pat. No. 6,306,600; the disclosure of which is herein incorporated by reference. The vectors were constructed in the EGFP-N1 backbone.

Vectors of pCRE-d1CNFP and pNF-κB-d1CNFP were constructed by placing d1CNFP downstream of cAMP response element (CRE) or NF-κB response element, respectively. Expression of d1CNFP is up-regulated upon activation of these response elements.

D. Functional Analysis of Destabilized amFP486

Functional tests of the destabilized amFP486 were performed by transient transfection in 293 cells. After 24-hour expression, the fluorescent intensity was decreased gradually from d2, d1 and d376 because of the fusion with different mouse ODC degradation domains. After 4-hour treatment with protein synthesis inhibitor cycloheximide, d2 fluorescent intensity did not change very much; however, d1 fluorescent intensity decreased further 50% of its original intensity. The half-life of d1 is around 4 hours.

MODCd1 is a valuable tool for application as a transcription reporter. However, compared with EGFP-d1 (1-hour half-life), pCNFP-MODCd1 half-life (4 hours) is still long, so further mutagenesis for MODC degradation domain is still needed for shorter half-life version.

Functional tests of vectors pCRE-d1CNFP and pNF-κB-d1CNFP were performed by transient transfection in HEK 293 cells. 16 hours post transfection, 10 μm forskolin was added to induce CRE and 100 ng/ml TNF-alpha was added to induce NF-κB for 6 hours. Expression of d1CNFP was analyzed using FACS Calibur. Up to 7 fold increase of fluorescence in forskolin induced CRE activation and 4 fold increase of fluorescence in TNF-α induced NF-KB activation was observed.

E. Construction and Functional Test for Humanized Mut32 (phCNFP-N1)

Since mammalian expression is a very popular tool, a human favored codon version of this mutant is needed for better expression in mammalian cells. To generate humanized Mut32, the Mut 32 sequence was first changed to human favored codon and 23 oligos (12F and 11R) were designed. Next, four rounds of PCR amplification were performed, each round for 20 cycles. PCR cycle was designed as follows: 94° C. for 1 min; 94° C. for 1 min; 40° C. for 1 min; and 72° C. for 1 min. The four rounds were: for $1^{st}$ round, mixing 2 μl each of every 4 oligos (60 bp), 5 μl buffer, 1 μl pfu, 1 μl dNTP to make total volume of 50 μl. After 20 cycles of PCR, 5 sets of 150 bp and 1 set of 4 last oligos of 90 bp products were obtained. For $2^{nd}$ round, mixing new crude PCR products 10 μl each, 5 μl buffer, 1 μl pfu, 1 μl dNTP to make total volume of 50 μl. After 20 cycles of PCR, 2 sets of 270 bp and 1 set of 210 bp PCR products were obtained. For $3^{rd}$ round, mixing new crude PCR products. After 20 cycles of PCR, 1 set of 510 bp and 1 set of 450 bp products were obtained. For $4^{th}$ round, mixing new crude products. After 20 cycles of PCR, final PCR product (690 bp) was obtained. Further PCR amplification was performed using 1F and 11R primers. As a result, humanized Mut32 was generated. This humanized Mut32 was constituted into EGFP-N1 backbone.

F. Expression of Wildtype and Mutant amFP486 in Mammalian Cells

The original plasmid amFP486 DNAs (wildtype, Mut15 and Mut32 in pQE30) were used to construct N1 version of amFP486 wildtype, Mut-15 and Mut32 as described above. The DNAs were inserted into E. coli DH5α. HEK 293 cells were transferred with each of the three N1 constructs using Calcium Phosphate method (Clontech product #K2051-1).

The fluorescent intensity of the transfected cells was analyzed on FACS using FL1 (510/30) detecting channel. Five samples were analyzed in parallel for each construct. The observed mean value of FL1 fluorescent intensity of the M1 population of each sample is summarized in Table 3. It shows that the average of the mean value of each construct (Wildtype, Mut15, and Mut32) has no significant difference.

TABLE 3

| | FL1 Fluorescent Intensity of M1 Population | | |
|---|---|---|---|
| Sample # | Wildtype | Mut15 | Mut32 |
| 1 | 82.84 | 106.95 | 84.51 |
| 2 | 77.52 | 108.73 | 91.41 |
| 3 | 111.85 | 97.08 | 91.30 |
| 4 | 113.06 | 90.16 | 98.16 |
| 5 | 104.95 | 86.34 | 111.44 |
| Mean | 98.04 | 97.85 | 95.36 |

G. Generation and Expression of Fusion Protein Mut15-mdm2

The Mut15-mdm2 fusion was generated by the following steps: first, mdm2 DNA was obtained by amplifying human Marathon cDNA library (Burke's Lymphoma) using primers:

ATGTGCAATACCAACATGTCTGTACC (SEQ ID No. 19) and

CTAGGGGAAATAAGTTAGCAC (SEQ ID No. 20); secondly, the purified PCR product was then amplified with primers:

GGAATTCCAGCCATGGTGTGCAATAC-CAACATGTCTGTACC (SEQ ID No. 21) and

TCCCCCGGGGGGAAATAAGTTAGCAC (SEQ ID No. 22)

in order to add Kozac sequence and restriction sites; thirdly, the purified PCR product from step 2 was digested with EcoR I and Sma I and inserted into EcoR I and SmaI of NFP1Mut15-N1 vector (this vector was generated using BamH I and Not I sites of the pEGFP-N1 backbone). The generated Mut15-mdm2 fusion was then expressed in HEK293 cells.

H. Comparison of the Protein Fluorescent Intensity

PQE30 amFP486 wildtype, Mut15 and Mut32 were transformed into DH5α. The bacteria grew in the presence of 1 mM IPTG overnight to induce the protein expression. Cells were lysed in 100 mM Tris, pH8.0 by sonication. Cell lysate was collected after centrifuge at 3000 rpm for 15 minutes at room temperature. The proteins were purified with TALON™ Metal Affinity Resin (Clontech Laboratories, Inc., Palo Alto, Calif.). Briefly, after the protein was absorbed on the resin, the beads were washed in stepwise with first wash, then first elution (50 mM imidazole) and second elution (200 mM imidazole) in 100 mM Tris-HCl, pH 8.0. The protein is found mostly in the second step elution. It was found that Mut32 has the highest bacterial expression level, while Mut15 has the lowest.

Samples of each elution fraction were run on SDS-PAGE to check the purity of the proteins. Both wildtype amFP486 and Mut32 show a single band, while Mut15 has two more minor bands with higher molecular weight (data not shown).

The protein concentration (fractionII-2) was checked and measured by Bradford assay (Bio-Rad standard assay) using BSA as a standard. The fluorescence intensity (fraction II-2) was determined with a LS50B Luminescence Spectrometer LS50B. EX=458 nm, EM=492 nm, both slits=2.5 nm. Table 4 shows the protein concentration, relative fluorescent (FL) intensity and intensity/μg protein in 700 μl volume. It shows that Mut32 is as bright as wildtype, while Mut15 is worse than the wildtype.

TABLE 4

| | Protein Concentration | Relative FL Intensity | Intensity/μg Protein in 700 μl Volume |
|---|---|---|---|
| Wildtype II-2 | 1.26 μg/5 μl | 37.805/5 μl | 30.00 |
| Mut15II-2 | 0.64 μg/5 μl | 10.152/5 μl | 15.86 |
| Mut32II-2 | 6.17 μg/5 μl | 186.474/5 μl | 30.22 |

III. Characterization of cFP484 and Mutants thereof (NFP-2)

A. Mutant Generation

Two deletion mutants were generated by two separate PCR reactions: Δ19 cFP484 lacks the N-terminal first 19 amino acids of cFP484, and Δ38 cFP484 lacks the N-terminal first 38 amino acids of cFP484. Mammalian expression vectors containing the DNA encoding the fluorescent protein Δ19 cFP484 or Δ38 cFP484 are generated, which are named as pΔ19 NFP2-N1 and pΔ38 NFP2-N1, respectively.

B. Transient Expression of Deletion Mutants of cFP484 in Mammalian Cells

HeLa cells were transiently transfected with mammalian expression vector pΔ19 NFP2-N1 which contains the DNA encoding the fluorescent protein Δ19 cFP484. After transfection, cells were incubated for 48 hours at 37° C. then fixed in 3.7% formaldehyde. Cells were mounted in mounting medium and observed by fluorescence microscopy. Digital images were taken with MetaMorph software (Universal Imaging Corp.) using a monochrome cooled CCD camera (Roper Scientific). The filter set XF 114 (Omega Optical) was used to visualize fluorescence emitted by Δ19 cFP484. The image was pseudocolored. Δ38 cFP484 is also fluorescent when expressed in HeLa cells.

IV. Characterization of zFP506 and Mutants thereof (NFP-3; ZsGreen)

A. Mutant Generation

A mutant of zFP506 was generated, N66M (N65M if numbered according to GFP homology alignment). Compared with wild type zFP506, N66M has the mutation of from "AAC" to "ATG" which results in the corresponding amino acid change from Asparagine (N) to Methionine (M) at the position of 66. The spectral properties of N66M are listed in Table 5.

TABLE 5

Spectral Properties of the Isolated N66M

| Species | NFP Name | Absorbance Maximum Nm | Emission Maximum nm | Maximum Extinction Coeff. | Quantum Yield | Relative Brightness* |
|---|---|---|---|---|---|---|
| Zoanthus sp. | N65M | 496 | 506 | 62,000 | 0.63 | 1.78 |

*relative brightness is extinction coefficient multiplied by quantum yield divided by the same value for A. victoria GFP.

The following additional mutants ere also generated: FP3-NA: K5E, K10E, N66M (non-aggregating mutant) (See FIG. 11); Yellow (A64G, N66K, N69D) (See FIG. 12); Yellow/bright (A64G, N66K, N69D, D94N, M120V, K157R, P231S) (See FIG. 13).

Additional mutants of NFP-3 include (according to GFP numbering): M167A; M167H; and N65K/N68D.

B. Construction and Functional Analysis of Vectors

Non-humanized zFP506 DNA was amplified via PCR and reconstructed into EGFP-N1 backbone. This vector has the same multiple cloning sites as EGFP-N1. Functional test of the generated vector was performed by transient transfection in 293 cells. 24 hours post transfection, expression of zFP506 was examined under fluorescent microscope. zFP506 showed good fluorescent intensity and comparable to EGFP-N1.

C. Generation of Destabilized zFP506 Vectors as Transcription Reporters

Since zFP506 is very stable, it is necessary to generate destabilized versions of zFP506 in order to observe the rapid turnover of the protein. By using the same technology for destabilized EGFP, two destabilized zFP506 vectors were constructed by fusing mouse ODC degradation domain to the C-terminal of zFP506. The d1 version of destabilized zFP506 has three E to A mutations within MODC degradation domain comparing to d2 version, therefore result in a shorter half-life of the protein to which MODC degradation domain fused to. Destabilized d1zFP506 and d2zFP506 were constructed in EGFP-N1 backbone D. Functional Analysis of Destabilized zFP506

Wildtype d1zFP506 was transiently transfected into 293 cells. 24 hours after transfection, CHX was added to stop protein synthesis. After 4 hour treatment, cells were examined under fluorescent microscope. It shows that fusion of MODC domain to the zFP506 slightly decreases the fluorescent intensity compared to zFP506 itself. After 4 hour treatment, there is 50% fluorescent intensity decrease.

E. Application of Destabilized d1zFP506 as Transcription Reporters

Destabilized d1zFP506 was constructed into pCRE-d1GNFP and pNF-κB-d1GNFP vectors. Its expression regulated under cAMP response element (CRE) or NF-κB response element, respectively. These vectors were transiently transfected into 293 cells, and 24 hours post transfection, the expression of d1GNFP was induced by Forskolin or TNF-α. 6 hours after induction, the culture was analysed by FACS. CRE-d1GNFP showed 7 fold of induction in fluorescence intensity, while 4 fold of induction was obtained in NF-κB-d1GNFP (data not shown). This demonstrated that the destabilized form of GNFP is applicable as transcription reporters.

F. Construction and Functional Test for Humanized zFP506 and Humanized N66M

Since mammalian expression is a very popular tool, human favored codon version is needed for better expression in mammalian cells. Each piece of human favored codon oligos was linked to form the full length of wild type and/or mutant zFP506 (hGNFP-zFP506; hGNFP-N65M. This humanized zFP506 was constituted into EGFP-N1 backbone.

V. Characterization of zFP-538 and Mutants thereof (NFP4; ZsYellow)

A mutant of zFP538 M129V (as measured from the start of the protein) was generated. M129V (M128V using GFP numbering) was generated by introducing a wrong nucleotide in PCR during site-specific mutagenesis at position 65. One bright yellow colony was obtained, and the sequence of this clone was performed. It showed that this clone contained wild type amino acid Lysine (K) at position 65, but had a substitution from Methionine (M) to Valine (V) at position 129 (numbering from start of protein; at position 128 if numbering according to GFP homology alignment).

Further investigations showed that M129V has spectral characteristics very similar to wild type protein zFP538 but folds much faster. Table 6 lists the spectral properties of M129V.

B. Generation of Destabilized zFP538 Vectors as Transcription Reporters

By using the same technology for destabilized EGFP, destabilized zFP538 vectors were constructed by fusing different mouse ODC degradation domains such as d1 and d2 to the C-terminal of zFP538. The d1 version of destabilized YNFP has three E to A mutations within MODC degradation domain compared to d2 version. Vectors pYNFPM128V-MODCd1 and pYNFPM128V-MODCd2 were constructed in EGFP-N1 backbone.

C. Functional Analysis of Destabilized zFP538

Functional test of the destabilized zFP538 was performed by transient transfection in 293 cells. After 24-hour expression, the fluorescent intensity was decreased gradually from d2 and d1 because of the fusion with different mouse ODC degradation domains. After 4-hour treatment with protein synthesis inhibitor cycloheximide, d2 fluorescent intensity did not change very much; however, d1 fluorescent intensity decreased further 50% of its original intensity. The half-life of d1 is around 4 hours.

M129V has fast folding and bright fluorescent intensity, which makes it useful for number of applications. Some fusion proteins were tested such as PKC-gamma-YNFP (M129V). PKC-gamma was observed to translocate from cytosol to the plasma membrane when cells were treated with PMA (Phorbol 12-Myristate 13-Acetate).

D. Construction and Functional Test for Humanized M129V

Humanized M129V was generated, and then placed into the pEGFP-N1 backbone. This vector has the same multiple cloning sites as pEGFP-N1. Construction of C1 and pEGFP is in the process.

TABLE 6

| | | Spectral Properties of the Isolated M128V | | | | |
|---|---|---|---|---|---|---|
| Species | NFP Name | Absorbance Maximum nm | Emission Maximum nm | Maximum Extinction Coeff. | Quantum Yield | Relative Brightness* |
| Zoanthus sp. | M128V | 531 | 540 | 25,360 | 0.43 | 0.50 |

*relative brightness is extinction coefficient multiplied by quantum yield divided by the same value for *A. victoria* GFP.

The following additional mutants were also generated: FP4-NA (K5E, K9T, M129V)(Non-Aggregating Mutant); Green (K65M GFP numbering; K66M self numbering).

Additional mutants of NFP-1 include (according to GFP numbering): D68N.

A. Construction and Functional Analysis of Vectors

Both wildtype (wt) and mutant zFP538 DNA were amplified via PCR and reconstructed to EGFP-N1 backbone. This vector has the same multiple cloning sites as EGFP-N1. Both pYNFPwt and pYNFPW129V keep the same multiple cloning sites as EGFP-N1. Functional test of the generated vectors was performed by transient transfection in 293 cells. After 24-hour expression, pYNFPwt, pYNFPM129V and EYFP were compared side by side: pYNFPwt showed less fluorescent intensity than EYFP (data not shown); however, pYNFPM129V showed as bright fluorescent intensity as EYFP by fluorescent microscopy.

E. Structural Characterization of Green Mutant

1. Analytical Ultracentrifugation:

Data show zFP538 is non-dissociating trimer of 80 kD/dimer-tetramer equilibrium with S values of about 6 and 8; results not conclusive, but sure that there is more than one species.

2. Structure:

Tetramer, extremely similar to DsRed; no idea why wildtype is yellow, chromophore is identical to that of GFP; although the tetramers of dsRed and zFP538 are essentially identical in the overall configuration and in the positioning of the interfacial regions, the residues involved in interfacial contacts are not conserved. This finding indicates that a lot of variability is tolerated and monomers can be created.

VI. Characterization of dsFP483 and Mutants thereof (NFP-5)

Mutants of NFP-5 include (according to GFP numbering): N68S; I112S; and N68S/I112S.

VII. Characterization of drFP583 and Mutants thereof (NFP-6; DsRed; DsRed2)

A. Expression in Mammalian Cells

HeLa cells were transfected either with plasmid pDsRed1-N1 (vector containing the DNA encoding drFP583) or plasmid pEGFP-C1 (encoding EGFP from *Aequorea victoria*). Immediately after the transfection, cells were mixed and plated on coverslips. Cells were incubated for 48 hours at 37° C. then fixed in 3.7% formaldehyde. Cells were mounted in mounting medium and observed by fluorescence microscopy. Images were taken from the same field of view with Chroma filter set 31001 for EGFP and filter set 31002 for drFP583 using a cooled CCD camera (Roper Scientific) and MetaMorph software (Universal Imaging). The images were pseudocolored and overlayed. Phase contrast was taken from the same field of view and overlayed.

B. Generation of Humanized drFP583

Since mammalian expression is a very popular tool, human favored codon version is needed for better expression in mammalian cells. Humanized drFP583 was therefore generated by changing wild type drFP583 nucleotide sequence to optimize the codons for expression of the fluorescent protein. The nucleotide sequence of this humanized mutant is provided in FIG. 16.

C. Expression of Humanized drFP583 in Mammalian Cells

HeLa cells were transiently co-transfected with plasmids pECFP-Nuc, pEYFP-Tub and pDsRed1-Mito (humanized drFP583). After transfection, cells were incubated for 48 hours at 37° C. then fixed in 3.7% formaldehyde. Cells were mounted in mounting medium and observed by fluorescence microscopy. Images were taken of one cell co-expressing all three fluorescent proteins with Omega filter set XF 35 for DsRed1-Mito, XF 104 for EYFP-Tub and XF 114 for ECFP-Nuc using a cooled CCD camera (Roper Scientific) and MetaMorph software (Universal Imaging). Individual images were pseudocolored and overlayed to show all three signals in one image. Protein DsRed1-Mito localizes to mitochondria, EYFP-Tub localizes to the microtubular network, and ECFP-Nuc localizes to the nucleus.

As a conclusion, drFP583 does emit to a low extent also in the cyan (ECFP), green (EGFP) and yellow-green (EYFP) emission channels (filter sets). High expression levels or highly concentrated protein in intracellular structures can therefore result in high signal intensities that will give some bleedthrough in the other emission wavelengths. The bleedthrough is small and should not affect multiple labeling recording in most cases.

D. Mutants of Humanized drFP583

Mutants of humanized drFP583 were generated using error prone PCR technique (Clontech). Mutations occurred at amino acids 42, 71, 105, 120, 161 and 197 (numbering starting from the first Methionine). Table 7 lists the mutants that were generated and their properties.

TABLE 7

Mutants of Humanized drFP583

| Mutant | Mutations | Properties |
|---|---|---|
| E5 | V105A, S197T | Overnight in *E. coli* emitting green fluorescence; in vitro maturing to red over 28 h at 37° C. on 80% (retains 20% green peak); folding faster than wild type drFP583 (~28 h) |
| E8 | N42H | Always two peaks green & red (~1:1) folding faster than E5 (~8 h) |
| E5up | V105A | red from the beginning; folding faster than E5 (~12 h) |
| E5 down | S197T | phenotype is similar to E5 |
| E57 | V105A, I161T, S197A | like E5 but folding faster (~8-10 h); ~5% of green peak left at the end (See FIG. 18) |
| AG4 | V71M, V105A, S197T | bright green, no red at all; fast folding (~16 h) |
| AG45 | V71M, V105A, Y120H, S197T | like AG4 but twice brighter |
| FP6 (E57)-NA: | R2A, K5E, K9T, V105A, I161T, S197A. | Non-aggregating (See FIG. 19) |
| E5-NA: | R2A, K5E, K9T, V105A, S197T | (non-aggregating Fluorescent Timer) (See FIG. 17) |
| E83 | N42H, V71A, I180V | |

E. Characterization and Applications of E5 Mutant

E5 (V105A, S197T) changes its fluorescence from green to red over time both in vitro and in vivo, in *E. coli* and in mammalian cells. Also, E5 folds faster than wild type drFP583 both in. *E. coli* and mammalian cells.

Since it allows the "two color" reporting mode for monitoring of the promoter activity, i.e., for both active or shutdown state of the promoter, there is a separate color, serving as an indicator of that state, E5 can be used as a transcriptional reporter. Different from "one color" mode, "two color" mode has a measurable signal (color) present for both states of the process as opposed to "one color" mode (e.g. destabilized GFP) wherein the absence of the color is an indicator of the second state. Namely, newly produced E5 protein fluoresces in green, indicating on-going promoter activity. Over time, the protein will mature, acquiring the red fluorescence. So if the promoter is no longer active, all the protein will eventually mature, resulting in the dominant red fluorescence. In case the promoter is still active both red and green fluorescence will be readily detected. Thus E5 as a "two color" reporter allows study of gene expression similar to destabilized GFP, but with permanent "signature" of past gene activity in the cells, tissues or entire organism. For example, at the tissue level, E5 may help to distinguish the stem cells from differentiated cells. Providing the promoter is only active in the stem cells, the E5 reporter will label the stem cell population in green and red, the progenitor cells would be labeled predominantly in red, the terminally differentiated will not fluoresce (due to the titration out of protein during cell division).

E5 can be used for spatial and temporal visualization of newly synthesized vs. accumulated fusion proteins. That is, E5 could function like a fusion tag. Possible applications envisaged at different organizational levels. At the cellular level, E5 may help to visualize and distinguish the newly synthesized proteins in various compartments such as outer membrane, microvillae, ER, Golgi, mitochondria, nuclei, various components of cellular matrix and focal adhesion complexes. At the tissue level, E5 may be helpful in visualizing newly formed vs. preexisting structures e.g. membrane junctions, components of extracellular matrix.

One of the most fascinating applications of E5 seems to be in the study of the mother-daughter relationship during the cell division and migration. A wide horizon is opening in the fields of development as well as in the adult organisms to study the cell migration and differentiation. Allowing visualization of the expression "history", E5 can help to distinguishing between the mother cells where the promoter is actually active vs. the daughter cells containing the accumulated protein but not producing fresh protein anymore. It would enable the study of the cell fates during development and organ remodeling, thus distinguishing between cell migration and cell expansion or differentiation.

In conclusion, E5 is basically applicable to any situation where GFP was previously used. Main advantage is that E5 can track down "the history" of promoter activity or protein localization in cells or tissues. With a better protein stability than GFP, E5 allows longer analysis window (wild type drFP583 is stable for at least 4 weeks in *Xenopus*, while EGFP starts to faint after two weeks).

F. Characterization and Applications of E8 Mutant

E8 (N42H) has two fluorescence maximums, green and red, at all times and it folds much faster than drFP583 (Table 7).

Since it detects both green and red fluorescence simultaneously, E8 may be useful for studying processes related to blood circulation and proteins/cells trafficking. Blood absorbs the green fluorescence; thus only the red fluorescence will be visible while the protein is trafficking in the blood. Both green and red fluorescence could be detected outside the bloodstream making the whole process easy to visualize and record. Monitoring both red and green fluorescence simultaneously may also help to reduce the background fluorescence problems for some tissues or cell's.

G. Generation of drFP583/dmFP592 Hybrid Using Shuffling Procedure

Non-humanized wild type coding region fragments from drFP583 and dmFP592 were amplified by PCR (22 cycles, 95° C., 15 sec., 68° C. 1 min 20 sec.) using 1 ng of corresponding bacterial expression plasmids (pQE-30 derivatives with drFP583 and dmFP592 inserts, respectively) as templates. Oligonucleotides

```
A   (ACATGG ATCCAGGTCTTCCAAGAATGTTATC,
     SEQ ID No. 23),

B   (TAGTACTCG AGCCAAGTTCAGCCTTA, SEQ ID No. 24),

C   (ACATGGATCCAG TTGTTC CAAGAATGTGAT,
     SEQ ID No. 25),
and

D   (TAGTACTCGAGGCCATTA CCGCTAATC, SEQ ID No. 26)
``` were used as primers for amplifying these fragments in a concentration of 0.2 mM.

The PCR products were then purified by QIAquick PCR Purification Kit (QIAGEN). Afterwards, the purified fragments drFP583 and dmFP592 (300-500 ng each) were digested with restriction endonucleases EcoRI, HindIII and DraI (10 U each) simultaneously. Reactions were performed in BamHI restriction buffer (NEB) supplemented BSA for 3 h at 37° C. Total reaction volume was 30 ml. Upon completion, the resulted restriction fragments from each restriction reaction were separated by electrophoresis in agarose gels (1.5%), cut from gel and purified by QIAquick Gel Purification Kit (QIAGEN). The resulting sets of the purified restriction fragments from both drFP583 and dmFP592 were combined together and 50 ng of them were put into ligation mix (1×T4 DNA ligation buffer, 400 NEB U of T4 DNA ligase) in total volume of 30 ml. The ligation was performed for 3 h at room temperature and stopped by heating at 70° C. within 20 min.

The ligation mixture was then diluted by water ten-folds, and 1 ml of the dilution was preformed for PCR reaction (20 cycles, 95° C., 15 sec. 68° C. 1 min 20 sec) as template. Four oligonucleotides A, B, C, and D (SEQ ID Nos. 58-61, respectively) were used simultaneously as primers for amplifying these fragments in a concentration of 0.1 mM each. After electrophoresis in an agarose gel (1.5%), the target fragment was purified by QIAquick Gel Purification Kit (QIAGEN) and digested with restriction endonucleases BamHI and XhoI (30-50 U each) simultaneously in BamH I restriction buffer (NEB) supplemented with BSA for 3 h at 37° C. After purification, the resulting fragment was cloned in pQE-30 plasmid linearized by BamHI and SalI. Ligation reaction was performed in 1×T4 DNA ligation buffer and 400 NEB U of T4 DNA ligase with a total volume of 20 ml for overnight at 16° C. After transformation of *E. coli* cells by ⅕ of the ligation volume and incubation on LB/1% agar plates which were supplemented by 100 mg/ml Ampacilin and 0.1 mM IPTG at 37° C. for overnight, the resulting *E. coli* colonies were screened visually under fluorescent microscope using rhodamine filter set. The brightest red colonies were picked up and placed in 200 ml LB medium with 100 mg/ml of Ampacilin. At $OD_{600}$=0.6, the *E. coli* culture was induced by IPTG (final concentration was 1 mM) and the fermentation continued for overnight. Purification of recombinant protein containing N-terminus 6× his tag was performed using TALON metal-affinity resin according to manufacturer's protocol.

H. Spectral Properties of drFP583/dmFP592 Hybrid

The emission and excitation spectra for drFP583/dmFP592 hybrid protein are basically the same as for dmFP592. Table 8 lists the spectral properties of drFP583/dmFP592 hybrid protein.

TABLE 8

| | Spectral Properties of drFP583/dmFP592 Hybrid | | | | |
|---|---|---|---|---|---|
| nFP Name | Absorbance Maximum nm | Emission Maximum nm | Maximum Extinction Coeff. | Relative Quantum Yield* | Relative Brightness** |
| drFP583/ dmFP592 | 573 | 592 | 35,000 | 0.24 | 0.3 |

*relative quantum yield was determined as compared to the quantum yield of *A. victoria* GFP.
**relative brightness is extinction coefficient multiplied by quantum yield divided by the same value for *A. victoria* GFP.

I. Humanized drFP583/dmFP592 Hybrid and Mutants drFP583/dmFP592 hybrid was humanized. Further, two mutants were generated based on the humanized drFP583/dmFP592, i.e., drFP583/dmFP592-2G and drFP583/dmFP592-Q3. drFP583/dmFP592-2G (i.e. 6/92G) contains two substitutions, K15Q and T217S (Self numbering). This mutant was derived from the humanized drFP583/dmFP592 hybrid gene by random mutagenesis using Diversity PCR Mutagenesis Kit (Clontech) according to the corresponding protocol. drFP583/dmFP592-Q3 (6/9Q) contains three substitutions, K15Q and K83M and T217S (self numbering). drFP583/dmFP592-Q3 mutant was derived from drFP583/dmFP592-2G mutant by random mutagenesis using Diversity PCR Mutagenesis Kit (Clontech) according to the corresponding protocol. A non-aggregating mutant of 6/9 Q, i.e. 6/9 QNA, was also produced, which the following substitutions: K5E, K9T, K15Q, K83M, T217S (self numbering). The sequences of a humanized 6/9 Q hybrid protein are provided in FIG. 22.

excitation in green part of spectrum except any spectral overlapping and background fluorescence.

The method of generating drFP583/dmFP592 hybrid can have a general utility for generating hybrid genes (i.e., genes containing parts of different genes in various combinations) with improved fluorescent characteristics.

Additionally, drFP583/dmFP592-Q3 is the first red-shifted mutant, which demonstrates that spectral-shifted mutant could be obtained by random mutagenesis.

K. Further Characterization

| Mutant name | Position of mutation(s) | Parental clone/gene | residual green fluorescence (% from red) | | in vitro maturation t½ |
|---|---|---|---|---|---|
| DsRed | wild type | | 4-5 after 18-24 hours | Not seen ON in E coli, 16-24 h in 293 cells | 9-10 |
| E5 | V105A, S197T | FP#6 (w.t.) | 20% after 43 hours, eventually drops to 10% | In E. coli GREEN o/night, in 293 cells both color develop faster than wt | 9-10 |
| E5-UP | V105A | E5(split) | 3% after 24 hours eventually zero | beeter folding in bacteria | 9-10 |
| E5-DOWN | S197T | E5(split) | similar to E5 | similar to E5 | 9-10 |
| E57 | V105A, I161T, S197A | E5 | 5% after 8 h, 4% after 24 hours | better folding and faster maturation of fluorophore | 3-4 |
| AG4 | V71M, V105A, S197T | E5 | 100% green at all time | bright GREEN, no RED at all | 1.5-2 |
| AG45 | V71M, V105A, Y120H, S197T | AG4 | 100% green at all time | ~2× brighter than AG4 | 1.5-2 |
| E8 | N42H | FP#6 (w.t.) | Green/Red ratio is 3:2 | better folding and faster maturation of fluorophore | 3-4 |
| E83 | N42H, V71A, I180V | E8 | Green/Red ratio is 1:1 | same as E8 | 3-4 | green fluorescence:
RFP about 4-5% wt after 18-24 hours, remains.
E5 about 20% after 43 hours eventually drops to 10%
E5up about 3% after 24 hours eventually goes to zero.
E5down about 20% after 24 hours, eventually drops to 10%
E57 5% after 8 hours, 4% after 24 hours; faster maturation than wt RFP drFP583/dmFP592-2G has similar brightness and folding rate as for non-humanized drFP583/dmFP592 hybrid. While drFP583/dmFP592-Q3 could be seen in E. coli cells as more dark red than parental variant, i.e., drFP583/dmFP592-2G, and the purified protein solution has purple color. drFP583/dmFP592-Q3 has the emission maximum of 616 nm and excitation maximum of 580 nm.

J. Applications of Hybrid Mutants

Similar to fluorescent protein drFP583 or dmFP592, drFP583/dmFP592-Q3 can be used as a tool for investigation of protein expression, transport and protein interactions in vivo, monitoring of promoter activity, and as a transcription reporter or fusion tag. Besides, drFP583/dmFP592-Q3 can be chosen as the most convenient partner to one of the existing green fluorescent protein variants in two/triple color labeling assays for simultaneous detection of expression of two or more proteins in vivo due to its strongly red-shifted position of emission maximum and practical absence of VIII. Characterization of asFP600 and Mutants thereof (NFP-7; AsRed)

A. Mutant Generation

A mutant of asFP600 was generated, Mut1. Compared with wild type asFP600, Mut1 has the following substitutions: T68A and A143S from start of protein (T to A at position 70 and A to S at position 148 under numbering according to GFP). Target substitution A143S was generated by means of site-specific mutagenesis using PCR with primers that carried the mutation. During this mutagenesis random substitution T68A was generated by introducing a wrong nucleotide in PCR. The substitution T68A is not necessary for fluorescence and practically does not affect the fluorescence. Table 9 lists the spectral properties of Mut1. Another mutant of asFP600 was generated, having a substitution of the Alanine at position 184 to Serine (according to GFP numbering).

TABLE 9

Spectral Properties of the Isolated Mut1

| Species | NFP Name | Absorbance Maximum Nm | Emission Maximum nm | Maximum Extinction Coeff. | Quantum Yield | Relative Brightness* |
|---|---|---|---|---|---|---|
| Anemonia sulcata | Mut1 | 573 | 595 | 15,500 | 0.05 | 0.03 |

*relative brightness is extinction coefficient multiplied by quantum yield divided by the same value for *A. victoria* GFP.

Yet one more mutant was generated, i.e., mut M35-5/mut1 (=7A): F4L, K12R, F35L, T68A, F84L, A143S, K163E, M202L (positions relative to the start of the protein)

A non-aggregating version of this mutant was also made, i.e., 7A-NA: K6T, K7E, F4L, K12R, F35L, T68A, F84L, A143S, K163E, M202L (positions relative to the start of the protein)

The humanized FP-7 sequences are provided in FIG. 21.

B. Construction and Functional Analysis of Vectors

Non-humanized mutant asFP600 (RNFP) DNA were amplified via PCR and reconstructed to EGFP-N1 backbone. This vector (pRNFP-N1) has the same multiple cloning sites as EGFP-N1.

Functional test of the generated vector was performed by transient transfection in 293 cells. 24 hours post transfection, expression of asFP600 was examined under fluorescent microscope. asFP600 showed good fluorescent intensity, however, the expression of asFP600 concentrated at the nucleus.

C. Generation of Cytosal Expressed asFP600

Since the nuclear localization of asFP600 limited some of the application of this protein as transcription reporter or pH sensor, cytosal expression of this protein would be needed for this purpose. A nuclear export sequence in humanized codon usage was fused to the N-terminus of asFP600, and placed into the EGFP-N1 vector, resulted in pNE-RNFP.

Functional test of NE-RNFP is performed by transient transfect the pNE-RNFP into 293 cells. 24 hours post transfection, expression of NE-RNFP is examined under fluorescence microscope. Red fluorescence was observed to be distributed in the cytosol but not in the nucleus.

D. Generation of Destabilized asFP600 Vectors as Transcription Reporters

Since asFP600 is very stable, it is necessary to generate destabilized versions of asFP600 in order to observe the rapid turnover of the protein. By using the same technology for destabilized EGFP, two destabilized NE-RNFP vectors were constructed by fusing mouse ODC degradation domain to the C-terminal of NE-RNFP. The d1 version of destabilized RNFP has three E to A mutations within MODC degradation domain comparing to d2 version, therefore result in a shorter half-life of the protein to which MODC degradation domain fused. Destabilized d1RNFP and d2RNFP were constructed in EGFP-N1 backbone.

E. Functional Analysis of Destabilized asFP600 d2 version of the none-humanized asFP600 was transiently transfected into 293 cells. One day after transfection, CHX was added to inhibit protein synthesis. 3 hours after treatment, cells were examined under fluorescent microscope. It showed that fluorescent intensity decreased ~50%.

F. Construction and Functional Test for Humanized Mut1

Humanized Mut1 was generated. The humanized Mut1 was then placed into the pEGFP-N1 backbone. This vector has the same multiple cloning sites as pEGFP-N1. Construction of C1 and pEGFP is in the process.

It is evident from the above discussion and results that the subject invention provides important new chromoproteins and fluorescent proteins and nucleic acids encoding the same, where the subject proteins and nucleic acids find use in a variety of different applications. As such, the subject invention represents a significant contribution to the art.

IX. Summary Table of Mutant Fluorescent Proteins

TABLE 10

| NFP# | name | Mutants: aa numbering according to GFP homology alignment | Mutants: aa numbering according to aa sequence of protein proper |
|---|---|---|---|
| 1 | amFP486 | K65M (mut32) | K68M (mut32) |
| | | K65L (mut15) | K68L (mut15) |
| | | FP1-NA: K6E, K65M | FP1-NA: K6E, K68M |
| | | (non-aggregating mut 32) | (non-aggregating mut 32) |
| 2 | CFP484 | 19 (N-terminal 19 aa deleted) | |
| | | 38 (N-terminal 38 aa deleted) | |
| 3 | zFP506 | Mut: N65M | Mut: N66M |
| | | FP3-NA: K5E, K10E, N65M | FP3-NA: K5E, K10E, N66M (non- |
| | | (non-aggregating mutant) | aggregating mutant) |
| | | Yellow (A63G, N65K, N68D) | Yellow (A64G, N66K, N69D) |
| | | Yellow/bright (A63G, N65K, N68D, | Yellow/bright (A64G, N66K, N69D, |
| | | D95N, M119V, K158R, P232S) | D94N, M120V, K157R, P231S) |
| 4 | zFP540 | Mut: M128V | Mut: M129V |
| | | FP4-NA: K5E, K9T, M128V | FP4-NA: K5E, K9T, M129V (non- |
| | | (non-aggregating mutant) | aggregating mutant) |
| | | Green (K65M) | Green (K66M) |

TABLE 10-continued

| NFP# | name | Mutants: aa numbering according to GFP homology alignment | Mutants: aa numbering according to aa sequence of protein proper |
|---|---|---|---|
| 5 | dsFP483 | | |
| 6 | DsFP583 | | FP6 (E57)-NA: R2A, K5E, K9T, V105A, I161T, S197A. E5 (V105A, S197T; Fluorescent Timer) E5-NA: NA: R2A, K5E, K9T, V105A, S197T (non-aggregating Fluorescent Timer); E5up (V105A; faster maturing, brighter) E5down (S197T, fluorescent timer phenotype) E57 (V105A, I161T, S197A; faster chromophore maturation, brighter) AG4 (V71M, V105A, S197T; green only) AG45 (V71M, V105A, Y120H, S197T; green only) E8 (N42H; green/red) E83 (N42H, V71A, I180V; green/red) |
| 6/9 hybrid | | | 6/9 Q (K15Q, K83M, T217S) 6/9Q-NA: (S2del, C3del, accidentally deleted) K5E, K9T, K15Q, K83M, T217S. Other mutants: 6/92G (K15Q, T217S) |
| 7 | asFP595 | mut1: T70A, A148S | mut1: T68A, A143S |
| 7A | | mut M35-5/mut1(=7A): F7L, K15R, F38L, T70A, F88L, A148S, K170E, M208L. | mut M35-5/mut1(=7A): F4L, K12R, F35L, T68A, F84L, A143S, K163E, M202L 7A-NA:: K6T, K7E, F4L, K12R, F35L, T68A, F84L, A143S, K163E, M202L (non-aggregating version of 7A) |

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A nucleic acid present in other than its natural environment, wherein said nucleic acid encodes a chromo- or fluorescent protein, wherein said protein has a sequence identity of at least 90% with SEQ ID NO:2.

2. The nucleic acid according to claim 1, wherein said protein has an absorbance maximum ranging from about 300 to 700 nm.

3. The nucleic acid according to claim 1, wherein said protein has an absorbance maximum ranging from about 350 to 650 nm.

4. The nucleic acid according to claim 1, wherein said protein has an absorbance maximum ranging from about 400 to 600 nm.

5. The nucleic acid according to claim 1, wherein said protein has an excitation spectrum ranging from about 300 to 700 nm and an emission spectrum ranging from about 400 to 800 nm.

6. The nucleic acid according to claim 1, wherein said protein has an excitation spectrum ranging from about 350 to 650 nm and an emission spectrum ranging from about 425 to 775 nm.

7. The nucleic acid according to claim 1, wherein said protein has an excitation spectrum ranging from about 400 to 600 nm and an emission spectrum ranging from about 450 to 750 nm.

8. The nucleic acid according to claim 1, wherein said protein has one or more amino acid substitutions selected from amino acid substitutions at positions 2, 5, 9, 105 and 197 as compared to SEQ ID NO:2.

9. The nucleic acid according to claim 1, wherein said protein has one or more amino acid substitutions selected from R2A, K5E, K9T, V105A, and S197T as compared to SEQ ID NO:2.

10. A nucleic acid present in other than its natural environment that encodes a chromo and/or fluorescent protein, wherein said protein is either:
   (a) from a non-bioluminescent Cnidarian species; or
   (b) from a non-Pennatulacean Anthozoan and
wherein said protein has a sequence identity of at least 90% with SEQ ID NO:2.

11. The nucleic acid according to claim 10, wherein said non-bioluminescent Cnidarian species is an Anthozoan species.

12. The nucleic acid according to claim 10, wherein said nucleic acid is isolated.

13. The nucleic acid according to claim 10, wherein said protein has the amino acid sequence of SEQ ID NO:2.

14. A nucleic acid present in other than its natural environment that encodes a chromo and/or fluorescent protein that is either:
   (i) from a non-bioluminescent Cnidarian species; or
   (ii) from a non-Pennatulacean Anthozoan species;
wherein said protein has a sequence identity of at least 90% with SEQ ID NO:2, and
wherein said protein has an absorbance maximum ranging from about 300 to 700 nm.

15. The nucleic acid according to claim 14, wherein said non-bioluminescent Cnidarian species is an Anthozoan species.

16. A construct comprising a vector and a nucleic acid that encodes a chromo and/or fluorescent protein that is either:
   (i) from a non-bioluminescent Cnidarian species; or
   (ii) from a non-Pennatulacean Anthozoan species; and
wherein said protein has a sequence identity of at least 90% with SEQ ID NO:2.

17. The construct according to claim 16, wherein said non-bioluminescent Cnidarian species is an Anthozoan species.

18. An expression cassette comprising:
   (a) a transcriptional initiation region functional in an expression host;
   (b) the nucleic acid according to claim 1; and
   (c) a transcriptional termination region functional in said expression host.

19. An isolated host cell comprising an expression cassette according to claim 18 as part of an extrachromosomal element or integrated into the genome of a host cell as a result of introduction of said expression cassette into said host cell.

20. A kit comprising the nucleic acid according to claim 1 and instructions for using said nucleic acid.

* * * * *

UNITED STATES PATENT AND TRADEMARK OFFICE
CERTIFICATE OF CORRECTION

| | | |
|---|---|---|
| PATENT NO. | : 7,338,784 B2 | Page 1 of 1 |
| APPLICATION NO. | : 11/607706 | |
| DATED | : March 4, 2008 | |
| INVENTOR(S) | : Sergey A. Lukyanov | |

It is certified that error appears in the above-identified patent and that said Letters Patent is hereby corrected as shown below:

On the title page item 60, line 21, following "now abandoned", insert the following text:

and a continuation-in-part of application No. 09/210,330, filed on Dec. 11, 1998, now abandoned.

Signed and Sealed this

Second Day of December, 2008

JON W. DUDAS
*Director of the United States Patent and Trademark Office*